US011696914B1

(12) United States Patent
Ekins et al.

(10) Patent No.: US 11,696,914 B1
(45) Date of Patent: Jul. 11, 2023

(54) USE OF PYRONARIDINE, TILORONE, AND QUINACRINE AGAINST MARBURG VIRUS AND OTHER VIRUS INFECTIONS

(71) Applicant: Collaborations Pharmaceuticals, Inc., Raleigh, NC (US)

(72) Inventors: Sean Ekins, Fuquay Varina, NC (US); Thomas R. Lane, Durham, NC (US); Ana C. Puhl Rubio, Fuquay Varina, NC (US)

(73) Assignee: Collaborations Pharmaceuticals, Inc., Raleigh, NC (US)

( * ) Notice: Subject to any disclaimer, the term of this patent is extended or adjusted under 35 U.S.C. 154(b) by 190 days.

(21) Appl. No.: 17/092,058

(22) Filed: Nov. 6, 2020

Related U.S. Application Data

(60) Provisional application No. 62/931,456, filed on Nov. 6, 2019.

(51) Int. Cl.
*A61K 31/4745* (2006.01)
*A61P 31/14* (2006.01)
*A61K 31/357* (2006.01)
*A61K 9/00* (2006.01)
*A61P 31/20* (2006.01)
*A61K 31/138* (2006.01)
*A61P 31/16* (2006.01)
*A61P 31/22* (2006.01)
*A61K 31/473* (2006.01)

(52) U.S. Cl.
CPC ........ *A61K 31/4745* (2013.01); *A61K 9/0019* (2013.01); *A61K 9/0043* (2013.01); *A61K 9/0053* (2013.01); *A61K 31/138* (2013.01); *A61K 31/357* (2013.01); *A61K 31/473* (2013.01); *A61P 31/14* (2018.01); *A61P 31/16* (2018.01); *A61P 31/20* (2018.01); *A61P 31/22* (2018.01)

(58) Field of Classification Search
CPC ............................ A61K 31/4745; A61P 31/14
See application file for complete search history.

(56) References Cited

FOREIGN PATENT DOCUMENTS

| WO | WO 2021/062189 | 4/2021 |
| WO | WO 2022/061019 | 3/2022 |

OTHER PUBLICATIONS

Baker et al. "Molecular architecture of the nucleoprotein C-terminal domain from the Ebola and Marburg viruses," Acta Cryst. 2016, D72, 49-58 (Year: 2016).*
Falzarano et al. "Lack of protection against Ebola virus from chloroquine in mice and hamsters," Emerging Infectious Diseases. 2015, vol. 21, No. 6, pp. 1065-1067 (Year: 2015).*
Ekins et al. "Machine learning models identify molecules active against the Ebola virus in vitro," F1000 Research, 2016, 4:1091 (Year: 2016).*

(Continued)

*Primary Examiner* — Shengjun Wang
(74) *Attorney, Agent, or Firm* — Jenkins, Wilson, Taylor & Hunt, P.A.

(57) ABSTRACT

Methods of treating or preventing diseases caused by viral infections via the administration of pyronaridine, quinacrine, and/or tilorone are described. The viral infections can be caused by viruses such as Marburg virus (MARV), Chikungunya virus (CHIKV), norovirus, Middle East Respiratory Syndrome coronavirus (MERS-CoV), and Nipah virus.

5 Claims, 38 Drawing Sheets
(28 of 38 Drawing Sheet(s) Filed in Color)

(56) References Cited

OTHER PUBLICATIONS

Sagara et al. "Safety and efficacy of re-treatments with pyronaridine-artesunate in African patients with malaria: a substudy of the WANECAM randomized trial," The Lancet, 2016, vol. 16, Issue 2, pp. 189-198 (Year: 2016).*
Munoz-Fontela et al. "Ebola Virus Disease in humans: pathophysiology and immunity," Marburg and Ebolaviruses. Editor Muhlberger et al. Springer, 2017, pp. 141-169 (Year: 2017).*
Anantpadma et al., "Ebola Virus Bayesian Machine Learning Models Enable New In Vitro Leads." ACS Omega, vol. 4, pp. 2353-2361 (2019).
Anantpadma et al., "Large-Scale Screening and Identification of Novel Ebola Virus and Marburg Virus Entry Inhibitors." Antimicrob Agents Chemother, vol. 60, pp. 4471-4481 (2016).
Bai et al., "Clinical and Virological Characteristics of Ebola Virus Disease Patients Treated With Favipiravir (T-705)—Sierra Leone, 2014." Clin infect Dis, vol. 63, pp. 1288-1294 (2016).
Bai et al., "Drug repurposing for Ebola virus disease: principles of consideration and the Animal Rule." J Pharm Sci, vol. 108, pp. 798-806 (2019).
Baker et al., "A bibliometric review of drug repurposing." Drug Discov Today, vol. 23, pp. 661-672 (2018).
BBC. "Ebola drugs show '90% survival rate' in breakthrough trial." (2019). https://www.bbc.com/news/world-africa-49326505.
Bixler et al., "Efficacy of favipiravir (T~705) in nonhuman primates infected with Ebola virus or Marburg virus." Antiviral Res, vol. 151, pp. 97-104 (2018).
Bornholdt et al., "A Two-Antibody Pan-Ebolavirus Cocktail Confers Broad Therapeutic Protection in Ferrets and Nonhuman Primates." Cell Host Microbe, vol. 25, pp. 49-58 (2019).
Brouillette et al., "Production of Filovirus Glycoprotein-Pseudotyped Vesicular Stomatitis Virus for Study of Filovirus Entry Mechanisms," Author manuscript, 12 pages, published in final edited form as Methods Mol Biol, vol. 1628, pp. 53-63 (2017).
Camarda et al., "Antimalarial activity of primaquine operates via a two-step biochemical relay." Nat Commun, vol. 10, p. 3226 (2019).
Chan et al., "Efficacy of Ebola Glycoprotein-Specific Equine Polyclonal Antibody Product Against Lethal Ebola Virus infection in Guinea Pigs." J Infect Dis, vol. 218, pp. S603-S611 (2018).
Chen et al., "Axl inhibitor R428 induces apoptosis of cancer cells by blocking lysosomal acidification and recycling independent of Axl inhibition." Am J Cancer Res, vol. 8, pp. 1466-1482 (2018).
Chepurnov et al., "Study of the pathogenesis of Ebola fever in laboratory animals with different sensitivity to this virus." Bull Exp Biol Med, vol. 132, pp. 1182-1186 (2001).
Comer et al., "Filovirus Virulence in Interferon α/β and γ Double Knockout Mice and Treatment with Favipiravir." Viruses, vol. 11, Article No. 137 (2019).
Cong et al., "Evaluation of the Activity of Lamivudine and Zidovudine against Ebola Virus." PLoS One, vol. 11, Article ID e0166318 (2016).
Corti et al., "Protective monotherapy against lethal Ebola virus infection by a potently neutralizing antibody." Science, vol. 351, pp. 1339-1342 (2016).
Croft et al., "Review of pyronaridine anti-malarial properties and product characteristics." Malar J, vol. 11, Article No. 270 (2012).
Dowall et al., "Antiviral Screening of Multiple Compounds against Ebola Virus." Viruses, vol. 8 (2016).
Dowall et al., "Chloroquine inhibited Ebola virus replication in vitro but failed to protect against infection and disease in vivo guinea pig model." J Gen Virol vol. 96, pp. 3484-3492 (2015).
Duvvuri et al., "A new approach for enhancing differential selectivity of drugs to cancer cells." ACS Chem. Biol, vol. 1, pp. 309-315 (2006).
Dyall et al., "In Vitro and In Vivo Activity of Amiodarone Against Ebola Virus." J Infect Dis, vol. 218, pp. S592-S596 (2018).
Dziekan et al., "Identifying purine nucleoside phosphorylase as the target of quinine using cellular thermal shift assay." Sci Transl Med, vol. 11 (2019).
Ekins et al., "Efficacy of Tilorone Dihydrochloride against Ebola Virus Infection." Antimicrobial Agents and Chemotherapy, vol. 62, Article ID e01711-17 (2018).
Ekins et al., "Finding small molecules for the 'next Ebola'." F1000Res, vol. 4, Article No. 58 (2015).
Ekins et al., "In silico repositioning of approved drugs for rare and neglected diseases." Drug Discov Today, vol. 16, pp. 298-310 (2011).
Ekins et al., "Machine learning models identify molecules active against Ebola virus in vitro." F1000Res, vol. 4, p. 1091 (2015).
Fischer et al., "Drug-induced lysosomal storage of sulphated glycosaminoglycans." Gen Pharmacol, vol. 27, pp. 1317-1324 (1996).
Formenty et al., "Outbreak of Ebola hemorrhagic fever in the Republic of the Congo, 2003: a new strategy?" Med Trop (Mars), vol. 63, pp. 291-295 (2003).
Ghosh et al., "Aryl-alkyl-lysines: small molecular membrane-active antiplasmodial agents." Medchemcomm, vol. 8, pp. 434-439 (2017).
Guedj et al., "Antiviral efficacy of favipiravir against Ebola virus: A translational study in cynomolgus macaques." PLos Med, vol. 15, Article ID e1002535 (2018).
Hernandez et al., "High throughput and Computational Repurposing for Neglected Diseases." PharmRes, vol. 36, p. 27 (2018).
Homewood et al., "Lysosomes, pH and the anti-malarial action of chloroquine." Nature, vol. 235, pp. 50-52 (1972).
Ikeda et al., "Drug-induced phospholipidosis is caused by blockade of mannose 6-phosphate receptor-mediated targeting of lysosomal enzymes." Biochem Biophys Res Commun, vol. 377, pp. 268-274 (2008).
Ilunga et al., "The Ongoing Ebola Epidemic in the Democratic Republic of Congo, 2018-2019." N Engl J Med, vol. 381, pp. 373-383 (2019).
Jayaraman et al., "Determination of pyronaridine in blood plasma by high-performance liquid chromatography for application in clinical pharmacological studies." J Chromatogr B, vol. 690, pp. 253-257 (1997).
Johansen et al., "FDA-approved selective estrogen receptor modulators inhibit Ebola virus infection." Sci Transl Med, vol. 5, Article ID 190ra79 (2013).
Jonas, "Pandemic bonds: designed to fail in Ebola." Nature, vol. 572, p. 285 (2019).
Kerber et al., "Laboratory Findings, Compassionate Use of Favipiravir, and Outcome in Patients With Ebola Virus Disease, Guinea, 2015—A Retrospective Observational Study." J Infect Dis, vol. 220, pp. 195-202 (2019).
Kiley et al., "Filoviridae: a taxonomic home for Marburg and Ebola viruses?" Intervirology, vol. 18, pp. 24-32 (1982).
Kouznetsova et al., "Identification of 53 compounds that block Ebola virus-like particle entry via a repurposing screen of approved drugs." Emerging Microbes and Infections; London, vol. 3, Article ID e84 (2014).
Lane et al., "Pyronaridine tetraphosphate efficacy against Ebola virus infection in guinea pig." Antiviral Research, vol. 181, Article No. 104863 (2020).
Lane et al., "Repurposing Pyramax quinacrine, and tilorone as treatments for Ebola virus disease." Antiviral Research, vol. 182, Article No. 104908 (2020).
Lane et al., "Repurposing Quinacrine Against Ebola Virus Infection In vivo." Antimicrobial Agents and Chemotherapy, vol. 63, Article ID e01142-19 (2019).
Lane et al., "Repurposing the antimalarial pyronaridine tetraphosphate to protect against Ebola virus infection." PLoS Neglected Tropical Diseases, vol. 13, Article ID e00074890 (2019).
Lane et al., "Toward the Target: Tilorone, Quinacrine, and Pyronaridine Bind to Ebola Virus Glycoprotein." ACS Med Chem Lett, vol. 11, pp. 1653-1658 (2020).
Lee et al., "Anti-Ebola therapy for patients with Ebola virus disease: a systematic review." BMC Infect Dis, vol. 19, p. 376 (2019).
Leligdowicz et al., "Ebola virus disease and critical illness." Crit Care, vol. 20, p. 217 (2016).

(56) References Cited

OTHER PUBLICATIONS

Madelain et al., "Favipiravir Pharmacokinetics in Nonhuman Primates and Insights for Future Efficacy Studies of Hemorrhagic Fever Viruses." Antimicrob Agents Chemother, vol. 61 (2017).
Madrid et al., "A systematic screen of FDA-approved drugs for inhibitors of biological threat agents." PLoS One, vol. 8, Article ID e60579 (2013).
Madrid et al., "Evaluation of Ebola Virus Inhibitors for Drug Repurposing." ACS Infect Dis, vol. 1, pp. 317-326 (2015).
Mankowski et al., "Molecular cloning, expression, and characterization of CYP2D17 from cynomolgus monkey liver." Arch Biochem Biophys, vol. 372, pp. 189-196 (1999).
Martin et al., "Chloroquine transport via the malaria parasite's chloroquine resistance transporter." Science, vol. 325, pp. 1680-1682 (2009).
Miller et al., "Minimal In Vivo Efficacy of Iminosugars in a Lethal Ebola Virus Guinea Pig Model." PLoS One, vol. 11, Article ID e0167018 (2016).
Morris et al., "Pharmacokinetic interaction between pyronaridine-artesunate and metroprolol." Antimicrob Agents Chemother, vol. 58, pp. 5900-5908 (2014).
Mulangu et al., "A Randomized, Controlled Trial of Ebola Virus Disease Therapeutics." N Engl J Med, vol. 381, pp. 2293-2303 (2019).
Oestereich et al., "Successful treatment of advanced Ebola virus infection with T-705 (favipiravir) in a small animal model." Antiviral Res, vol. 105, pp. 17-21 (2014).
Puhl et al. "Repurposing the Ebola and Marburg Virus Inhibitors Tilorone, Quinacrine, and Pyronaridine: In Vitro Activity against SARS-CoV-Z and Potential Mechanisms," ACS Omega, 6, 11, 7454-7468, published online Mar. 10, 2021.
Puhl et al. "Pyronaridine Protects against SARS-CoV-2 Infection in Mouse," ACS Infectious Diseases, 8, 6, 1147-1160, published online May 24, 2022.
Qiu et al., "Reversion of advanced Ebola virus disease in nonhuman primates with ZMapp." Nature, vol. 514, pp. 47-53. (2014).
Quinn et al., "Rho GTPases modulate entry of Ebola virus and vesicular stomatitis virus pseudotyped vectors." J Virol, vol. 83, pp. 10176-10186 (2009).
Rahim et al., "Postexposure Protective Efficacy of T-705 (Favipiravir) Against Sudan Virus Infection in Guinea Pigs." J Infect Dis, vol. 218, pp. S649-S657 (2018).
Ramanathan et al., "A new and simple solid-phase extraction method for LC determination of pyronaridine in human plasma." J Chromatogr B, vol. 824, pp. 45-50 (2005).
Rijal et al., "Therapeutic Monoclonal Antibodies for Ebola Virus infection Derived from Vaccinated Humans." Cell Rep, vol. 27, pp. 172-186 e7 (2019).
Shimada et al., "Cytochrome P450-dependent drug oxidation activities in liver microsomes of various animal species including rats, guinea pigs, dogs, monkeys, and humans." Arch Toxicol, vol. 71, pp. 401-408 (1997).
Siegel et al., "Discovery and Synthesis of a Phosphoramidate Prodrug of a Pyrrolo[2,1-f][triazine-4-amino] Adenine C-Nucleoside (GS-5734) for the Treatment of Ebola and Emerging Viruses." J Med Chem, vol. 60, pp. 1648-1661 (2017).
Sissoko et al., "Experimental treatment with Favipiravir for Ebola Virus Disease (the JIKI Trial): A historically controlled, single-arm proof-of-concept trial in Guinea." PLoS Medicine, vol. 13, Article ID e1001967 (2016).
Sivapalasingam et al., "Safety, pharmacokinetics, and immunogenicity of a co-formulated cocktail of three human monoclonal antibodies targeting Ebola virus glycoprotein in healthy adults: a randomized, first-in-human phase 1 study." Lancet Infect Dis, vol. 18, pp. 884-893 (2018).
Smither et al., "Post-exposure efficacy of oral T-705 (Favipiravir) against inhalational Ebola virus infection in a mouse model." Antiviral Res, vol. 104, pp. 153-155 (2014).
Taylor et al., "BCX44301—A broad-spectrum antiviral adenosine nucleoside analog under development for the treatment of Ebola virus disease." J Infect Public Health, vol. 9, pp. 220-226 (2016).
Twarog et al., "BRAID: A Unifying Paradigm for the Analysis of Combined Drug Action." Sci Rep, vol. 6, Article No. 25523 (2016).
Tyteca et al., "Azithromycin, a lysosomotropic antibiotic, has distinct effects on fluid-phase and receptor mediated endocytosis, but does not impair phagocytosis in J774 macrophages." Exp Cell Res, vol. 281, pp. 86-100 (2002).
Watanabe et al., "Functional importance of the coiled-coil of the Ebola virus glycoprotein." J Virol, vol. 74, pp. 10194-10201 (2000).
Wec et al., "Development of a Human Antibody Cocktail that Deploys Multiple Functions to Confer Pan-Ebolavirus Protection." Cell Host Microbe, vol. 25, pp. 39-48 e5 (2109).
Zhang et al., "The innate immunity of guinea pigs against highly pathogenic avian influenza virus infection." Oncotarget, vol. 8, pp. 30422-30437 (2017).

\* cited by examiner

FIG. 14B

USE OF PYRONARIDINE, TILORONE, AND QUINACRINE AGAINST MARBURG VIRUS AND OTHER VIRUS INFECTIONS

CROSS-REFERENCE TO RELATED APPLICATIONS

This application claims benefit of U.S. Provisional Patent Application Ser. No. 62/931,456, filed Nov. 6, 2019, which is herein incorporated by reference in its entirety.

GOVERNMENT INTEREST

This invention was made with government support under Grant Number R21TR001718 awarded by the National Institutes of Health. The government has certain rights in the invention.

TECHNICAL FIELD

The presently disclosed subject matter relates to the use of pyronaridine, tilorone, and/or quinacrine in treating or preventing diseases caused by viruses, such as Marburg virus, Chikungunya virus, Nipah virus, and coronaviruses.

BACKGROUND

Ebola virus is a virus that is pathogenic against both humans and non-human primates, causing severe hemorrhagic fevers (5) with mortality rates as high as 90%. Recent outbreaks of Ebola virus (EBOV) in Africa have highlighted the need for new antiviral drugs for this and other emerging viruses to counter the human and financial cost (6, 7). For example, the outbreak in Western Africa in 2014-2016 killed over 11,000 and caused over $53 bn in economic damage (8). Overall, there are very few small molecule drugs that have been approved for tropical viral disease.

Accordingly, there is an ongoing need for new methods of treating viral diseases, particularly methods that could involve the use of small molecule antiviral agents that can be easily administered, such as via oral administration.

SUMMARY

The presently disclosed subject matter provides a method of treating or preventing a disease caused by a viral infection in a subject in need of treatment thereof, wherein the viral infection is selected from the group comprising Marburg virus (MARV), Chikungunya virus (CHIKV), norovirus, a coronavirus, and Nipah virus, wherein the method comprises administering to the subject an effective amount of pyronaridine, quinacrine, tilorone, a combination thereof, and/or a pharmaceutically acceptable salt thereof.

In some embodiments, the disease is caused by MARV. In some embodiments, the disease is caused by CHIKV and the method comprises administering tilorone and/or quinacrine or a salt thereof.

In some embodiments, the disease is caused by a coronavirus. In some embodiments, the disease is caused by Middle East Respiratory Syndrome coronavirus (MERS-CoV) and the method comprises administering one or both of pyronaridine and tilorone or a salt thereof.

In some embodiments, the disease is caused by norovirus and the method comprises administering pyronaridine or a salt thereof. In some embodiments, the disease is caused by Nipah virus and the method comprises administering pyronaridine or a salt thereof.

In some embodiments, the administering comprises administering pyronaridine or a salt thereof and further comprises administering artesunate. In some embodiments, the subject is a mammal. In some embodiments, the subject is a human. In some embodiments, the administering is performed via oral administration, intranasal administration, or intravenous administration.

In some embodiments, the presently disclosed subject matter provides a method of treating or preventing a viral infection caused by a virus of the family Filoviridae in a subject in need thereof, wherein the method comprises administering to the subject an effective amount of pyronaridine, quinacrine, tilorone, a combination thereof, and/or a pharmaceutically acceptable salt thereof. In some embodiments, the viral infection is caused by Ebola virus (EBOV) or Marburg virus (MARV). In some embodiments, the method comprises administering pyronaridine or a pharmaceutically acceptable salt thereof. In some embodiments, the method comprises administering quinacrine or a pharmaceutically acceptable salt thereof.

In some embodiments, the presently disclosed subject matter provides a method of treating or preventing a viral infection caused by an alphavirus in a subject in need thereof, wherein the method comprises administering to the subject an effective amount of pyronaridine, quinacrine, tilorone, a combination thereof, and/or a pharmaceutically acceptable salt thereof. In some embodiments, the alphavirus is selected from Chikungunya virus (CHIKV) and Venezuelan Equine Encephalitis Virus (VEEV). In some embodiments, the method comprises administering pyronaridine or a pharmaceutically acceptable salt thereof. In some embodiments, the method comprises administering quinacrine or a pharmaceutically acceptable salt thereof.

Accordingly, it is an object of the presently disclosed subject matter to provide methods of treating or preventing diseases caused by viral infections, such as Marburg virus (MARV), Chikungunya virus (CHIKV), norovirus, Middle East Respiratory Syndrome coronavirus (MERS-CoV), and Nipah virus via administration of compositions comprising pyronaridine, tilorone, and/or quinacrine.

An object of the presently disclosed subject matter having been stated hereinabove, and which is achieved in whole or in part by the presently disclosed subject matter, other objects will become evident as the description proceeds hereinbelow.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 14B is a graph showing Ebola glycoprotein dissociation constant (Kd) values generated using microscale thermophoresis data for pyronaridine (triangles) and toremifene (circles).

DETAILED DESCRIPTION

Figure 1:
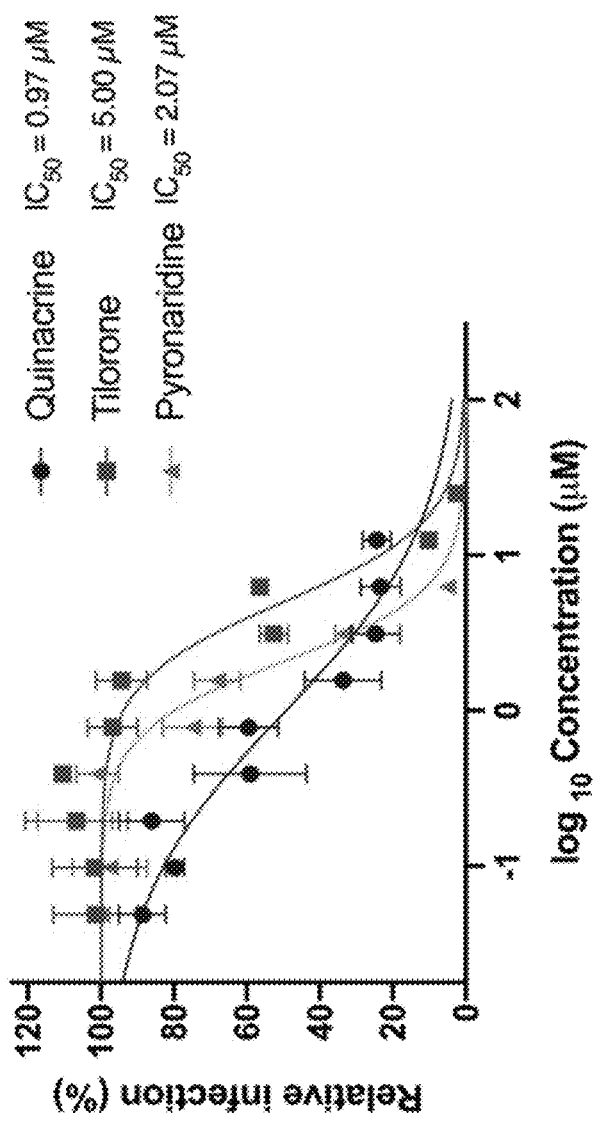
FIG. 1 is a graph showing the ability of quinacrine (circles), tilorone (squares), and pyronaridine (triangles) in inhibiting the Ebola virus Vesicular Stromatitis virus (EBOV-VSV) pseudovirus entry into human (HeLa) cells. The graph shows relative infection percentage (%) as a function of log 10 of the compound concentration (in micromolar (µM)). The 50 percent inhibitory concentrations ($IC_{50}$s) of the three compounds were as follows: 0.97 µM for quinacrine; 5.00 µM for tilorone; and 2.07 µM for pyronaridine.

The presently disclosed subject matter will now be described more fully. The presently disclosed subject matter can, however, be embodied in different forms and should not be construed as limited to the embodiments set forth herein below and in the accompanying Examples. Rather, these embodiments are provided so that this disclosure will be thorough and complete, and will fully convey the scope of the embodiments to those skilled in the art.

All references listed herein, including but not limited to all patents, patent applications and publications thereof, and scientific journal articles, are incorporated herein by reference in their entireties to the extent that they supplement, explain, provide a background for, or teach methodology, techniques, and/or compositions employed herein.

I. Definitions

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs.

Following long-standing patent law convention, the terms "a", "an", and "the" refer to "one or more" when used in this application, including the claims.

The term "and/or" when used in describing two or more items or conditions, refers to situations where all named items or conditions are present or applicable, or to situations wherein only one (or less than all) of the items or conditions is present or applicable.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" can mean at least a second or more.

The term "comprising", which is synonymous with "including," "containing," or "characterized by" is inclusive or open-ended and does not exclude additional, unrecited elements or method steps. "Comprising" is a term of art used in claim language which means that the named elements are essential, but other elements can be added and still form a construct within the scope of the claim.

As used herein, the phrase "consisting of" excludes any element, step, or ingredient not specified in the claim. When the phrase "consists of" appears in a clause of the body of a claim, rather than immediately following the preamble, it limits only the element set forth in that clause; other elements are not excluded from the claim as a whole.

As used herein, the phrase "consisting essentially of" limits the scope of a claim to the specified materials or steps, plus those that do not materially affect the basic and novel characteristic(s) of the claimed subject matter.

With respect to the terms "comprising", "consisting of", and "consisting essentially of", where one of these three terms is used herein, the presently disclosed and claimed subject matter can include the use of either of the other two terms.

Unless otherwise indicated, all numbers expressing quantities of time, concentration, dosage and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about", when referring to a value is meant to encompass variations of in one example ±20% or ±10%, in another example ±5%, in another example ±1%, and in still another example ±0.1% from the specified amount, as such variations are appropriate to perform the disclosed methods.

As use herein, the terms "administration of" and/or "administering" a compound can be understood to refer to providing a compound of the presently disclosed subject matter to a subject in need of treatment. As used herein "administering" includes administration of a compound or compounds by any number of routes and modes including, but not limited to, topical, oral, buccal, intravenous, intramuscular, intra-arterial, intramedullary, intrathecal, intraventricular, transdermal, subcutaneous, intraperitoneal, intranasal, enteral, topical, sublingual, vaginal, ophthalmic, pulmonary, vaginal, and rectal approaches.

As used herein, an "effective amount" or "therapeutically effective amount" refers to an amount of a compound or composition sufficient to produce a selected effect, such as but not limited to alleviating symptoms of a condition, disease, or disorder. In the context of administering compounds in the form of a combination, such as multiple compounds, the amount of each compound, when administered in combination with one or more other compounds, may be different from when that compound is administered alone. Thus, an effective amount of a combination of compounds refers collectively to the combination as a whole, although the actual amounts of each compound may vary. The term "more effective" means that the selected effect occurs to a greater extent by one treatment relative to the second treatment to which it is being compared.

The term "prevent", as used herein, means to stop something from happening, or taking advance measures against something possible or probable from happening. In the context of medicine, "prevention" generally refers to action taken to decrease the chance of getting a disease or condition. It is noted that "prevention" need not be absolute, and thus can occur as a matter of degree.

The terms "treatment" and "treating" as used herein refer to both therapeutic treatment and prophylactic or preventative measures, wherein the object is to prevent or slow down (lessen) the targeted pathologic condition, prevent the pathologic condition, pursue or obtain beneficial results, and/or lower the chances of the individual developing a condition, disease, or disorder, even if the treatment is ultimately unsuccessful. Those in need of treatment include those already with the condition as well as those prone to have or predisposed to having a condition, disease, or disorder, or those in whom the condition is to be prevented. In the context of viral diseases, those in need of treatment include those coming into contact with subject already having or suspected of having a disease caused by the viral infection, those living in or traveling through geographical regions where there are active or prior outbreaks of the viral disease, and any other subjects who have been or could be exposed to the virus (e.g., while doing scientific research on the virus, by coming into contact with virus infected materials (e.g., medical waste) or though the medical or veterinary treatment of others (either humans or other animals) who are known to have or are suspected of having been infected with the virus.

II. General Considerations

The ongoing outbreaks of the Ebola virus (EBOV) in Africa have brought global visibility to the shortage of available therapeutic options to treat patients with this or other viruses. Repurposing drugs for different diseases offers the opportunity to translate a molecule that is approved for one use and potentially accelerate its application and approval for another (1-3). For example, pyronaridine has been described for treating malaria (14). It is a component of the EU-approved antimalarial Pyramax, which is a combination antimalarial therapy with artesunate and pyronaridine and is approved for this use in the Democratic Republic of the Congo.

The presently disclosed subject matter relates, in some aspects, to translating pyronaridine and other clinical stage compounds, e.g., tilorone and quinacrine, rapidly to the clinic as a treatment or preventative agent for diseases caused by viruses such as, but not limited to, filoviruses (e.g., Ebola virus (EBOV) or Marburg virus (MARV)), norovirus, alphaviruses, such as Chikingunya virus (CHIKV) and Venezuelan Equine Encephalitis Virus (VEEV), Nipah virus, arenaviruses (e.g., Tacaribe virus), arboviruses (e.g., Yellow Fever virus), enteroviruses, Dengue virus, influenza viruses, and coronaviruses, such as Middle East Respiratory Syndrome (MERS) virus and Severe Acute Respiratory Syndrome (SARS) coronavirus 2 (SARS-CoV-2). In some embodiments, the virus is MARV, CHIKV, Nipah virus, norovirus, or MERS. The presently disclosed studies with tilorone, quinacrine, and pyronaridine can also provide compounds which could be combined as therapies.

As described in the Examples below, pyronaridine, tilorone, and quinacrine were tested against EBOV and MARV as well as multiple other viruses. More particularly, pyronaridine, tilorone and quinacrine demonstrated statistically significant efficacy in the mouse model of infection with mouse adapted Ebola virus (ma-EBOV). One of these molecules, the antimalarial pyronaridine tetraphosphate demonstrates an $IC_{50}$ range of 0.82-1.30 µM against three strains of EBOV and an $IC_{50}$ range of 1.01-2.72 µM against two strains of Marburg virus (MARV)). Previously, no small molecule drugs have shown statistically significant survival in the guinea pig model of EBOV infection. As described hereinbelow, pharmacokinetics and range-finding studies in guinea pigs found efficacy for a single 300 mg/kg or 600 mg/kg oral dose of pyronaridine 1 hour after infection. A meta-analysis of vehicle controls from four independent studies was performed using oral gavage (n=55). Pyronaridine resulted in statistically significant survival of 40% at 300 mg/kg and protected from a lethal challenge with EBOV. In comparison, oral favipiravir (300 mg/kg dosed once a day) had 43.5% survival. The in vitro metabolism and metabolite identification of pyronaridine and tilorone suggests species differences. In summary, the presently disclosed in vitro and in vivo studies with pyronaridine in the guinea pig model demonstrates its utility for repurposing it, as well as tilorone and quinacrine, as an antiviral against EBOV, MARV virus and other viruses.

For instance, these three compounds were tested in various cell lines (VeroE6, Vero76, Caco-2, Calu-3, A549-ACE2, HUH-7 and monocytes) infected with the coronavirus SARS-CoV-2, the causative agent of COVID-19, as well as other coronaviruses, including the group 2 coronavirus murine hepatitis virus (MHV). They were also tested against pseudovirus and via microscale thermophoresis to test the binding of the compounds to spike protein. While there was variability in antiviral activity across cell lines, it was found that tilorone and pyronaridine inhibited the SARS-CoV-2 in A549-ACE2 cells with $IC_{50}$ values of 180 nM and $IC_{50}$ 198 nM, respectively. They also bind to Spike receptor binding domain (RBD) protein with $K_d$ values of 339 nM and 647 nM, respectively. The human $C_{max}$ for pyronaridine and quinacrine is greater than the $IC_{50}$ obtained in human clinical studies testing these compounds against other diseases.

Accordingly, in some embodiments, the presently disclosed subject matter provides a method of treating or preventing a disease caused by a viral infection in a subject in need of treatment thereof, wherein the method comprises administering a compound selected from pyronaridine, quinacrine, tilorone, or a combination and/or pharmaceutically acceptable salt thereof. In some embodiments, the virus of the viral infection is selected from the group including, but not limited to filoviruses, such as Ebola virus (EBOV) or Marburg virus (MARV); alphaviruses, such as, but not limited to Chikungunya virus (CHIKV) and Venezuelan Equine Encephalitis Virus (VEEV); norovirus; a coronavirus (e.g., a betacoronavirus such as Middle East Respiratory Syndrome coronavirus (MERS-CoV) or Severe Acute Respiratory Syndrome coronavirus 2 (SARS-CoV-2), and Nipah virus, wherein the method comprises administering to the subject an effective amount of pyronaridine, quinacrine, tilorone, a combination thereof, and/or a pharmaceutically acceptable salt thereof.

In some embodiments, the disease is caused by MARV. In some embodiments, the disease is caused by a viral infection of MARV, strain Angola. In some embodiments, the disease is caused by a viral infection of MARV, strain Musoke.

In some embodiments, the disease is caused by CHIKV. In some embodiments, the method of treating or preventing CHIKV comprises administering tilorone and/or quinacrine or a salt or salts thereof.

In some embodiments, the disease is caused by a coronavirus. In some embodiments, the coronavirus is MERS-CoV. In some embodiments, the coronavirus is MERS-CoV and the method comprises administering one or both of pyronaridine and tilorone or a salt or salts thereof. In some embodiments, the method comprises administering tilorone or a salt thereof. In some embodiments, the coronavirus is SARS-CoV-2. In some embodiments, the coronavirus is SARS-CoV-2 and the method comprises administering quinacrine.

In some embodiments, the disease is caused by norovirus. In some embodiments, the method of treating or preventing a disease caused by norovirus comprises administering pyronaridine or a salt thereof.

In some embodiments, the disease is caused by Nipah virus. In some embodiments, the method of treating or preventing the disease caused by Nipah virus comprises administering pyronaridine or a salt thereof.

In some embodiments, the method comprises administering pyronaridine or a salt thereof (e.g., pyronaridine tetraphosphate). In some embodiments, the method further comprises administering artesunate.

The subject in need of treatment can be any subject. In some embodiments, the subject is a mammal. In some embodiments, the subject is a human. In some embodiments, the subject is a non-human primate. In some embodiments, the subject is livestock, e.g., horses, cattle, pigs, sheep, goats, donkeys, chickens, geese, etc.

The administering can be via any suitable route. In some embodiments, the administering is via oral administration. In some embodiments, the administering is performed via intranasal administration. In some embodiments, the administration is via intravenous administration.

In some embodiments, the presently disclosed subject matter provides a method of treating or preventing a viral infection caused by a virus of the family Filoviridae in a subject in need thereof, wherein the method comprises administering to the subject an effective amount of pyronaridine, quinacrine, tilorone, a combination thereof, and/or a pharmaceutically acceptable salt thereof. For example, the viral infection can be caused by an Ebola virus, e.g., of the Mayinga, Makona, or Kikwit strain. In some embodiments, the viral infection is caused by Marburg virus (MARV), e.g., of the Angola or Musoke strain.

In some embodiments, the method comprises administering pyronaridine or a pharmaceutically acceptable salt thereof (e.g., pyronaridine tetraphosphate). In some embodiments, the method comprises administering quinacrine or a pharmaceutically acceptable salt thereof (e.g., quinacrine dihydrochloride). In some embodiments, the method comprises administering a combination of at least two of pyronaridine, quinacrine and tilorone.

In some embodiments, the presently disclosed subject matter provides a method of treating or preventing a viral infection caused by an alphavirus in a subject in need thereof, wherein the method comprises administering to the subject an effective amount of pyronaridine, quinacrine, tilorone, a combination thereof, and/or a pharmaceutically acceptable salt thereof. In some embodiments, the alphavirus is CHIKV. In some embodiments, the alphavirus is VEEV.

In some embodiments, the method comprises administering pyronaridine or a pharmaceutically acceptable salt thereof (e.g., pyronaridine tetraphosphate). In some embodiments, the method comprises administering quinacrine or a pharmaceutically acceptable salt thereof (e.g., quinacrine dihydrochloride). In some embodiments, the method comprises administering a combination of at least two of pyronaridine, quinacrine and tilorone.

III. Pharmaceutically Acceptable Salts and Compositions

As noted above, in some embodiments, the active compounds of the presently disclosed subject matter (e.g., pyronaridine, tilorone, and quinacrine) can be provided as pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts, and combinations thereof.

Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like.

Base addition salts include but are not limited to, ethylenediamine, N-methyl-glucamine, lysine, arginine, ornithine, choline, N, N'-dibenzylethylenediamine, chloroprocaine, diethanolamine, procaine, N-benzylphenethylamine, diethylamine, piperazine, tris (hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like.

Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

In some embodiments, the presently disclosed compounds can further be provided as a solvate.

The active compounds can be used on a sample either in vitro (for example, on isolated cells or tissues) or in vivo in a subject (i.e. living organism, such as a patient). In some embodiments, the subject or patient is a human subject, although it is to be understood that the principles of the presently disclosed subject matter indicate that the presently disclosed subject matter is effective with respect to all vertebrate species, including mammals, which are intended to be included in the terms "subject" and "patient". Moreover, a mammal is understood to include any mammalian species for which employing the compositions and methods disclosed herein is desirable, particularly agricultural and domestic mammalian species.

As such, the methods of the presently disclosed subject matter are particularly useful in warm-blooded vertebrates. Thus, the presently disclosed subject matter concerns mammals and birds. More particularly provided are methods and compositions for mammals such as humans and non-human primates, as well as other mammals of importance due to being endangered (such as Siberian tigers), of economic importance (animals raised on farms for consumption by humans), and/or of social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also provided is the treatment of birds, including the treatment of those kinds of birds that are endangered, kept in zoos or as pets (e.g., parrots), as well as fowl, and more particularly domesticated fowl, for example, poultry, such as turkeys, chickens, ducks, geese, guinea fowl, and the like, as they are also of economic importance to humans. Thus, also provided is the treatment of livestock including, but not limited to domesticated swine (pigs and hogs), ruminants, horses, poultry, and the like.

In some embodiments, the active compounds can include more than one of the active compounds described herein or can include one or more of the active compounds and one or more additional therapeutic agents. Thus, in some embodiments, the active compound or compounds can be administered along with one or more additional therapeutic agents known in the art for treating a disease or disorder associated with a viral infection or a symptom thereof. For example, the compounds can be co-administered with an antiviral compound that is not pyronaridine, quinacrine or tilorone or with a therapeutic agent useful in treating a symptom of a viral infection (e.g., pain, fever, headache, stuffy/runny nose, cough, inflammation, etc.). The active compounds and the one or more additional therapeutic agents can be provided in a single formulation or co-administered in separate formulations at about the same time or at different times (e.g., different times within the same day, week, or month).

In some embodiments, the active compound of the presently disclosed subject matter can be administered in a pharmaceutically acceptable composition where the compound can be admixed with one or more pharmaceutically acceptable carriers. The term "pharmaceutically acceptable carrier" means a non-toxic material that does not interfere with the effectiveness of the biological activity of the active ingredients. In some embodiments, the pharmaceutically acceptable composition can also contain salts, buffering agents, preservatives, compatible carriers, and optionally other therapeutic agents.

Suitable methods for administration of an active compound or pharmaceutically acceptable composition thereof to a subject include, but are not limited to intravenous injection, oral administration, buccal, topical, subcutaneous administration, intraperitoneal injection, pulmonary, intranasal, intracranial injection, and rectal administration. The particular mode of administering a composition matter depends on various factors, including the distribution and abundance of cells to be treated and mechanisms for metabolism or removal of the composition from its site of administration.

An effective dose of a composition of the presently disclosed subject matter is administered to a subject. An "effective amount" is an amount of the composition sufficient to produce detectable treatment. Actual dosage levels of constituents of the compositions of the presently disclosed subject matter can be varied so as to administer an amount of the composition that is effective to achieve the desired effect for a particular subject and/or target. The selected dosage level can depend upon the activity of the composition and the route of administration. In some embodiments, the active compounds can be used in dosages from 0.001-1000 mg/kg body weight.

After review of the disclosure herein of the presently disclosed subject matter, one of ordinary skill in the art can tailor the dosages to an individual subject, taking into account the particular formulation, method of administration to be used with the composition, and nature of the target to be treated. Such adjustments or variations, as well as evaluation of when and how to make such adjustments or variations, are well known to those of ordinary skill in the art.

The therapeutically effective amount can be determined by testing the compounds in an in vitro or in vivo model and then extrapolating therefrom for dosages in subjects of interest, e.g., humans. The therapeutically effective amount should be enough to exert a therapeutically useful effect in the absence of undesirable side effects in the subject to be treated with the composition.

Pharmaceutically acceptable carriers are well known to those skilled in the art and include, but are not limited to, from about 0.01 to about 0.1M and preferably 0.05M phosphate buffer or 0.8% saline. Such pharmaceutically acceptable carriers can be aqueous or non-aqueous solutions, suspensions and emulsions. Examples of non-aqueous solvents suitable for use in the presently disclosed subject matter include, but are not limited to, propylene glycol, polyethylene glycol, vegetable oils such as olive oil, and injectable organic esters such as ethyl oleate. Aqueous carriers suitable for use in the presently disclosed subject matter include, but are not limited to, water, ethanol, alcoholic/aqueous solutions, glycerol, emulsions or suspensions, including saline and buffered media. Oral carriers can be elixirs, syrups, capsules, tablets and the like.

Liquid carriers suitable for use in the presently disclosed subject matter can be used in preparing solutions, suspensions, emulsions, syrups, elixirs and pressurized compounds. The active ingredient can be dissolved or suspended in a pharmaceutically acceptable liquid carrier such as water, an organic solvent, a mixture of both or pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers or osmo-regulators.

Liquid carriers suitable for use in the presently disclosed subject matter include, but are not limited to, water (partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and *arachis* oil). For parenteral administration, the carrier can also include an oily ester such as ethyl oleate and isopropyl myristate. Sterile liquid carriers are useful in sterile liquid form comprising compounds for parenteral administration. The liquid carrier for pressurized compounds disclosed herein can be halogenated hydrocarbon or other pharmaceutically acceptable propellant.

Solid carriers suitable for use in the presently disclosed subject matter include, but are not limited to, inert substances such as lactose, starch, glucose, methyl-cellulose, magnesium stearate, dicalcium phosphate, mannitol and the like. A solid carrier can further include one or more substances acting as flavoring agents, lubricants, solubilizers, suspending agents, fillers, glidants, compression aids, binders or tablet-disintegrating agents; it can also be an encapsulating material. In powders, the carrier can be a finely divided solid which is in admixture with the finely divided active compound. In tablets, the active compound is mixed with a carrier having the necessary compression properties in suitable proportions and compacted in the shape and size desired. The powders and tablets preferably contain up to 99% of the active compound. Suitable solid carriers include, for example, calcium phosphate, magnesium stearate, talc, sugars, lactose, dextrin, starch, gelatin, cellulose, polyvinylpyrrolidine, low melting waxes and ion exchange resins.

Parenteral carriers suitable for use in the presently disclosed subject matter include, but are not limited to, sodium chloride solution, Ringer's dextrose, dextrose and sodium chloride, lactated Ringer's and fixed oils. Intravenous carriers include fluid and nutrient replenishers, electrolyte replenishers such as those based on Ringer's dextrose and the like. Preservatives and other additives can also be present, such as, for example, antimicrobials, antioxidants, chelating agents, inert gases and the like.

Carriers suitable for use in the presently disclosed subject matter can be mixed as needed with disintegrants, diluents, granulating agents, lubricants, binders and the like using conventional techniques known in the art. The carriers can also be sterilized using methods that do not deleteriously react with the compounds, as is generally known in the art. The compounds disclosed herein can take such forms as suspensions, solutions or emulsions in oily or aqueous vehicles, and can contain formulatory agents such as suspending, stabilizing and/or dispersing agents. The compounds disclosed herein can also be formulated as a preparation for implantation or injection. Thus, for example, the compounds can be formulated with suitable polymeric or hydrophobic materials (e.g., as an emulsion in an acceptable oil) or ion exchange resins, or as sparingly soluble derivatives (e.g., as a sparingly soluble salt). Alternatively, the active ingredient can be in powder form for constitution with a suitable vehicle, e.g., sterile pyrogen-free water, before use. Suitable formulations for each of these methods of administration can be found, for example, in *Remington: The Science and Practice of Pharmacy*, A. Gennaro, ed., 20th edition, Lippincott, Williams & Wilkins, Philadelphia, Pa.

For example, formulations for parenteral administration can contain as common excipients sterile water or saline, polyalkylene glycols such as polyethylene glycol, oils of vegetable origin, hydrogenated naphthalenes and the like. In particular, biocompatible, biodegradable lactide polymer, lactide/glycolide copolymer, or polyoxyethylene-polyoxypropylene copolymers can be useful excipients to control the release of active compounds. Other potentially useful parenteral delivery systems include ethylene-vinyl acetate copolymer particles, osmotic pumps, implantable infusion systems, and liposomes. Formulations for inhalation administration contain as excipients, for example, lactose, or can be aqueous solutions containing, for example, polyoxyethylene-9-auryl ether, glycocholate and deoxycholate, or oily solutions for administration in the form of nasal drops, or as a gel to be applied intranasally. Formulations for parenteral administration can also include glycocholate for buccal administration, methoxysalicylate for rectal administration, or citric acid for vaginal administration.

Further, formulations for intravenous administration can comprise solutions in sterile isotonic aqueous buffer. Where necessary, the formulations can also include a solubilizing agent and a local anesthetic to ease pain at the site of the injection. Generally, the ingredients are supplied either separately or mixed together in unit dosage form, for example, as a dry lyophilized powder or water free concentrate in a hermetically sealed container such as an ampule or sachet indicating the quantity of active agent. Where the compound is to be administered by infusion, it can be dispensed in a formulation with an infusion bottle containing sterile pharmaceutical grade water, saline or dextrose/water. Where the compound is administered by injection, an ampule of sterile water for injection or saline can be provided so that the ingredients can be mixed prior to administration.

Suitable formulations further include aqueous and non-aqueous sterile injection solutions that can contain antioxidants, buffers, bacteriostats, bactericidal antibiotics and solutes that render the formulation isotonic with the bodily fluids of the intended recipient; and aqueous and non-aqueous sterile suspensions, which can include suspending agents and thickening agents.

The compounds can further be formulated for topical administration. Suitable topical formulations include one or more compounds in the form of a liquid, lotion, cream or gel. Topical administration can be accomplished by application directly on the treatment area. For example, such application can be accomplished by rubbing the formulation (such as a lotion or gel) onto the skin of the treatment area, or by spray application of a liquid formulation onto the treatment area.

In some formulations, bioimplant materials can be coated with the compounds so as to improve interaction between cells and the implant.

Formulations of the compounds can contain minor amounts of wetting or emulsifying agents, or pH buffering agents. The formulations comprising the compound can be a liquid solution, suspension, emulsion, tablet, pill, capsule, sustained release formulation, or powder. The compounds can be formulated as a suppository, with traditional binders and carriers such as triglycerides.

Oral formulations can include standard carriers such as pharmaceutical grades of mannitol, lactose, starch, magnesium stearate, polyvinyl pyrollidone, sodium saccharine, cellulose, magnesium carbonate, etc.

In some embodiments, the pharmaceutical composition comprising the active compound or compounds of the presently disclosed subject matter can include an agent which controls release of the compound, thereby providing a timed or sustained release compound.

EXAMPLES

The following Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

Materials and Methods

Chemicals and Reagents:

Pyronaridine tetraphosphate [4-[(7-Chloro-2-methoxybenzo[b][1,5]naph-thyridin-10-yl)amino]-2,6-bis(1-pyrrolidinylmethyl)phenol phosphate (1:4)] (11) was purchased from BOC Sciences (Shirley, N.Y., United States of America). Favipiravir was purchased from AdooQ Bioscience (Irvine, Calif., United States of America). Tilorone and pyronaridine was purchased from BOC Sciences. Quinacrine and Chloroquine were purchased from Cayman Chemicals (Ann Arbor, Mich., United States of America) and Sigma Aldrich (St. Louis, Mo., United States of America), respectively.

Test Article Preparation for In Vivo Studies:

Vehicle Preparation: (Pyronardine study): A solution of 20% of the solubilizer/emulsifier sold under the tradename KOLLIPHOR™ HS 15 (BASF SE, Ludwigshafen am Rhein, Germany) with Water for injection (WFI) was made to be used for the vehicle. The solubilizer/emulsifier was melted at 60° C. 10 ml of the solubilizer/emulsifier was combined with WFI to a final solution volume of 50.0 ml (20% solution) and mixed using a vortex mixer for 30 seconds and then sonicated in an ultrasonic water bath for 25 minutes at 45° C.

Test Article Dose Preparation: Dose formulations were prepared by mixing the pyronaridine in the vehicle to achieve the target concentration. The formulation was mixed by inversion 5-6 times and placed on an orbital shaker for 30±5 min.

Favipiravir Preparation: A 0.5% solution of methylcellulose was prepared in sterile water. To this, the appropriate amount of Favipiravir was added and the pH adjusted until the compound goes into solution. Favipiravir was prepared prior to challenge and stored at 4-8° C.

Liver Microsome Stability Assays:

The liver microsome solution (197.5 µL, 0.5 mg/ml protein concentration) was aliquoted into 1.1 ml tubes, to which 2.5 µL of positive control and tilorone stock solutions (100 µM in dimethyl sulfoxide (DMSO)) were added. The tubes were vortexed gently, pre-incubated for 5 min at 37° C., then 50 µL of 5 mM NADPH or LM buffer (no NADPH buffer) was added into the tubes. For analysis, an aliquot of 30 µL was removed from each tube at 0, 5, 15, 30 and 60 min (without-NADPH reaction: 0 and 60 min) and quenched with 300 µL of 5/10 ng/ml terfenadine/tolbutamide in methanol/acetonitrile (1:1, v/v). Samples were vigorously vortexed for 1 min and then centrifuged at 4,000 rpm for 15 min at 4° C. 100 µL of supernatant from each sample was transferred to tubes for liquid chromatography-mass spectrometry (LCMS) analysis. The amount of parent compound was determined on the basis of the peak area ratio (compound area to IS area) for each time point (using a spectrometer sold under the tradename AB SCIEX™ 4500 (Life Technologies Corporation, Carlsbad, Calif., United States of America). Clearance rates were calculated by the equation: $t1/2=Ln(2)/ke$ and in vitro $CL_{int}$ (µL/min/mg protein) =ke*Incubation volume/Microsomal protein amount, and ke using equation of 1st order kinetics:

$$C_t = C_0 \times e^{-ke \cdot t}$$

In Vitro Metabolite Identification of Pyronaridine, Quinacrine, Chloroquine and Tilorone in Human, Mouse, Guinea Pig Liver Microsomes:

A DMSO solution of test compound was spiked into 50 mM $KH_2PO_4$ (pH 7.4) buffer containing liver microsome at a concentration of 1 mg/mL. The reaction was initiated by the addition of 1.0 mM NADPH to the reaction mixture. The final concentration of the test compound was 1 µM. After 0 min and 60 min incubation at 37° C., an aliquot was removed and the sample were precipitated with a 1:6 acetonitrile, quenching the reaction. The resulting mixture was centrifuged and the resultant supernatants were dried at $N_2$ stream, the resultant residue were reconstituted with 300 µL 10% acetonitrile/$H_2O$ (v/v) (0.1% FA) before LC-MS/MS analysis. The supernatant was used for LC-MS/MS analysis. All separations were performed on an HPLC column sold under the tradename ACQUITY™ UPLC BEH T3 1.8 µm column (2.1×100 mm; Waters Corporation, Milford, Mass., United States of America) at 25° C. with a flow rate of 0.3 mL/min. Mobile phase A consisted of 0.1% formic acid in water and mobile phase B consisted of 0.1% formic acid in acetonitrile. Chromatography used a step gradient by maintaining 1% mobile phase B for 5 min, 10% mobile phase B over 8.0 minutes, 20% mobile phase B over 2.0 min, 90% mobile phase B over 2 minutes, 95% mobile phase B over 2 minutes, then re-equilibration back to 1% B at 20 minutes. The total run time was 22 minutes. For all samples, a 5 µL aliquot of sample was injected. The mass spectrometer (high resolution mass spectrometry (HRMS), Q-Exactive Plus from Thermo Fisher Scientific, Waltham, Mass., United States of America) was operated in high-resolution, accurate-mass (HRAM) detection mode with a mass analyzer sold under the tradename ORBITRAP™ (Thermo Finnigan, LLC, San Jose, Calif., United States of America).

Guinea Pig Dose Range-Finding Toxicity for Pyronaridine:

To assess the tolerance of pyronaridine and to select dose groups for pharmacokinetics studies, the drug was given to 5-6-week-old male and female Hartley guinea pigs (Vital River Laboratories, Beijing, China) as a single dose by intraperitoneal (i.p.) administration or oral gavage (PO). The compound was formulated in 20% of a solubilizer/emulsifier sold under the tradename KOLLIPHOR™ HS 15 (BASF SE, Ludwigshafen am Rhein, Germany) in sterile water. There were 8 groups in total (i.p. and oral control groups), with 6 animals per group (3 male, 3 female). I.p. administration was 125, 200 and 300 mg/kg and oral was 125, 300 and 600 mg/kg, each with a dosing volume of 5 ml/kg. Clinical observations were initiated immediately post-dose and once daily up to 168 hours post-dose.

Guinea Pig Pharmacokinetics Evaluation of Pyronaridine:

Guided by the dose range-finding study, the pharmacokinetics of pyronaridine in guinea pigs were initially assessed at 125 and 600 mg/kg (n=3; male) for i.p. and oral administration, respectively, concentrations at or below the maximum tolerated dose (MTD) determined by the 7-day study. Pyronaridine for both oral and i.p. administration was solubilized in the same vehicle (20% of the solubilizer/emulsifier sold under the tradename KOLLIPHOR™ HS 15 (BASF SE, Ludwigshafen am Rhein, Germany). Blood was collected from the treated Guinea pigs at 1, 4, 8, 24, 72, 168, 264, and 336 hours post-dose for processing of plasma. All samples were analyzed, and drug levels were measured by liquid chromatography-tandem mass spectrometry (LC-MS/MS) with a lower limit of quantitation (LLOQ) of 1.0 ng/mL. Notably, in the pyronaridine i.p. dosed, 125 mg/ml group 2 of 3 Guinea pigs were found dead on days 14 and 17 post dose.

Virus Strains:

For in vivo experiments, a well-characterized guinea pig-adapted Ebola virus stock (Ebola virus Cavia porcellus/ COD/1976/Mayinga-CDC-808012 (gpaEBOV)) was used for all efficacy studies (37).

Initial Cell-Based Testing for Inhibition Against Wild Type Marburg Virus Strain:

MARV expressing green fluorescent protein (GFP) was used in testing against viral inhibition as outlined previously (15). In short, inhibitors were tested at 8 concentrations for activity. All treatments were done in duplicates, each replicate being on a different plate. Briefly, 4,000 HeLa cells per well in 25 µl of medium were grown overnight in 384-well tissue culture plates. On the day of assay, test compounds were diluted to 200 µM concentration in complete medium. 25 µl of this mixture was added to the cells already containing 25 µl medium to achieve a concentration of 100 µM. 25 µl of medium was removed from the first wells and added to next well. This type of serial dilution was done 8 times to achieve concentrations of 100, 50, 25, 12.50, 6.25, 3.12, 1.56 and 0.78 µM. One hour after incubating with the compound 25 µl of infection mix containing wild type virus was used to infect cells. This resulted in a final concentration of 50, 25, 12.50, 6.25, 3.12, 1.56, 0.78 and 0.39 µM. Bafilomycin at final a concentration of 10 nM was used as a positive control drug. All virus infections were done in a biosafety level 4 (BSL-4) lab to achieve a multiplicity of infection (MOI) of 0.075 to 0.15. Cells were incubated with virus for 24 hours. One day post infection cells were fixed by immersing the plates in formalin overnight at 4° C. Fixed plates were decontaminated and brought out of the BSL-4. Formalin from fixed plates was decanted and plates were washed thrice with PBS. MARV infected plates were immuno-stained using virus specific antibodies. Nuclei were stained using Hoechst at 1:50,000 dilutions. Plates were imaged and nuclei and infected cells were counted using Cell Profiler software.

Cells were permeabilized using 0.1% Triton X-100 ($C_{at}$ #T8787; Sigma, St. Louis, Mo., United States of America) in PBS and blocked for 1 h in 3.5% bovine serum albumin (Cat #BP9704100, Thermo Fisher Scientific, Waltham, Mass., United States of America), followed by immunostaining. Fixed cells were incubated with an anti-MARV VLP antibody (Cat #04-0005, 1:1500 dilution, IBT Bioservices, Rockville, Md., United States of America), overnight at 4° C. After 2 washes to remove any excess antibody cells were stained with anti-Rabbit Alexa-546 antibody (Life technologies, Cat #A11035). After 3 washes to remove any non-specific antibody nuclei were stained using Hoechst at 1:50,000 dilution and imaged on a Nikon Ti Eclipse automated microscope (Nikon Corporation, Tokyo, Japan). Nuclei and infected cells were counted using CellProfiler software. Relative infection compared to untreated controls was plotted in GraphPad prism 8.2.1 software (GraphPad Software, Inc., La Jolla, Calif., United States of America).

Follow-Up Cell-Based Testing Against Ebola and Marburg Virus Strains:

Compounds were tested in vitro against 3 strains of Ebola virus (Kikwit, Makona, Mayinga) and 2 strains of Marburg virus (Angola, Musoke): Ebola virus/H.sapiens-tc/GIN/ 2014/Makona-005 (EBOV/Mak, GenBank accession no. KX000398.1), Ebola virus/H.sapiens-tc/COD/1995/Kikwit-9510621 (EBOV/Kik, GenBank accession no. KU182905.1); Ebola virus/H.sapiens-tc/COD/1976/Yambuku-Mayinga (EBOV/May, GenBank accession no. KY425649.1); Marburg virus/H.sapiens-tc/AGO/2005/ Ang-1379v (MARV/Ang, BioSample accession no. SAMN05916381); Marburg virus/H.sapiens-tc/KEN/1980/ Mt. Elgon-Musoke (MARV/Mus, GenBank accession no. DQ217792). All virus stocks were propagated, and titers were determined by plaque assay on Vero E6 cells as previously described (38).

The in vitro infection inhibition of the all the above filovirus strains was performed in HeLa cells. HeLa cells were seeded at $3 \times 10^4$ cells/well in 96-well plates. After 24 hours (h), cells were treated with drugs at 2-fold dilutions starting from 30 µM. Cells were infected with virus 1 hr after the addition of the drugs in BSL4-containment at a multiplicity of infection (MOI) of 0.21 or 0.4. After 48 h, plates were fixed and virus was detected with a mouse antibody specific for EBOV VP40 protein (#B-MD04-BD07-AE11, US Army Medical Research Institute of Infectious Diseases, Frederick, Md., United States of America) (38) or MARV VP40 protein (Cat #IBT0203-012, IBT Bioservices, Rockville, Md., United States of America) followed by staining with anti-mouse IgG-peroxidase labeled antibody (#074-1802, KPL, Gaithersburg, Md., United States of America). Luminescence was read on an Infinite® M1000 Pro plate reader (Tecan US, Morrisville, N.C., United States of America). The signal of treated, infected wells was normalized to uninfected control wells and measured (in percent) relative to untreated infected wells. Non-linear regression analysis was performed, and the 50% inhibitory concentrations ($EC_{50}$s) were calculated from fitted curves (log [agonist] versus response [variable slope] with constraint to remain above 0%) (GraphPad Software, Inc., La Jolla, Calif., United States of America). Error bars of dose-response curves represent the standard deviation of three replicates. For quantitation of drug toxicity, HeLa cells were mock infected (no virus) and treated with drug dilutions under the same conditions as the infected cells. After 48 h, cell viability was measured using a cell viability assay kit sold under the tradename CELLTITER-GLO™ Luminescent Cell Viability Assay kit (Promega Corporation, Madison, Wis., United States of America) according to manufacturer's protocol.

VSV-EBOV-GP Psuedotype Virus Assay:

Vesicular Stomatitis Virus (VSV) pseudotyped with EBOV glycoprotein expressing a GFP reporter has been described previously (39,40). Vesicular Stomatitis Virus (VSV) pseudotyped with EBOV glycoprotein was grown by infecting Vero cells and then harvesting via filtration of the supernatant through 0.4 µM filters 24-30 hours after infection. Virus was then stored at −80 until use.

The cells were tested and imaged using the general methods outlined previously (15). In short, HeLa cells were plated at a density of 20,000 cells/well of a 96 well plate. After attachment overnight, cells were pretreated with compounds for 1 hr at predetermined doses. The dosing series in this case was 25, 12.5, 6.25, 3.12, 1.56, 0.78, 0.39, 0.19, 0.09, 0.04, 0.02 and 0.01 µM. After 1 hr of incubation with compounds, the cells were infected with Vesicular Stomatitis Virus (VSV) pseudotyped with EBOV glycoprotein and expressing a GFP reporter. 24 hours after infection, cells were fixed in formalin. After fixation, formalin was washed off, nuclei stained with Hoechst and the cells imaged. Green cells (infected) and blue nuclei (total number of cells) were counted using cell profiler. Relative infection compared to untreated controls was plotted in GraphPad prism 8.2.1 software (GraphPad Software Corporation, La Jolla, Calif., United States of America).

In Vivo Efficacy Clinical Observations and Scoring:

Twenty-four (24) experimentally naïve Hartley guinea pigs were assigned to four (4) gender balanced groups. Guinea pigs were anesthetized for dosing (challenge and treatment) via isoflurane inhalation. On study day 0 (SD0) all guinea pigs were challenged with 1000 PFU of gpa-EBOV in 0.2 mL of Minimum Essential Medium (MEM) via intraperitoneal (i.p.) injection. The viral dose administered was verified through plaque assay analysis of the prepared virus suspension.

Dosing for all pyronaridine and all tilorone groups occurred via oral gavage of test/control article on SD0 one hour (±15 minutes) post-challenge. Favipiravir (300 mg/kg) was given by oral gavage once daily from SD0 through SD7. For the pyronaridine study on SD 3 and during unscheduled euthanasia blood was collected via retro-orbital bleed. For the tilorone study, blood was collected during unscheduled and unscheduled euthanasia. Serum was harvested for viremia measurements via plaque assay.

Following challenge, animals were monitored daily by visual examination. Clinical scoring and health assessments were performed and documented at each observation using the scoring system wherein: 1=Healthy; 2=Lethargic and ruffled fur, 3=Sore of 2+hunched posture an orbital tightening, 4=Score of 3+reluctance to move when stimulated, paralysis, unable to access feed and water normally or ≥20% body weight loss. Body weights were measured daily during the dosing period (SD0-SD7) and then every third day until the study was completed. When animals reached a clinical score of 2, the frequency of clinical observations increased to twice daily, 4-6 hours after the initial observation. When the disease progressed, and the clinical score increased to a 3, the frequency of observations was increased to three times daily. All surviving animals were humanely euthanized on Study Day 21.

Viral Load Determination:

Serum was harvested from guinea pigs (3 male and 3 female) from each group on SD3 in the pyronaridine study. When possible, serum was also harvested from guinea pigs that met the euthanasia criteria. Serum harvested for plaque assay analysis was stored frozen (in an ultralow [i.e., −80° C.] freezer) until the conclusion of the in-life portion of the animal study, after which samples were batch processed. For this assay, the limit of detection in this assay was 100 PFU/mL. For statistical analysis and graphing all values less than the LOD were assigned a value of one half the LOD.

Guinea Pig Dose Range-Finding Toxicity (Tilorone):

To assess the tolerance of tilorone and to select dose groups for pharmacokinetics studies, the drug was given to 25 male/25 female, 5-6-week-old Hartley guinea pigs (Charles River Laboratories, Wilmington, Mass., United States of America) as once daily administration for 7 days via oral gavage (PO). Group 3 animals were dosed daily on Days 1 through 4, Group 4 animals were dosed on Days 1 and 2, and dosing for these groups was terminated early due to mortality and severe clinical signs. The compound was formulated in 0.5% CMC in sterile water for injection. There were 5 groups in total, with 10 animals per group (5 male, 5 female). Dosing was 30, 100, 200/150 and 60 mg/kg and vehicle, each with a dosing volume of 10 ml/kg. Clinical observations were recorded once daily and approximately 2-4 hours post-dose on treatment days and on the day of necropsy. Animals were examined for any altered clinical signs, including gross motor and behavioral activity, and observable changes in appearance.

Guinea Pig Pharmacokinetics Evaluation of Tilorone:

The pharmacokinetics of tilorone in guinea pigs were assessed at 30, 100, 200/150 with 24 animals in each group (12 male/12 female). Blood was collected from the first 6 animals/sex/time point and were sacrificed after their final blood collection. An additional group administered 60 mg/kg had 10 animals (5 male/5 female) and was dosed for 7 days. Male and female guinea pigs received daily administrations of vehicle control (0.5% methylcellulose, Groups 1), tilorone at 30 (Group 2), 100 (Group 3), 200/150 (Group 4) and 60 mg/kg (Group 5) by oral gavage (po). Animals in Groups 1, 2 and 5 received tilorone for 7 days. Group 3 animals received 100 mg/kg for 3 days and then dosing was discontinued by Day 4 due to mortality or moribund condition. Group 4 animals received 200 mg/kg on Day 1,150 mg/kg on Day 2 and then dosing was discontinued due to mortality or moribund condition. Blood was collected from the treated guinea pigs at 0.5, 1, 2, 4, 8, and 24 hours post-dose for processing of plasma. All samples were analyzed, and drug levels were measured by liquid chromatography-tandem mass spectrometry (LC-MS/MS) with a lower limit of quantitation (LLOQ) of 1.0 ng/mL.

Test Article Preparation for In Vivo Studies (Tilorone):

Vehicle Preparation (Tilorone study): An appropriate amount of methylcellulose (0.5% weight to final volume) was added to stirring, preheated, (70±3° C.) sterile water (30% of final volume) and the mixture will be stirred for 10±5 min until all solid is thoroughly wetted and evenly dispersed. Sterile water was then added to the final volume and the solution was stirred at room temperature for 6 hr (±30 min). The vehicle was prepared prior to the start of the study and stored at 4-8° C.

Test Article Dose Preparation: Dose formulations will be prepared by mixing the appropriate amount of tilorone in the vehicle to achieve the target concentration. The formulation will be mixed by inversion 5-6 times and placed on an orbital shaker for 30±5 min. Tilorone was prepared daily.

Favipiravir Preparation: A 0.5% solution of methylcellulose was prepared in sterile water. To this, the appropriate amount of Favipiravir was added, and the pH adjusted until the compound goes into solution. Favipiravir was prepared prior to challenge and stored at 4-8° C.

Example 1

Testing Vs Ebola and Marburg Strains

Figure 2:
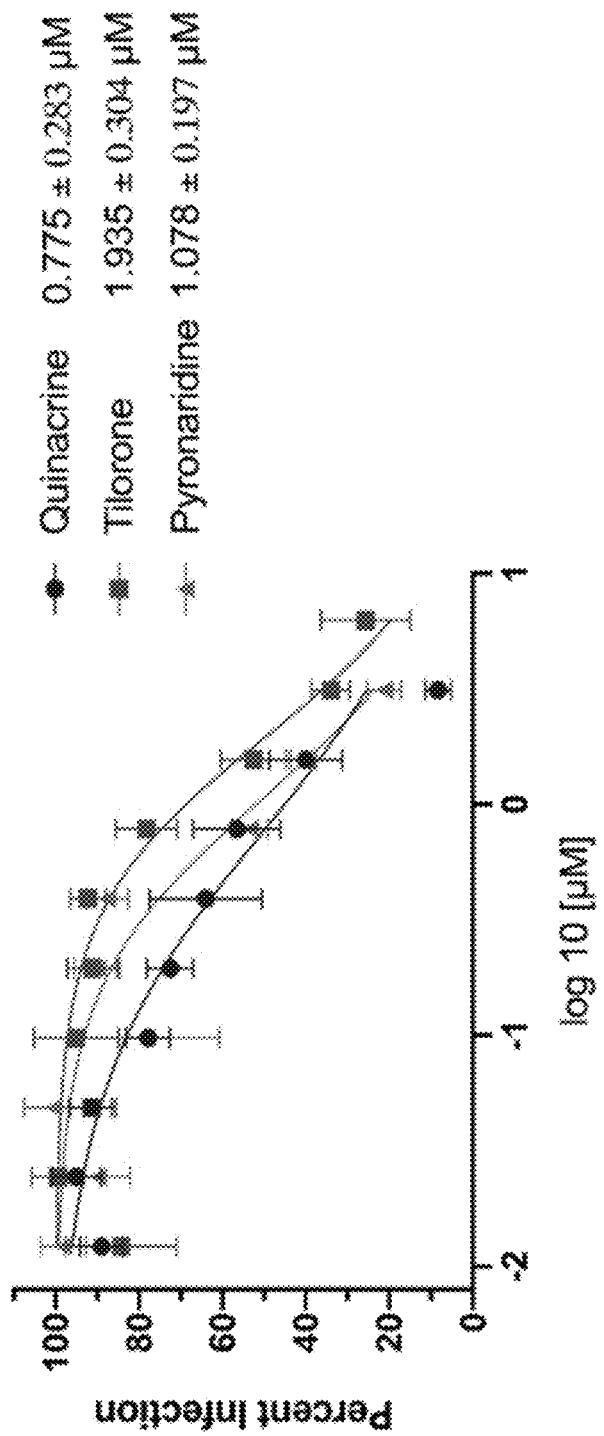
FIG. 2 is a graph showing the dose response relationship of quinacrine (circles), tilorone (squares) and pyronaridine (triangles) versus Marburg virus (MARV), Musoke strain. Data (percent infection versus log 10 of the compound concentration (in micromolar (µM)) represents multiple experiments (n=6). 50% inhibitory concentrations ($IC_{50}s$) ±SEM were 0.775±0.283 µM for quinacrine; 1.935±0.304 µM for tilorone; and 1.078±0.197 for pyrodaridine.
Figure 3B:
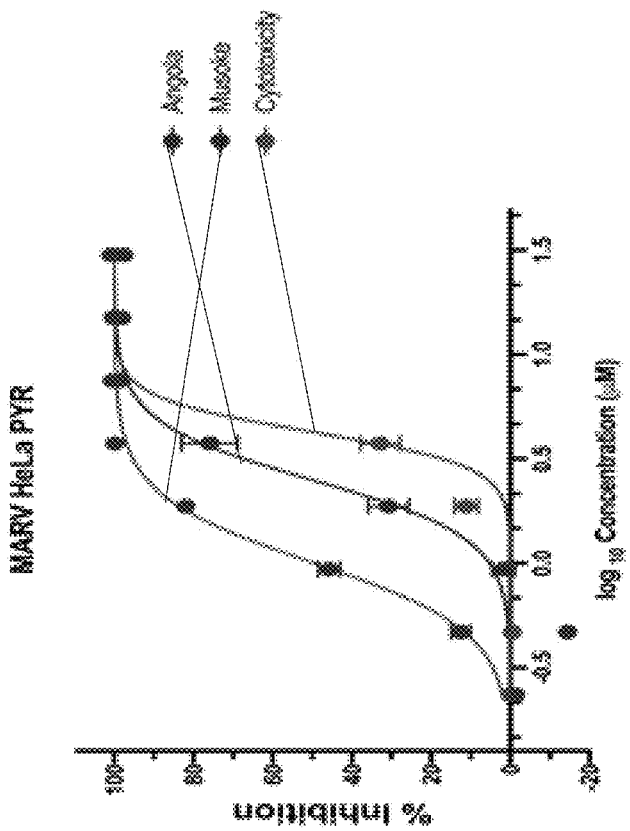
FIG. 3B is a graph showing pyronaridine (PYR) efficiency and cytotoxicity dose relationships against two Marburg virus (MARV) strains (Angola (Ang) and Musoke (Mus) in human (HeLa) cells. MARV/Ang: multiplicity of infection (MOI) 021; MARV/Mus: MOI 0.4. Data is provided as percent inhibition versus log 10 of the compound concentration (in micromolar (µM)).
Figure 3A:
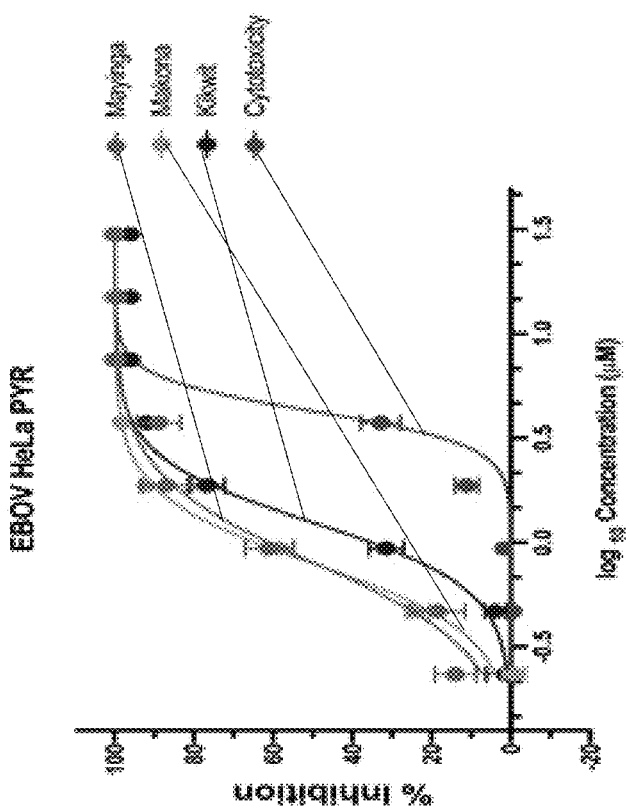
FIG. 3A is a graph showing pyronaridine (PYR) efficacy and cytotoxicity dose response relationships against multiple Ebola virus (EBOV) strains (Kikwit (Kik), Mayinga (May) and Makona (Mak)) in human (HeLa) cells. EBOV/Kik, Mak, May: multiplicity of infection (MOI) 0.21. Data is provided as percent inhibition versus log 10 of the compound concentration (in micromolar (µM)).
Figure 3D:
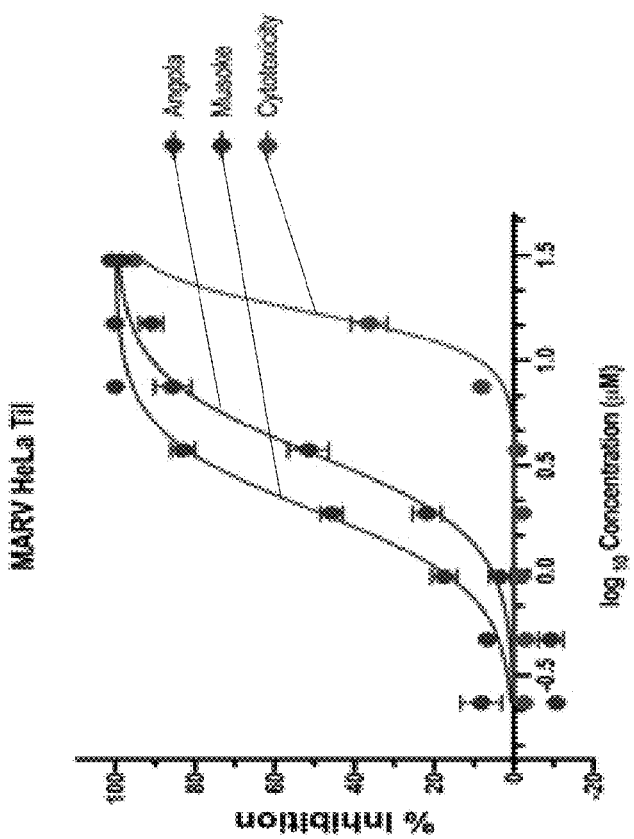
FIG. 3D is a graph showing tilorone (Til) efficiency and cytotoxicity dose relationships against two Marburg virus (MARV) strains (Angola (Ang) and Musoke (Mus) in human (HeLa) cells. MARV/Ang: multiplicity of infection (MOI) 021; MARV/Mus: MOI 0.4. Data is provided as percent inhibition versus log 10 of the compound concentration (in micromolar (µM)).
Figure 3C:
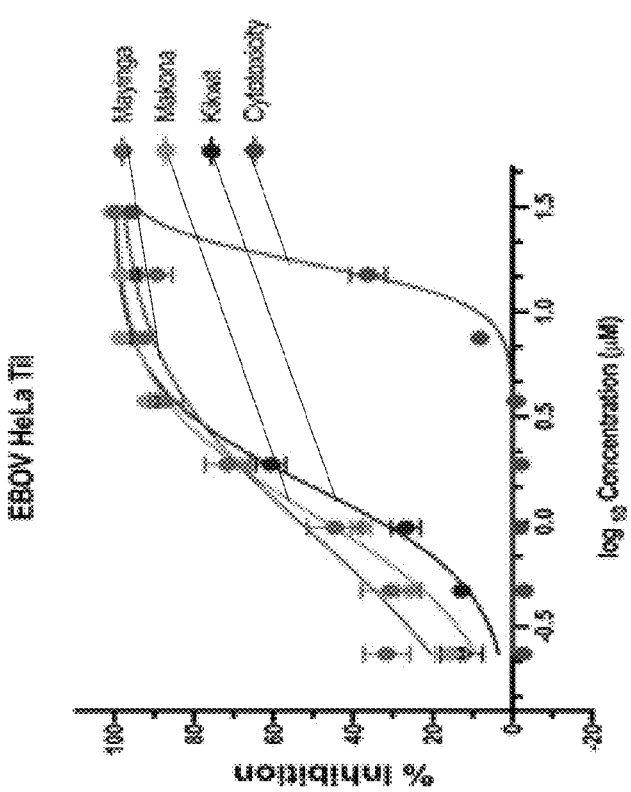
FIG. 3C is a graph showing tilorone (Til) efficacy and cytotoxicity dose response relationships against multiple Ebola virus (EBOV) strains (Kikwit (Kik), Mayinga (May) and Makona (Mak)) in human (HeLa) cells. EBOV/Kik, Mak, May: multiplicity of infection (MOI) 0.21. Data is provided as percent inhibition versus log 10 of the compound concentration (in micromolar (µM)).
Figure 3F:
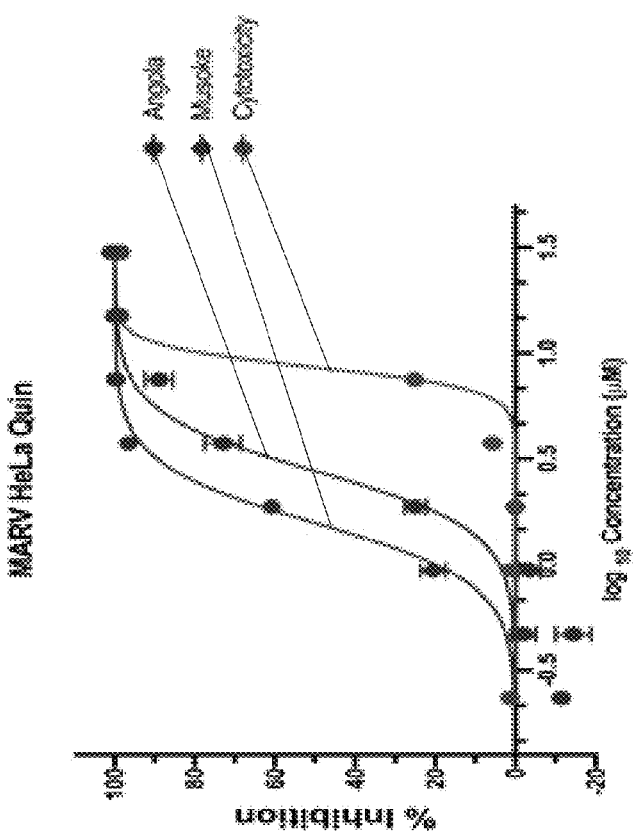
FIG. 3F is a graph showing quinacrine (Quin) efficiency and cytotoxicity dose relationships against two Marburg virus (MARV) strains (Angola (Ang) and Musoke (Mus) in human (HeLa) cells. MARV/Ang: multiplicity of infection (MOI) 021; MARV/Mus: MOI 0.4. Data is provided as percent inhibition versus log 10 of the compound concentration (in micromolar (µM)).
Figure 3E:
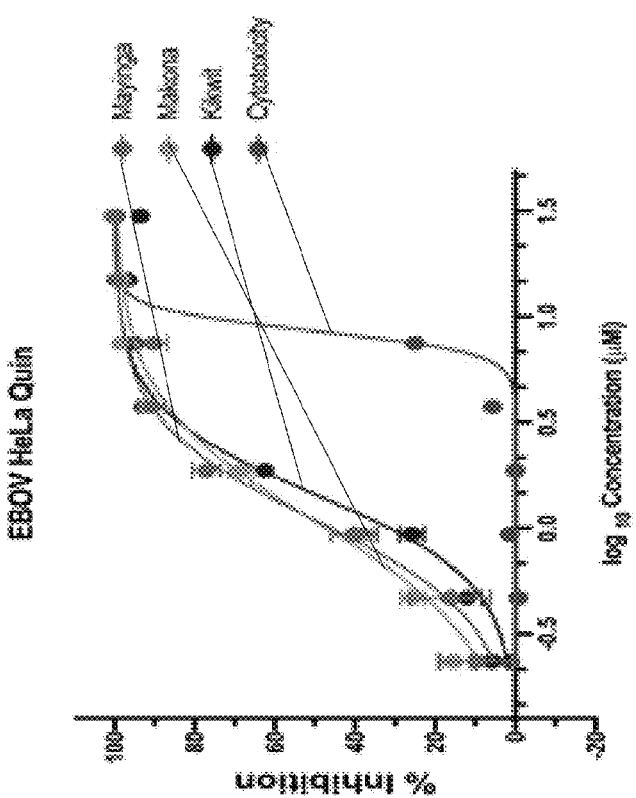
FIG. 3E is a graph showing quinacrine (Quin) efficacy and cytotoxicity dose response relationships against multiple Ebola virus (EBOV) strains (Kikwit (Kik), Mayinga (May) and Makona (Mak)) in human (HeLa) cells. EBOV/Kik, Mak, May: multiplicity of infection (MOI) 0.21. Data is provided as percent inhibition versus log 10 of the compound concentration (in micromolar (µM)).

Tilorone, pyronaridine and quinacrine were initially tested against Ebola virus (EBOV) Mayinga strain and it was confirmed that they block the entry stage of infection in a pseudotype assay. See FIG. 1. It was also found that these compounds are active against Marburg virus (MARV) Musoke strain in HeLa cells. See FIG. 2. These compounds were independently found to be similarly efficacious against multiple EBOV (Kikwit, Mayinga and Makona) and MARV (Musoke and Angola) strains in HeLa cells. See FIGS. 3A-3F and Table 1, below. Analysis via a F-test rejects the hypothesis that the $CC_{50}$ and the respective $IC_{50}$ are the same for each of the compounds evaluated (EBOV, Mayinga, tilorone is ambiguous).

TABLE 1

Pyronaridine, tilorone and quinacrine (±SD) show a similar efficacy against multiple strains of EBOV (Kikwit, Mayinga and Makona) and MARV (Musoke and Angola) in HeLa cells.

| Compound | $CC_{50}$ (μM)[a] | Virus | Strain | MOI | $IC_{50}$ (μM)[b] | SI[c] |
|---|---|---|---|---|---|---|
| Pyronaridine | 4.11 ± 0.50 | EBOV | Kikwit | 0.21 | 1.30 ± 0.42 | 3.2 |
| | | | Makona | 0.21 | 0.82 ± 0.19 | 5.0 |
| | | | Mayinga | 0.21 | 1.01 ± 0.58 | 4.1 |
| | | MARV | Angola | 0.21 | 2.72 ± 0.97 | 1.6 |
| | | | Musoke | 0.4 | 1.01 ± 0.11 | 4.1 |
| Tilorone | 18.04 ± 3.04 | EBOV | Kikwit | 0.21 | 1.48 ± 0.47 | 12.2 |
| | | | Makona | 0.21 | 1.14 ± 0.38 | 15.9 |
| | | | Mayinga | 0.21 | 1.21 ± 1.07 | 15.0 |
| | | MARV | Angola | 0.21 | 4.51 ± 1.93 | 4.1 |
| | | | Musoke | 0.4 | 2.05 ± 0.28 | 8.8 |
| Quinacrine | 8.62 ± 0.02 | EBOV | Kikwit | 0.21 | 1.41 ± 0.25 | 6.1 |
| | | | Makona | 0.21 | 1.05 ± 0.26 | 8.2 |
| | | | Mayinga | 0.21 | 1.48 ± 0.65 | 5.8 |
| | | MARV | Angola | 0.21 | 2.94 ± 0.76 | 2.9 |
| | | | Musoke | 0.4 | 1.57 ± 0.17 | 5.5 |

[a]Cytotoxicity was determined in HeLa cells that were mock infected. Data represent average of 3 dose response curves with 3 replicates per dose.
[b]Efficacy was determined in HeLa cells infected at a MOI of 0.21. Data represent average of 4-6 dose response curves with 3 replicates per dose.
[c]SI = $CC_{50}/IC_{50}$.

Example 2

Metabolic Stability Across Species

The in vitro metabolic stability of pyronaridine in mouse, guinea pig, non-human primate, and human has been previously reported (13). A comparison was performed for tilorone, quinacrine and chloroquine under largely similar conditions. Pyronaridine liver microsome (LM) metabolic stability increased in the order of guinea pig, non-human primate, human and then mouse. Tilorone had a similar species-LM stability relationship, with an increase in the order of guinea pig, non-human primate, mouse, followed by human. Chloroquine differed, with LM metabolic stability in the order of mouse, non-human primate, guinea pig and then human. Finally, quinacrine metabolic stability increased in the order of non-human primate, mouse, guinea pig and then human. See Table 2, below. The CYP2D6 substrate probe dextromethorphan metabolism closely paralleled the species differences observed for pyronaridine and was also used to normalize the $t_{1/2}$. See Tables 3 and 4.

TABLE 2

Liver Microsomal Metabolic Stability Across Species.

| Species | | Pyronaridine | Tilorone | Chloroquine | Quinacrine |
|---|---|---|---|---|---|
| Mouse | $t_{1/2}$ (min) | >186 | 102.7 | 47.3 | 12.6 |
| | $Cl_{int}$ (μL min/mg) | <7.4 | 13.5 | 29.3 | 110.0 |
| | $R^2$ | 0.65* | 0.91 | 0.96 | 0.98 |
| Guinea Pig | $t_{1/2}$ (min) | 66.1 | 12.2 | 132.6 | 17.1 |
| | $Cl_{int}$ (μL min/mg) | 21.0 | 113.7 | 10.5 | 81.3 |
| | $R^2$ | 0.86 | 1.00 | 0.90 | 0.98 |
| Non-Human Primate | $t_{1/2}$ (min) | 89.7 | 94.3 | 106.8 | 10.1 |
| | $Cl_{int}$ (μL min/mg) | 15.5 | 14.7 | 13.0 | 137.4 |
| | $R^2$ | 0.98 | 0.98 | 0.97 | 0.98 |
| Human | $t_{1/2}$ (min) | 122.2 | 127.1 | 201.4 | 27.5 |
| | $Cl_{int}$ (μL min/mg) | 11.4 | 10.9 | 6.9 | 50.5 |
| | $R^2$ | 0.81 | 0.98 | 0.95 | 0.97 |

*Poor fit of the data. Based on previous data (unpublished) using 1 mg LM/rxn, as opposed to 0.5 mg/rx, suggest metabolism in MLM and HLM are very similar

TABLE 3

Liver Microsomal Metabolic Stability Across Species Normalized to Detromethorphan Control.

| Species | Dextro-methorphan $t_{1/2}$ (min) | Dextro-methorphan: Pyronaridine | Dextro-methorphan: Tilorone | Dextro-methorphan: Chloroquine | Dextro-methorphan: Quinacrine |
|---|---|---|---|---|---|
| Mouse | 16.2 | >11.5 | 6.3 | 2.7 | 0.8 |
| Guinea Pig | 3.2 | 23.4 | 3.9 | 42.1 | 5.4 |
| Non-Human Primate | 5.7 | 16.7 | 16.9 | 19.1 | 1 |
| Human | 19.7 | 6.2 | 6.5 | 10.3 | 1.4 |

TABLE 4

Liver microsomal metabolic stability across species controls (Phenacetin (CYP 1A2), Diclofenac (CYP 2C9), Omeprazole (CYP 2C19), Dextromethorphan (CYP 2D6), Midazolam (CYP 3A4)).

| Species | Dextro-methorphan $t_{1/2}$ (min) | Midazolam $t_{1/2}$ (min) | Phenacetin $t_{1/2}$ (min) | Diclofenac $t_{1/2}$ (min) | Omeprazole $t_{1/2}$ (min) |
|---|---|---|---|---|---|
| Mouse | 13.23 | 1.678 | 3.3 | 39.6 | 15.7 |
| Guinea Pig | 2.90 | 3.749 | 2.675 | N/A | 34.0 |
| Non-Human Primate | 6.69 | 4.30 | 31.95 | 43.14 | 25.49 |
| Human | 14.82 | 2.35 | 45.2 | 3.8 | 23.5 |

Pyronaridine is metabolized more rapidly in Guinea pig liver microsomes and in vivo as compared to mouse and the only substrate that is metabolized more rapidly in GPLM then in MLM is dextromethorphan, correlating the two. Assuming pyronaridine is metabolized by one of these 5 cytochrome P450s and its metabolic rate is related to metabolism of known substrates, then pyronaridine is likely metabolized by the CYP2D family. This is also supported by lower metabolic stability for both pyronaridine and dextromethorphan in non-human primate liver microsomes.

Example 3

Metabolite Id Across Species

Figure 4A:
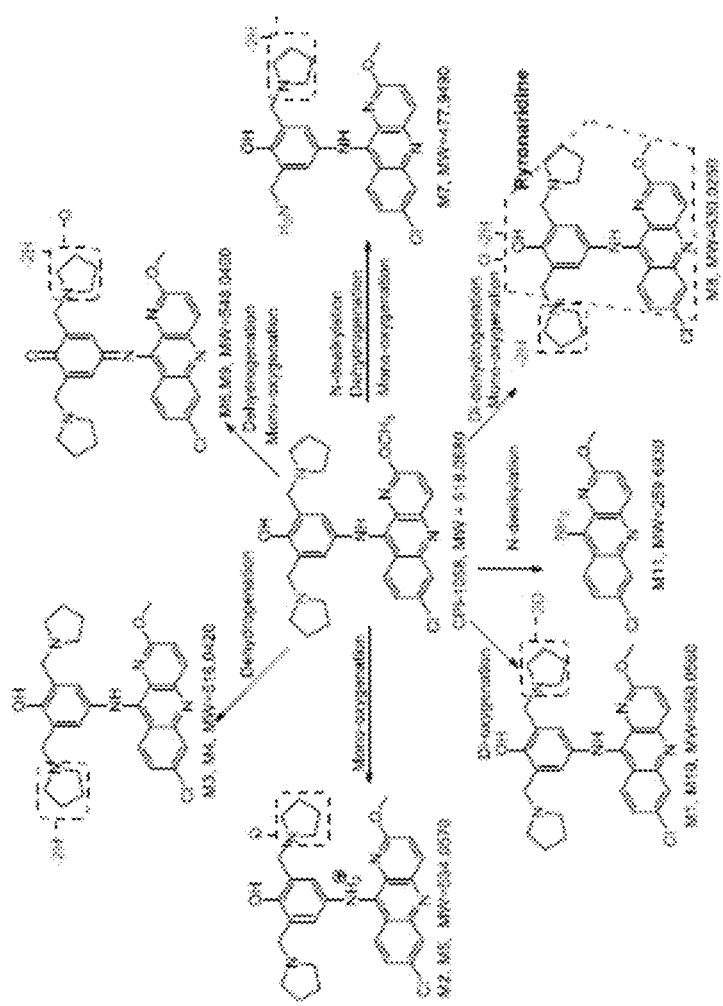
FIG. 4A is a schematic diagram showing the chemical structures of metabolites of pyronaridine in guinea pig, human and mouse liver microsomes.
Figures 4B, 4C:
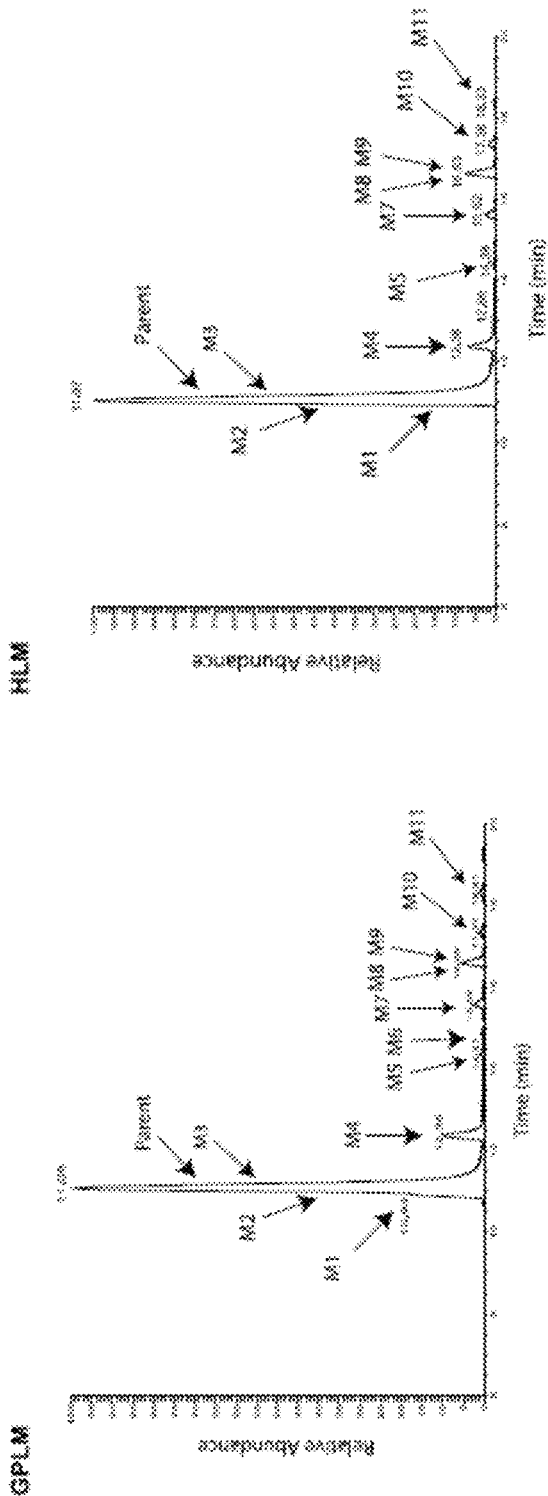
FIG. 4B is a graph showing a liquid chromatography-dual mass spectrometry (LC-MS/MS) ion chromatograph of pyronaridine (parent) and its metabolites in guinea pig liver microsomes (GPLM) after a 60-minute incubation period.
FIG. 4C is a graph showing a liquid chromatography-dual mass spectrometry (LC-MS/MS) ion chromatograph of pyronaridine (parent) and its metabolites in human liver microsomes (HLM) after a 60-minute incubation period.
Figure 5A:
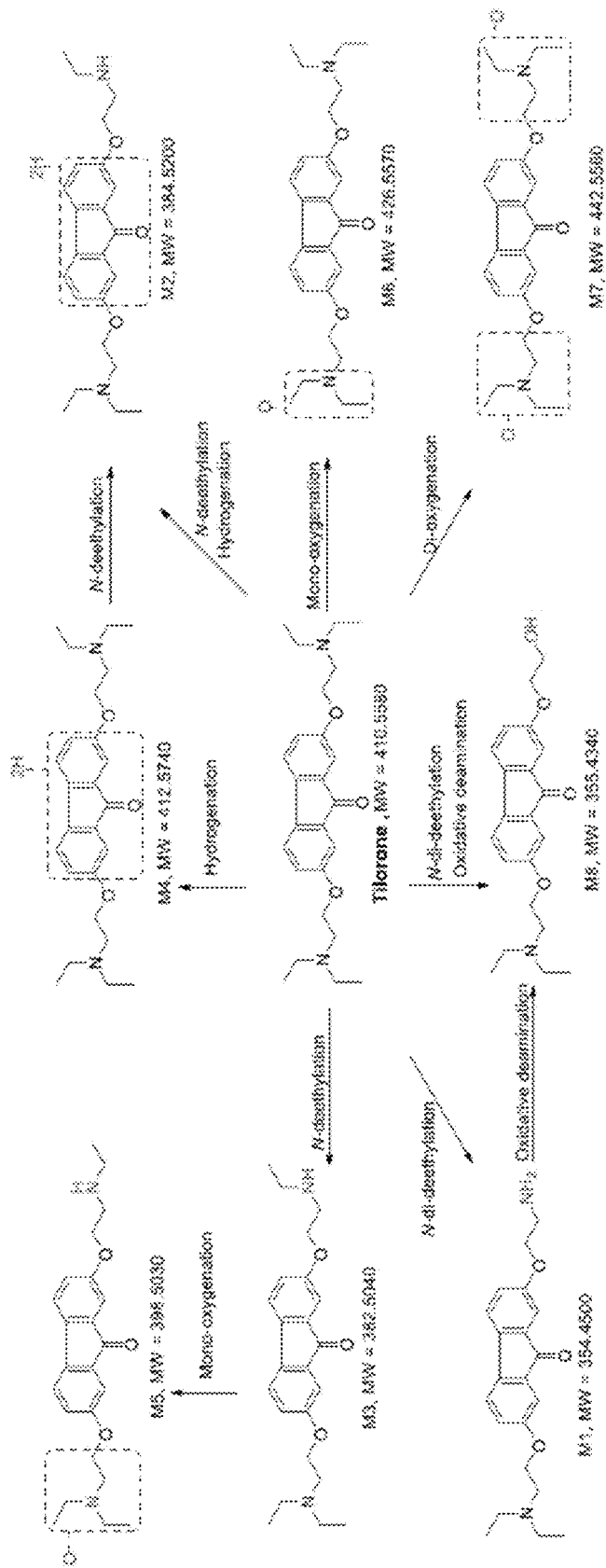
FIG. 5A is a schematic diagram showing the chemical structures of metabolites of tilorone in guinea pig, human and mouse liver microsomes.
Figure 5C:
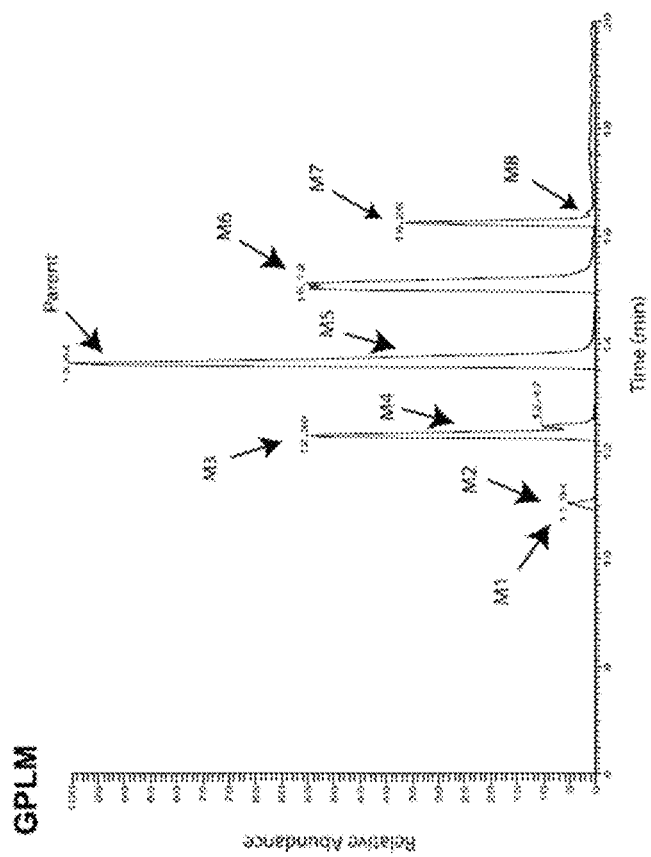
FIG. 5C is a graph showing a liquid chromatography-dual mass spectrometry (LC-MS/MS) ion chromatograph of tilorone (parent) and its metabolites in guinea pig liver microsomes (GPLM) after a 60-minute incubation period.
Figure 5B:
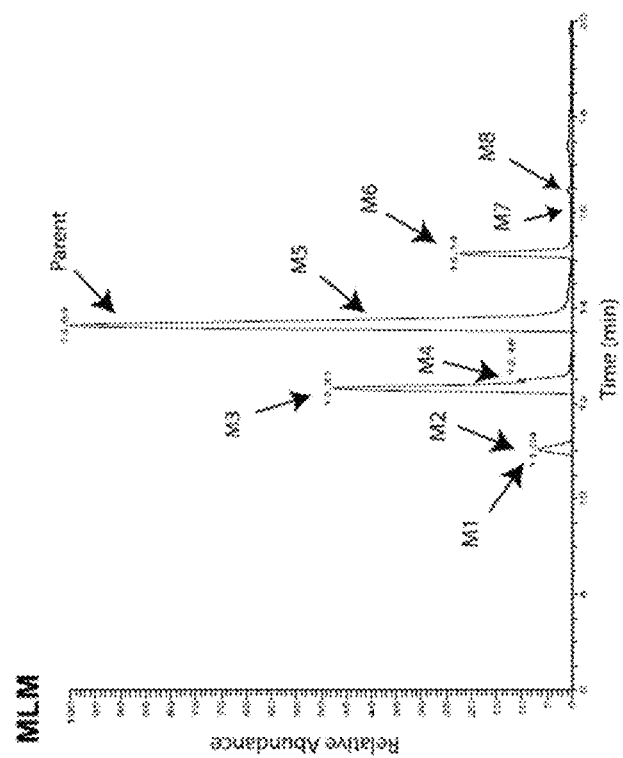
FIG. 5B is a graph showing a liquid chromatography-dual mass spectrometry (LC-MS/MS) ion chromatograph of tilorone (parent) and its metabolites in mouse liver microsomes (MLM) after a 60-minute incubation period.
Figure 5D:
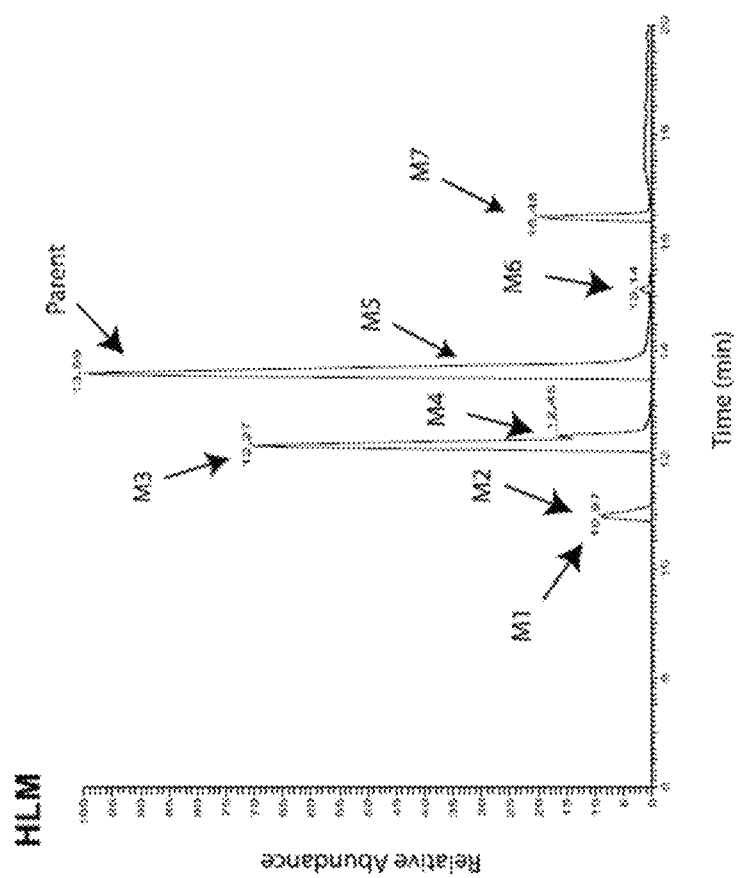
FIG. 5D is a graph showing a liquid chromatography-dual mass spectrometry (LC-MS/MS) ion chromatograph of tilorone (parent) and its metabolites in human liver microsomes (HLM) after a 60-minute incubation period.
Figure 6A:
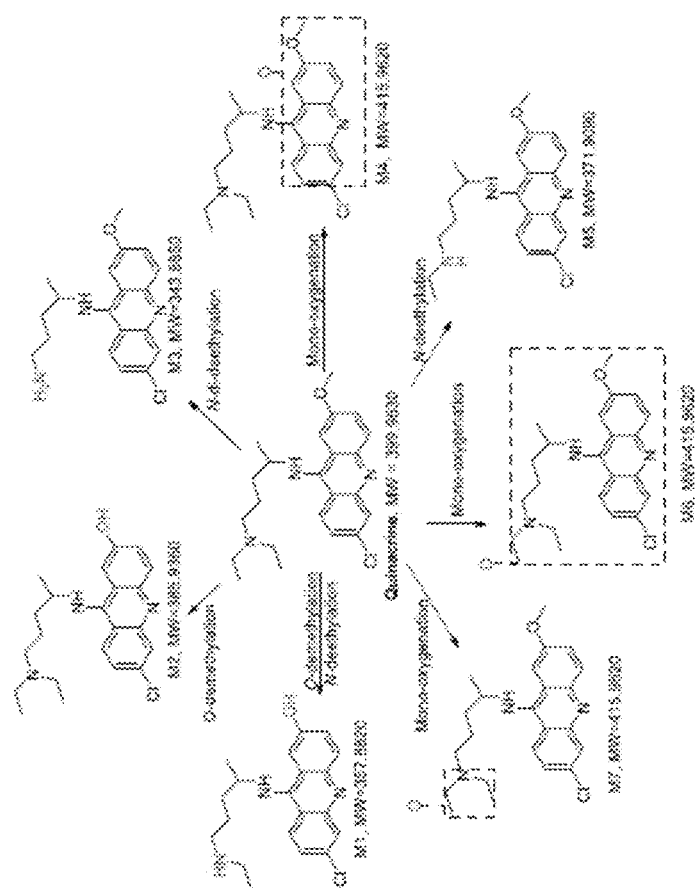
FIG. 6A is a schematic diagram showing the chemical structures of metabolites of quinacrine in guinea pig, human and mouse liver microsomes.
Figures 6B, 6C:
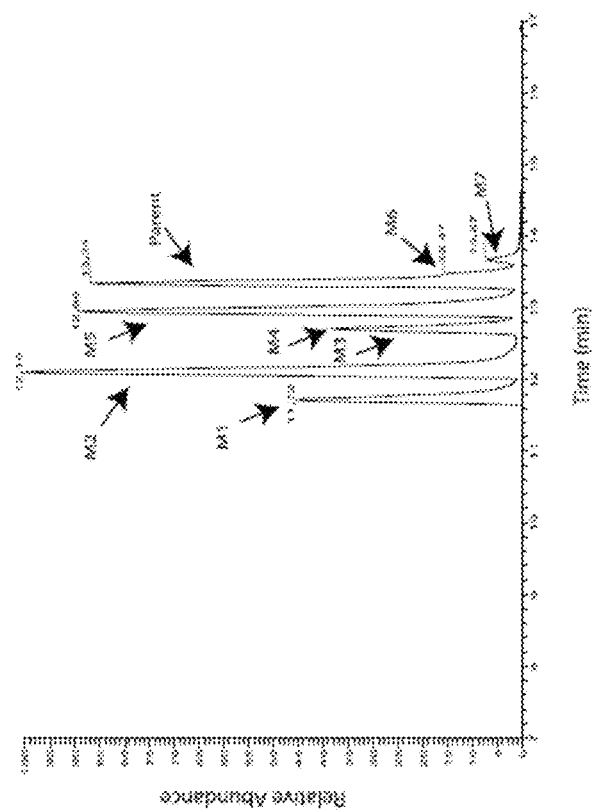
FIG. 6B is a graph showing a liquid chromatography-dual mass spectrometry (LC-MS/MS) ion chromatograph of quinacrine (parent) and its metabolites in mouse liver microsomes (MLM) after a 60-minute incubation period.
FIG. 6C is a graph showing a liquid chromatography-dual mass spectrometry (LC-MS/MS) ion chromatograph of quinacrine (parent) and its metabolites in guinea pig liver microsomes (GPLM) after a 60-minute incubation period.
Figure 6D:
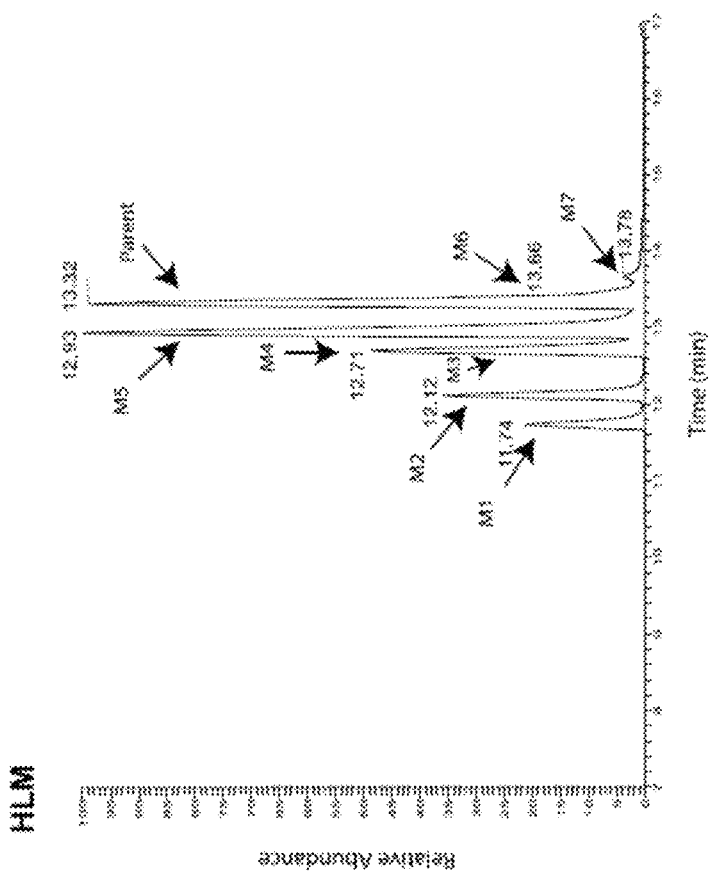
FIG. 6D is a graph showing a liquid chromatography-dual mass spectrometry (LC-MS/MS) ion chromatograph of quinacrine (parent) and its metabolites in human liver microsomes (HLM) after a 60-minute incubation period.
Figure 7A:
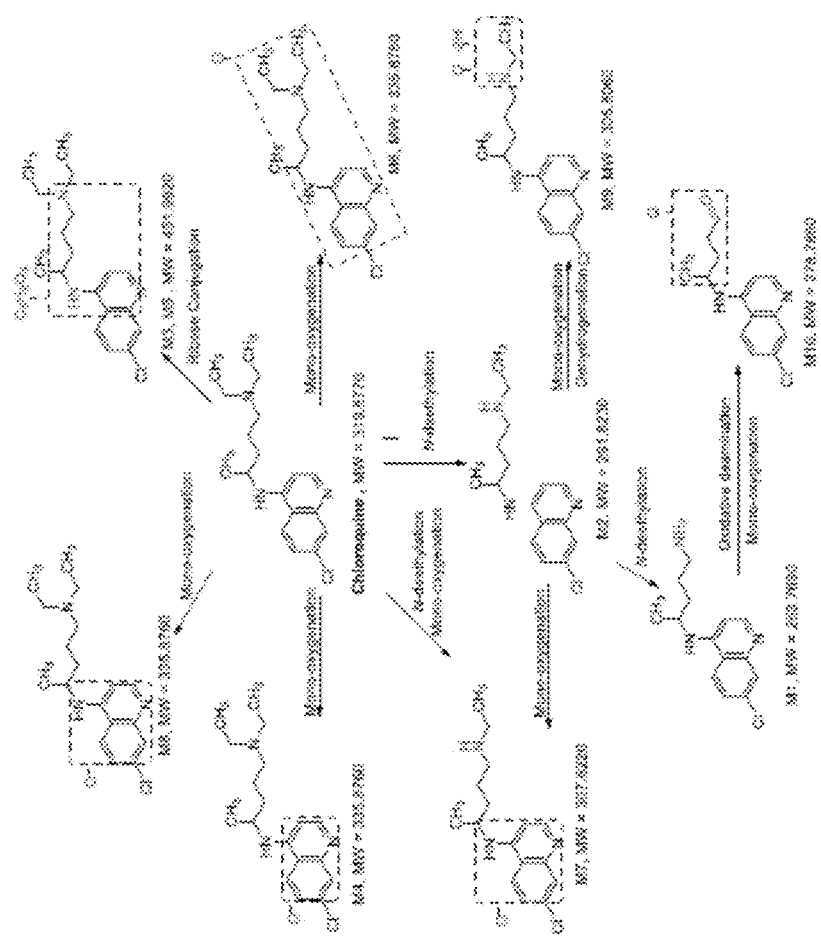
FIG. 7A is a schematic diagram showing the chemical structures of metabolites of chloroquine in guinea pig, human and mouse liver microsomes.
Figure 7C:
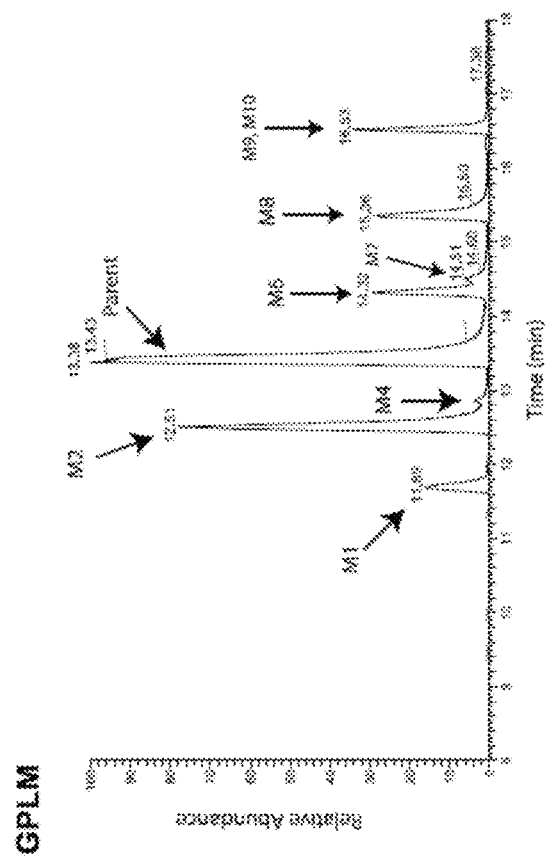
FIG. 7C is a graph showing a liquid chromatography-dual mass spectrometry (LC-MS/MS) ion chromatograph of chloroquine (parent) and its metabolites in guinea pig liver microsomes (GPLM) after a 60-minute incubation period.
Figure 7B:
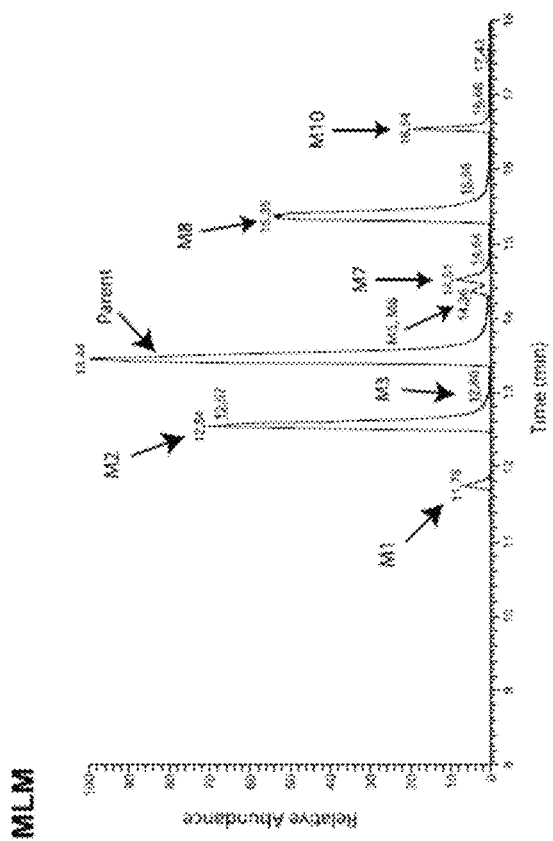
FIG. 7B is a graph showing a liquid chromatography-dual mass spectrometry (LC-MS/MS) ion chromatograph of chloroquine (parent) and its metabolites in mouse liver microsomes (MLM) after a 60-minute incubation period.
Figure 7D:
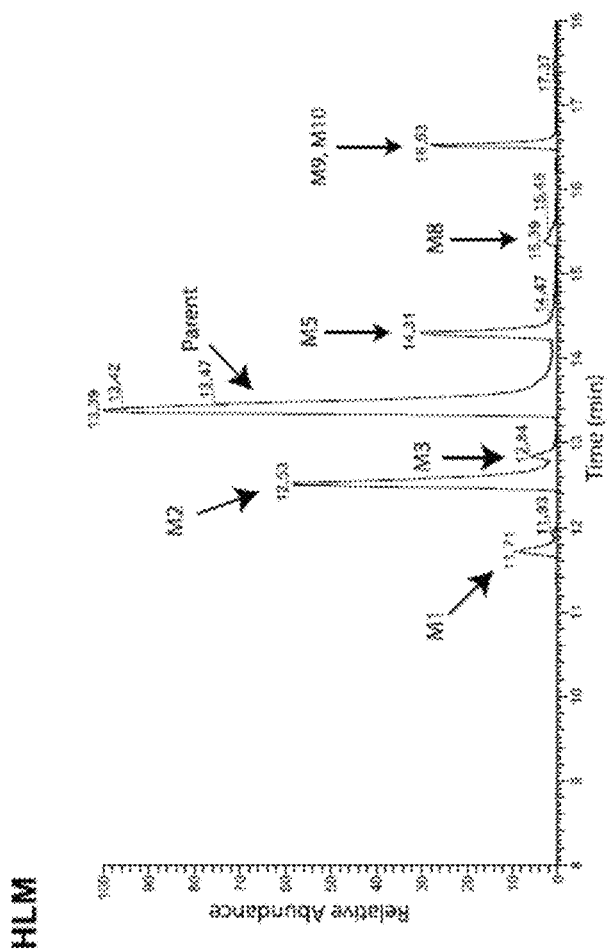
FIG. 7D is a graph showing a liquid chromatography-dual mass spectrometry (LC-MS/MS) ion chromatograph of chloroquine (parent) and its metabolites in human liver microsomes (HLM) after a 60-minute incubation period.

Pyronaridine metabolites produced in mouse microsomes were previously characterized (13). The metabolites of multiple compounds (pyronaridine, tilorone, quinacrine and chloroquine) were now analyzed across multiple species (human and guinea pig). See FIGS. 4A-4C, 5A-5D, 6A-6D, and 7A-7D. The relative abundancies of the parent and metabolites were calculated based on their selected ion chromatographic peak areas. The relative peak area abundance (%) for pyronaridine mono-oxygenation was much higher in guinea pig as compared to human liver microsomes. See FIGS. 4A-4C and Table 5, below. Tilorone N-deethylation and mono-oxygenation was higher in guinea pig relative to both mouse and human. See FIGS. 5A-5D and Table 6, below. Quinacrine O-demethylation was also 2-3 times higher in guinea pig. See FIGS. 6A-6D and Table 7, below. In contrast, chloroquine mono-oxygenation was highest in mouse relative to other species. See FIGS. 7A-7D and Table 8, below. Overall, guinea pig metabolism for these compounds in LMs differed substantially as compared to the other species tested.

TABLE 5

Relative Abundancies of Pyronaridine and Metabolites in Mouse Liver Microsomes (MLM), Guinea Pig Liver Microsomes (GPLM) and Human Liver Microsomes (HLM).

| Metabolite | Retention Time (min) | m/z (+) | Metabolic Pathway | Relative Peak Area/Abundance | | |
|---|---|---|---|---|---|---|
| | | | | MLM** | GPLM | HLM |
| M1 | 10.90 | 550.22 | Di-oxygenation | ND | 0.4 | 0.1 |
| M2 | 10.94 | 534.23 | Mono-oxygenation | 10 | 7.7 | 0.1 |
| Pyronaridine | 11.06 | 518.23 | n/a | 100 | 75.9 | 85.9 |
| M3 | 11.16 | 516.22 | Dehydration | ND | 2.7 | 2.5 |
| M4* | 12.36 | 516.22 | Dehydration | ND | 6.8 | 4.2 |
| M5* | 14.37 | 534.23 | Mono-oxygenation | 5 | 0.4 | 0.3 |
| M6 | 14.96 | 548.21 | Di-oxygenation and dehydration | <5 | 0.3 | 0.1 |
| M7 | 15.64 | 478.16 | Mono-oxygenation, dehydration and N-alkylation | ND | 1.2 | 1.2 |
| M8 | 16.60 | 530.20 | Mono-oxygenation and di-dehydration | ND | 0.5 | 0.5 |
| M9 | 16.67 | 532.21 | Mono-oxygenation and dehydration | <5 | 2.7 | 3.9 |
| M10 | 17.33 | 550.22 | di-oxygenation | <5 | 0.7 | 1.0 |
| M11 | 18.35 | 260.06 | N-dealkylation | ND | 0.7 | 0.2 |

**previously published data; *M4 and M5 detected in T = 0 min and standard samples; ND = not detected.

TABLE 6

Relative Abundancies of Tilorone and Metabolites in Mouse Liver Microsomes (MLM), Guinea Pig Liver Microsomes (GPLM) and Human Liver Microsomes (HLM).

| Metabolite | Retention Time (min) | m/z (+) | Metabolic Pathway | Relative Peak Area/Abundance | | |
|---|---|---|---|---|---|---|
| | | | | MLM | GPLM | HLM |
| M1 | 11.00 | 355.20 | N-di-deethylation | 1.2 | 0.5 | 2.0 |
| M2 | 11.04 | 385.25 | N-deethylation and hydrogenation | 1.6 | 1.0 | 1.6 |
| M3 | 12.30 | 383.23 | N-deethylation | 22.2 | 15.6 | 31.3 |
| M4 | 12.48 | 413.28 | Hydrogenation | 3.0 | 1.9 | 3.6 |
| Tilorone | 13.61 | 411.26 | n/a | 62.9 | 35.5 | 54.9 |
| M5 | 13.81 | 399.23 | N-deethylation and mono-oxygenation | 0.6 | 20.0 | 0.1 |
| M6 | 15.12 | 427.26 | Mono-oxygenation | 8.2 | 16.6 | 0.5 |
| M7 | 16.26 | 443.25 | Di-oxygenation, | 0.1 | 8.7 | 8.7 |
| M8 | 16.46 | 356.19 | N-di-deethylation and oxidative deamination | 0.2 | 0.2 | 0.2 |

ND = not detected.

TABLE 7

Relative Abundancies of Quinacrine and Metabolites in Mouse Liver Microsomes (MLM), Guinea Pig Liver Microsomes (GPLM) and Human Liver Microsomes (HLM).

| Metabolite | Retention Time (min) | m/z (+) | Metabolic Pathway | Relative Peak Area/Abundance MLM | GPLM | HLM |
|---|---|---|---|---|---|---|
| M1 | 11.72 | 358.17 | O-demethylation and N-deethylation | 7.9 | 12.3 | 6.0 |
| M2 | 12.10 | 386.20 | O-demethylation | 14.1 | 30.1 | 9.7 |
| M3 | 12.71 | 344.15 | N-di-deethylation | 7.8 | 5.5 | 13.2 |
| M4 | 12.71 | 416.21 | Mono-oxygenation | 1.1 | 3.5 | 1.6 |
| M5* | 12.96 | 372.18 | N-deethylation | 36.3 | 24.8 | 36.4 |
| Quinacrine | 13.32 | 400.22 | n/a | 32.0 | 20.7 | 32.3 |
| M6 | 13.48 | 416.21 | Mono-oxygenation | 0.2 | 1.8 | 0.3 |
| M7 | 13.67 | 416.21 | Mono-oxygenation | 0.6 | 1.3 | 0.5 |

*M5 detected in T0 minute sample and in ACN/$H_2O$ (v/v, 1/9).

TABLE 8

Relative Abundancies of Chloroquine and Metabolites in Mouse Liver Microsomes (MLM), Guinea Pig Liver Microsomes (GPLM) and Human Liver Microsomes (HLM).

| Metabolite | Retention Time (min) | m/z (+) | Metabolic Pathway | Relative Peak Area/Abundance MLM | GPLM | HLM |
|---|---|---|---|---|---|---|
| M1* | 11.71 | 264.13 | N-di-deethylation | 1.6 | 4.9 | 2.9 |
| M2* | 12.53 | 292.16 | N-deethylation | 23.8 | 24.4 | 23.3 |
| M3 | 12.84 | 452.23 | Ribose conjugation | 0.1 | ND | 1.8 |
| M4 | 12.86 | 336.18 | Mono-oxygenation | ND | 0.9 | D |
| Chloroquine | 13.39 | 320.19 | N/A | 42.5 | 43.3 | 56.7 |
| M5 | 14.31 | 452.23 | Ribose conjugation | 0.1 | ND | 8.5 |
| M6 | 14.36 | 336.18 | Mono-oxygenation | 1.0 | 7.3 | D |
| M7 | 14.51 | 308.15 | N-deethylation and mono-oxygenation | 2.6 | 1.7 | D |
| M8 | 15.39 | 336.18 | Mono-oxygenation | 24.6 | 9.3 | 1.0 |
| M9 | 16.50 | 306.14 | N-deethylation, dehydrogenation, and mono-oxygenation | 0.1 | 1.5 | 0.1 |
| M10 | 16.53 | 279.09 | N-di-deethylation, mono-oxygenation, and oxidative deamination | 3.6 | 6.7 | 5.7 |

*M1 and M2 were detected at T = 0 min and in the standard sample; ND = Not detected; D = detected.

Example 4

Mouse Adapted Ebola Testing

Figure 8B:
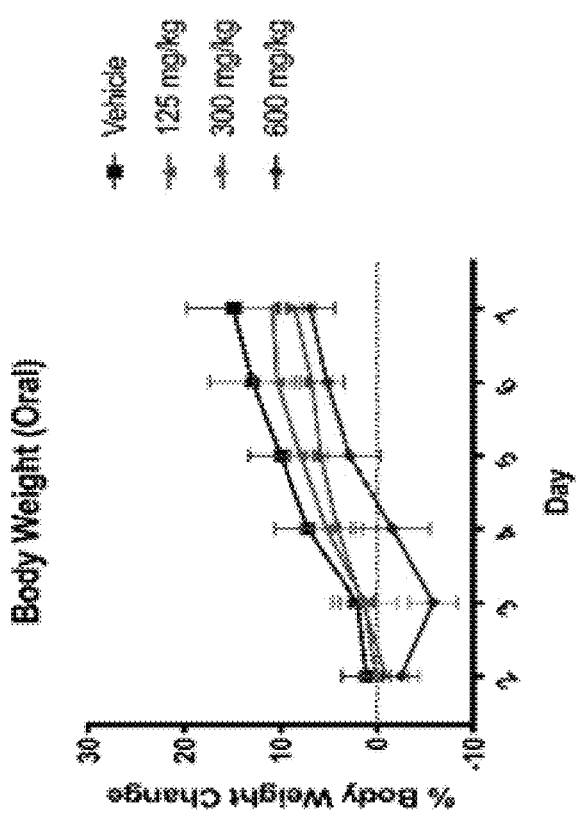
FIG. 8B is a graph from a maximum tolerated dose (MTD) study showing the change in body weight (as a percentage) of guinea pigs dosed via oral gavage with 0 milligrams per kilogram (mg/kg) (vehicle), 125 mg mg/kg, 300 mg/kg, or 600 mg/kg pyronaridine as a function of time (study day).
Figure 8A:
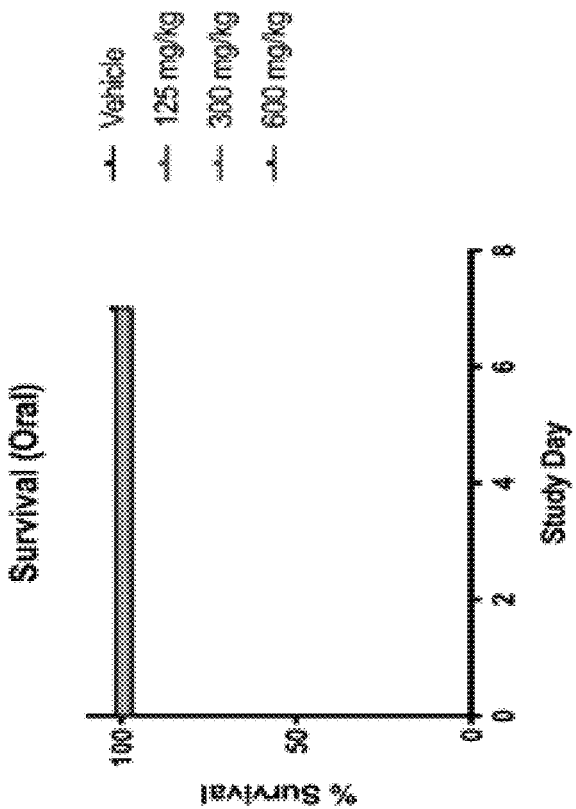
FIG. 8A is a graph from a maximum tolerated dose (MTD) study showing the percent survival of guinea pigs dosed via oral gavage with 0 milligrams per kilogram (mg/kg) (vehicle), 125 mg mg/kg, 300 mg/kg, or 600 mg/kg pyronaridine as a function of time (study day).
Figure 8D:
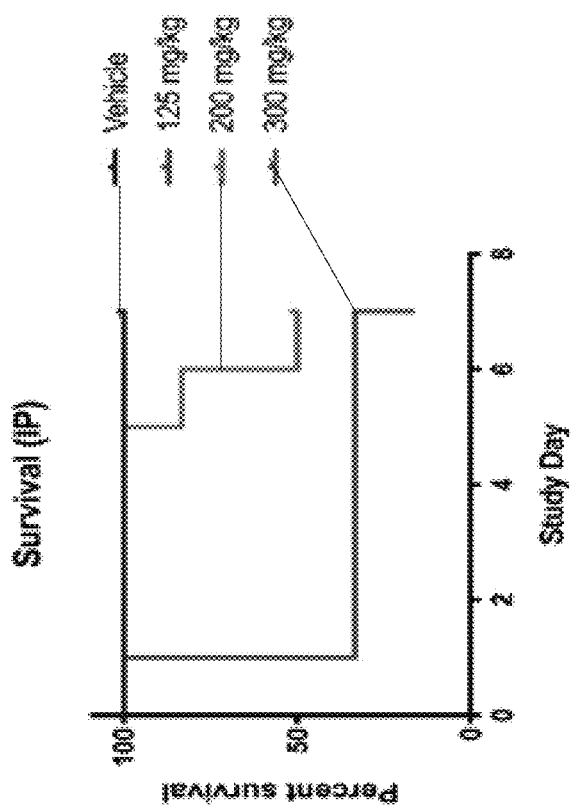
FIG. 8D is a graph from a maximum tolerated dose (MTD) study showing the percent survival of guinea pigs dosed intraperitoneally with 0 milligrams per kilogram (mg/kg) (vehicle), 125 mg mg/kg, 200 mg/kg, or 300 mg/kg pyronaridine as a function of time (study day).
Figure 9A:
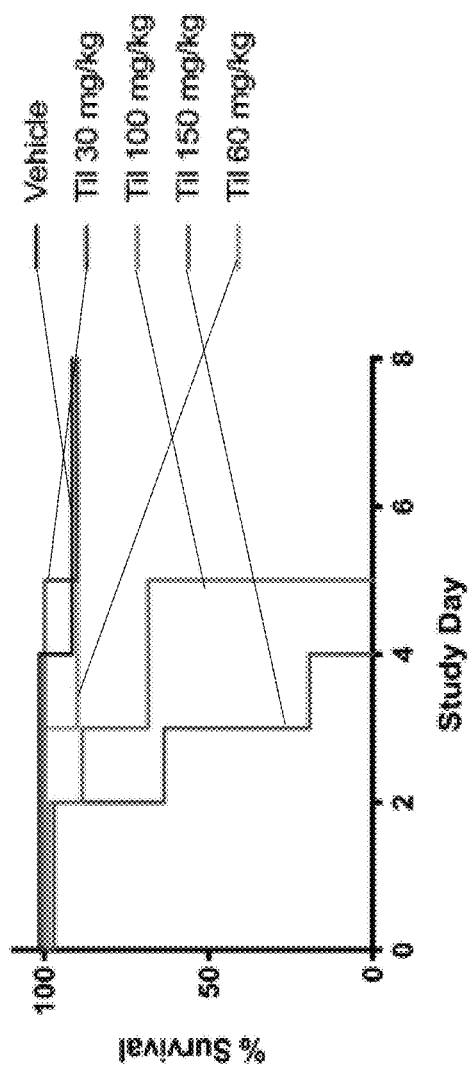
FIG. 9A is a graph from a maximum tolerated dose (MTD) study showing the percent survival of guinea pigs dosed via oral gavage with 0 milligrams per kilogram (mg/kg) (vehicle), 30 mg/kg, 60 mg mg/kg, 100 mg/kg, or 150 mg/kg tilorone as a function of time (study day).

Pyronaridine, tilorone and quinacrine were each dosed i.p to BALB/c mice. Ebola virus *Mus musculus*/COD/1976/Mayinga-CDC-808012 (maEBOV) stock virus from clarified supernatant from maEBOV-infected Vero E6 cell monolayers in growth medium/20% fetal bovine serum/0.01 M Tris was diluted from the $1.05\times10^7$ PFU/ml stock to a target challenge dose concentration of 1,000 PFU/ml such that animals received a target of 100 PFU per 100-μl dose. Viremia was assessed by plaque assays and qRT-PCR on samples obtained from mice that met criteria for euthanasia during daily observation or from animals that survived to the end of the study.

Pyronaridine (75 mg/kg) was shown to protect mice after a single dose showing 100% survival. See Table 9. Tilorone (30 mg/kg) dosed once a day for 8 days demonstrated 100% survival whether dosed at 2 h or 24 h post infection. Quinacrine (25 mg/kg) was shown to protect mice resulting in 70% survival when dosed 1 h post infection for 8 days.

TABLE 9

Mouse Adapted Ebola Efficacy

| Compound | Dose (i.p.) | Efficacy result |
|---|---|---|
| Pyronaridine | 75 mg/kg single dose. | 100% survival dosed at 1 h post infection, plaque assay shows a statistically significant reduction P < 0.0001 vs control. |
| Tilorone | 30 mg/kg once daily dosing for 8 days. | 100% survival at 2 h or 24 h post infection. No viable virus detected in animals at day 28. |
| Quinacrine | 25 mg/kg dosed 1 h post challenge for 8 days. | 70% survival dosed at 1 h post infection, plaque assay shows a statistically significant reduction P < 0.093. |

Example 5

Guinea Pig Dose Range-Finding Toxicity

The maximum tolerated dose of pyronaridine was evaluated in Hartley guinea pigs. See FIGS. 8A-8F. In the pyronaridine i.p.-dosed groups the highest dose level of 300 mg/kg appeared to be toxic, with 4 of 6 guinea pigs found dead within 30 mins post injection. In addition, one died on day 7. Surprisingly, the final surviving guinea pig showed no abnormal clinical observations. For the 200 mg/kg i.p.-dosed guinea pigs, 2 of 6 were found dead on days 5 and 6 and one met criteria for euthanasia on day 6. The remaining surviving guinea pigs from this group were found prostate on day 7. See FIG. 8D. No abnormal clinical observations were noted for guinea pigs administered either 125 mg/kg pyronaridine or vehicle via i.p. administration for the duration of the study. Oral dosing drastically reduced toxicity, with only 1 of 6 having any abnormal clinical observations at 600 mg/kg, which was detected directly following administration. This animal was found breathing rapidly for 6 mins, but fully recovered 2 hours post dose. There were no abnormal clinical observations at 300 or 125 mg/kg via oral administration. Based on these results, the maximum tolerated dose (MTD) for a single pyronaridine dose was determined as 125 and >600 mg/kg for i.p. and oral administration, respectively. See FIG. 8A. The maximum tolerated dose of tilorone was also tested in guinea pigs. See FIG. 9A.

Example 6

Guinea Pig Pharmacokinetics Evaluation of Pyronaridine

Figure 8C:
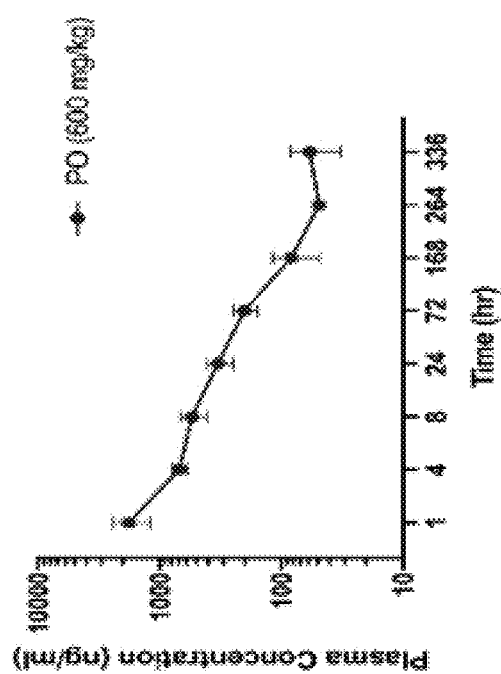
FIG. 8C is a graph showing the relationship between plasma concentration (in nanograms per milliliter (ng/ml) of pyronaridine versus time (in hours (hr)) after oral dosing with 600 milligrams per kilogram (mg/kg) pyronaridine in guinea pigs.
Figure 8F:
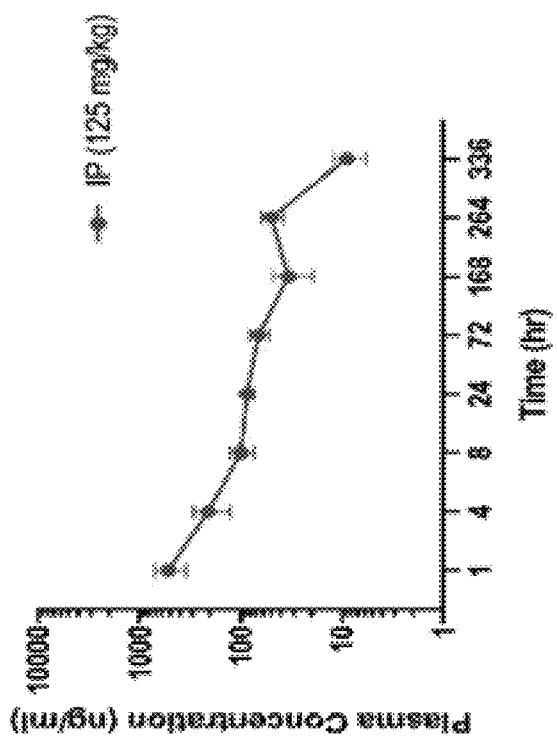
FIG. 8F is a graph showing the relationship between plasma concentration (in nanograms per milliliter (ng/ml) of pyronaridine versus time (in hours (hr)) after intraperitoneal administration of 125 milligrams per kilogram (mg/kg) pyronaridine in guinea pigs.
Figure 8E:
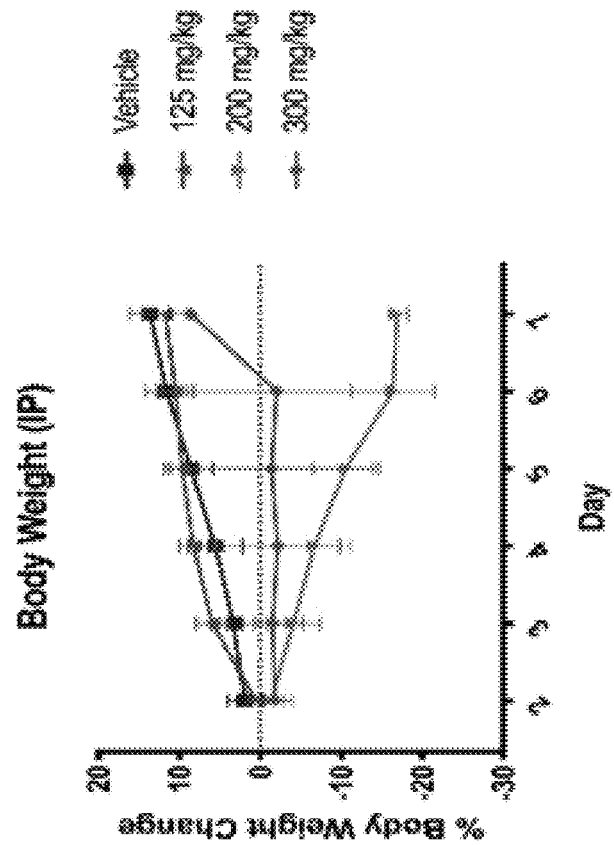
FIG. 8E is a graph from a maximum tolerated dose (MTD) study showing the change in body weight (as a percentage) of guinea pigs dosed via intraperitoneally with 0 milligrams per kilogram (mg/kg) (vehicle), 125 mg mg/kg, 200 mg/kg, or 300 mg/kg pyronaridine as a function of time (study day).
Figure 9B:
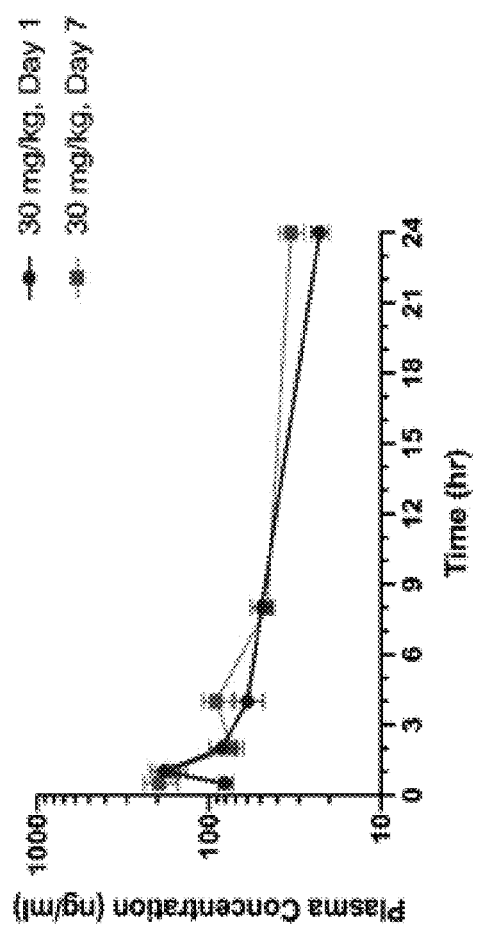
FIG. 9B is a graph showing plasma concentration (in nanograms per milliliter (ng/ml) versus time (in hours) in guinea pigs dosed with a single (circles) dose of 30 milligrams per kilogram (mg/kg) tilorone or after the seventh dose of 30 mg/kg tilorone administered once a day for seven days.
Figure 9C:
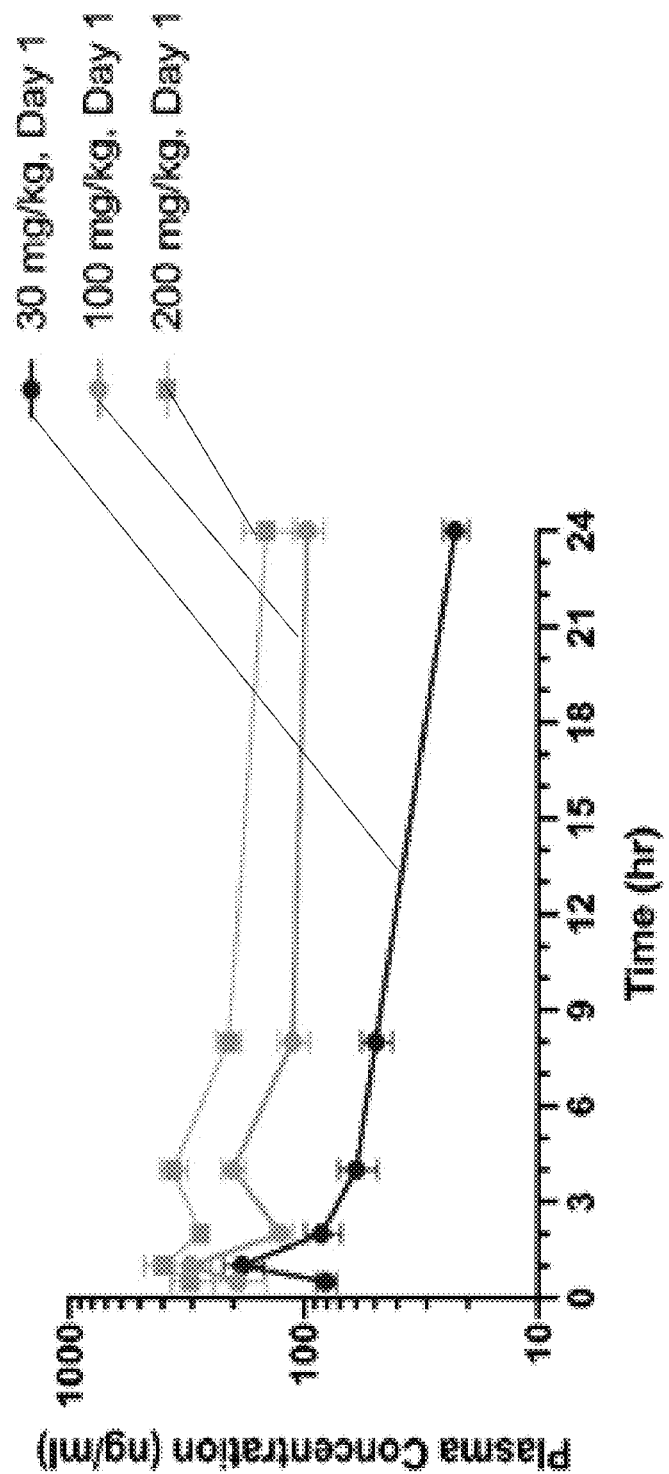
FIG. 9C is a graph showing the relationship between plasma concentration (in nanograms per milliliter (ng/ml) of tilorone versus time (in hours (hr)) after a single dose of tilorone at a concentration of 30 milligrams per kilogram (mg/kg), 100 mg/kg, or 200 mg/kg.
Figure 10:
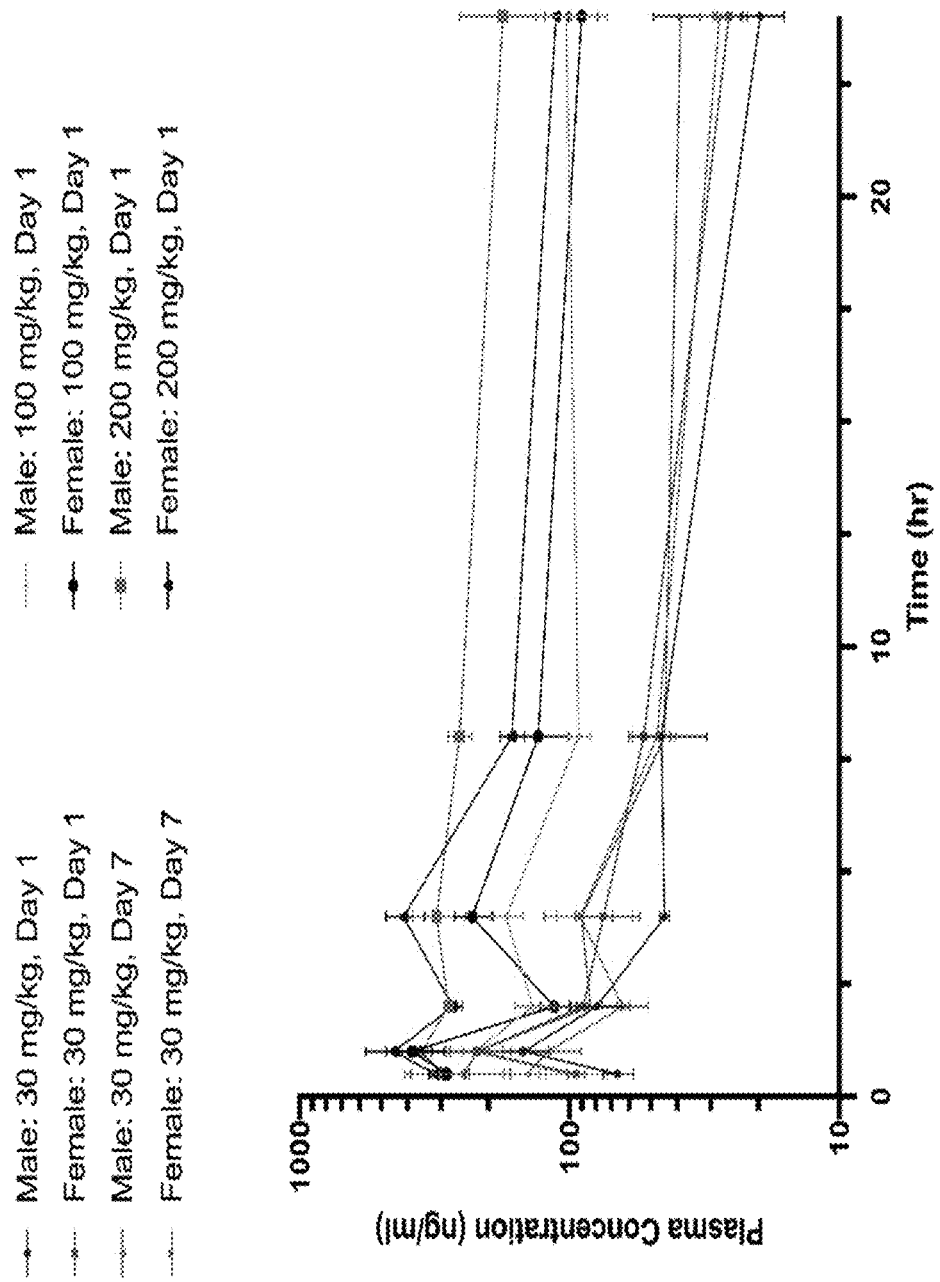
FIG. 10 is a graph showing the pharmacokinetics profile of tilorone (plasma concentration in nanograms per milliliter (ng/ml) versus time after the single or final dose of tilorone) as a function of dose and gender in guinea pigs. Data is provided for male guinea pigs after one dose of 30 milligrams per kilogram (mg/kg) tilorone (small circles); female guinea pigs after one dose of 30 mg/kg tilorone (small squares), male guinea pigs after the seventh dose of once-a-day dosing with 30 mg/kg tilorone (small upward-facing triangles), female guinea pigs after the seventh dose of once-a-day dosing with 30 mg/kg tilorone (small downward-facing triangles), male guinea pigs after one dose of 100 mg/kg tilorone (diamonds), female guinea pigs after one dose of 100 mg/kg tilorone (large circles), male guinea pigs after one dose of 200 mg/kg tilorone (large squares), and female guinea pigs after one dose of 200 mg/kg tilorone (larger upward-facing triangles). Comparison by respective dose showed there was no statistically significant in-group difference between male and female GPs or between a single and 7-day dosing regimen by sex ($C_{max}$ or $AUC_{last}$, Dunnett's T3 test).

The pharmacokinetics of pyronaridine was evaluated in Hartley guinea pigs. See FIGS. 8C and 8F. After an initial rapid absorption phase, the pyronaridine plasma profile exhibited a distribution phase at about 1 hr, then a prolonged phase with plasma drug concentrations remaining essentially unchanged, or slightly higher until about 72 hrs. All samples for animals dosed orally and i.p. contained measurable levels of pyronaridine though 336 and 168 hours, respectively (LLOQ=1 ng/ml). The plasma drug levels were analyzed using noncompartmental modeling allowing for the calculation of pharmacokinetic parameters. See Table 2, above. Pyronaridine plasma levels reached the peak in the first sample, taken at one hour post administration. The elimination-phase $t_{1/2}$ was calculated as 72.7 and 90.5 hours for i.p. and oral administration, respectively. This is shorter than the $t_{1/2}$ found in humans and mice of between 195-251 hours (16, 17) and 146 hours (13), respectively. Maximum concentration of unbound drug in plasma ($C_{max}$), area under the concentration-time curve from time zero to the last measurable concentration ($AUC_{last}$), and area under the concentration-time curve from time zero to infinity ($AUC_{Inf}$) are provided in Table 10, below. Dose A was 125 mg/kg administered IP to 3 male mice, while Dose B was 600 mg/kg administered orally in three male mice. The pharmacokinetics of tilorone were also evaluated in guinea pigs. See FIGS. 9B, 9C, and 10.

TABLE 10

Mean Pharmacokinetics Data in Male Guinea Pigs Treated with Pyronaridine.

| Dose | $T_{1/2}$ (h) | SE | $T_{max}$ (h) | $C_{max}$ (ng/ml) Mean | SE | $AUC_{last}$ (hr * ng/ml) Mean | SE | $AUC_{inf}$ (hr * ng/ml) Mean | SE |
|---|---|---|---|---|---|---|---|---|---|
| A | 72.7 | 9.3 | 1 | 523 | 175 | 16,565 | 5269 | 17,430 | 5428 |
| B | 90.5 | 3.9 | 1 | 1800 | 348 | 50,964 | 4406 | 58,783 | 6712 |

Example 7

Pyronaridine Efficacy and Clinical Observations

The efficacy of pyronaridine was evaluated in Hartley guinea pigs challenged with guinea pig adapted EBOV (gpa-EBOV). All animals in vehicle treatment (Group 1) succumbed to disease by study day 12 (100% mortality). Group 2 (pyronaridine 300 mg/kg) and Group 3 (pyronaridine 600 mg/kg) resulted in 40% and 33% survival, respectively. Among the 16 animals in the combined Group 4 (favipiravir 300 mg/kg), 7 guinea pigs survived through the end of the 21-day study period; the other 9 guinea pigs succumbed to disease by study day 14 (43.75% survival). See FIG. 11A. It should be noted that an animal in Group 2 was euthanized due to a clinical score of 4 on study day 2. Ebola disease in guinea pigs does not progress this rapidly so it is unlikely the animal succumbed to disease and it is more likely the animal incurred esophageal trauma because of the oral gavage technique. Therefore, this animal was been removed from data analysis.

Body weight results for each treatment group are summarized in FIG. 11B. Animals in Group 1 maintained body weight through study day 7 but decreased by study day 10, when all animals succumbed to disease. Group 2 animal body weight continuously decreased through study day 7, with surviving animals returning to pre-challenge body weights by study day 10. Group 3 animals dropped body weight following challenge, but the survivors reverted to pre-challenge body weight by the end of the 21-day study. If should be noted that an animal in this group had developed clinical signs late and succumbed to infection on study day 17. Animals in Group 4 remained at a consistent body weight until study day 10 where the mean body weight began to decrease briefly, but the surviving animals rebounded to pre-challenge weight by study day 13.

Plaque assay results from serum samples taken from animals that met euthanasia criteria during the scheduled observation times from all four groups are presented in FIG. 11D. Only 3 of the 12 terminal samples had detectable levels of viable gpa-EBOV: one animal from Group 1 ($1.15\times10^6$ PFU/mL) and two animals from Group 2 ($8.15\times10^5$ geometric mean PFU/mL). Interestingly, all the guinea pigs treated with favipiravir were below the limit of detection for the plaque assay. See FIGS. 12A-12D. Serum was also harvested from guinea pigs (3 male and 3 female) from each group on study day 3 and yielded quantifiable virus for vehicle (1 GP, $8.5\times10^4$ PFU/mL), pyronaridine 300 mg/kg (2 GP, $2.6\times10^5$ and $2.0\times10^3$ PFU/mL), pyronaridine 600 mg/kg (2 GP, $2.3\times10^4$ and $3.1\times10^3$ PFU/mL) and favipiravir groups (1GP, $2.9\times10^4$).

Clinical scoring results for each guinea pig was assessed on a scale ranging from 1-4, where a score of 1 indicated a healthy animal and a score of 4 was indicative of a moribund animal. All animals in each group succumbed at least partially to disease by study day 8. See FIG. 11A. In each group the mean clinical observation increased inversely with survival, with each pyronaridine-treated group having two independent increases in average clinical observations. Interestingly, during post-study day 8 the average clinical score in the favipiravir group seemed to be independent of survival. See FIG. 11C.

Example 8

Favipiravir and Pyronaridine In Vivo Efficacy Using a Meta-Analysis Control

In order to increase the statistical power of the study, the favipiravir, positive-control data were combined from two individual experiments (n=6, n=10) as these used comparable approaches and were performed by the same group. The negative control varied between experiments, both in frequency of administration and vehicle formulation and were therefore not combined.

Figure 11B:
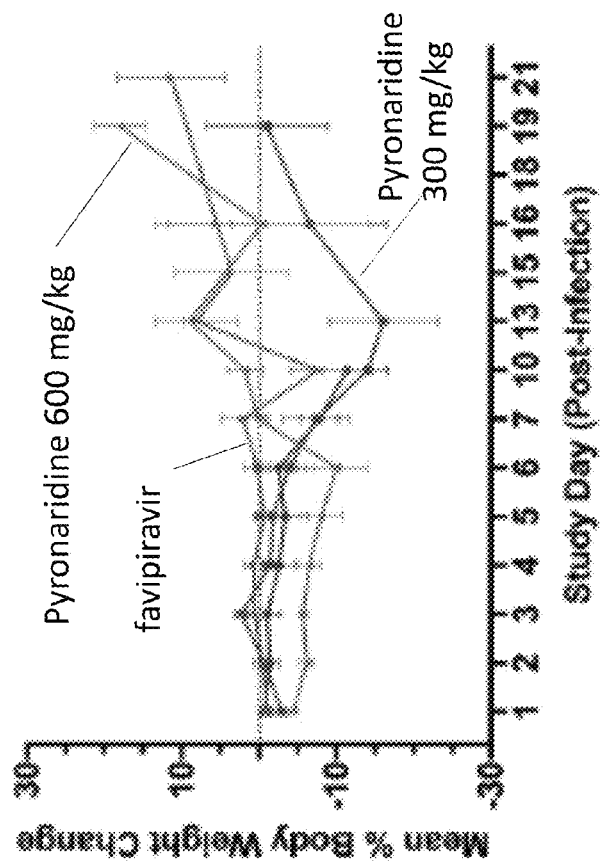
FIG. 11B is a graph showing the mean percent (%) body weight change (versus body weight at the time of infection) in guinea pigs as a function of time (in days) post infection with guinea pig Ebola virus (gaEBOV) in guinea pigs treated once with 300 milligrams per kilogram (mg/kg) or 600 mg/kg pyronaridine, once a day with favipiravir, or vehicle.
Figure 11A:
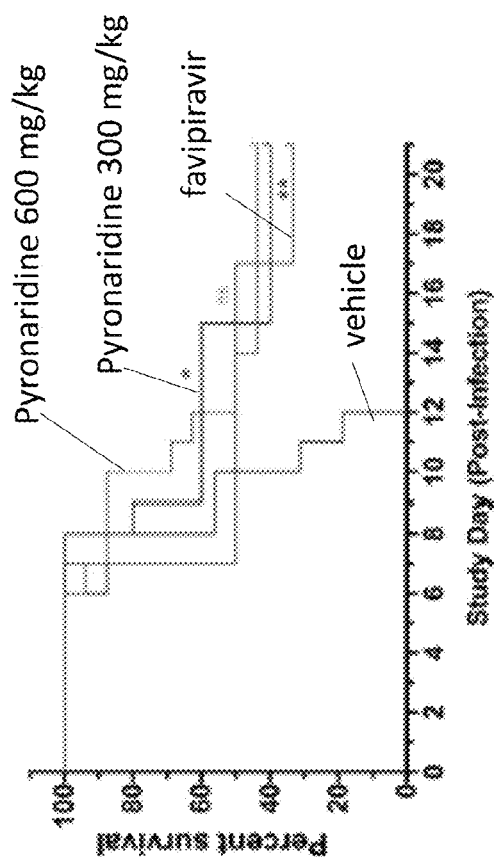
FIG. 11A is a graph showing the survival curves of guinea pigs infected with guinea pig Ebola virus (gpEBOV) and dosed once with pyronaridine (300 milligrams per kilogram (mg/kg) or 600 mg/kg), once a day with favipiravir, or vehicle. The difference from vehicle was not significant (Log-rank (Mantel-Cox) test). Data from two favipiravir groups (n=16 combined) from independent studies were combined to strengthen predictive power.
Figure 11D:
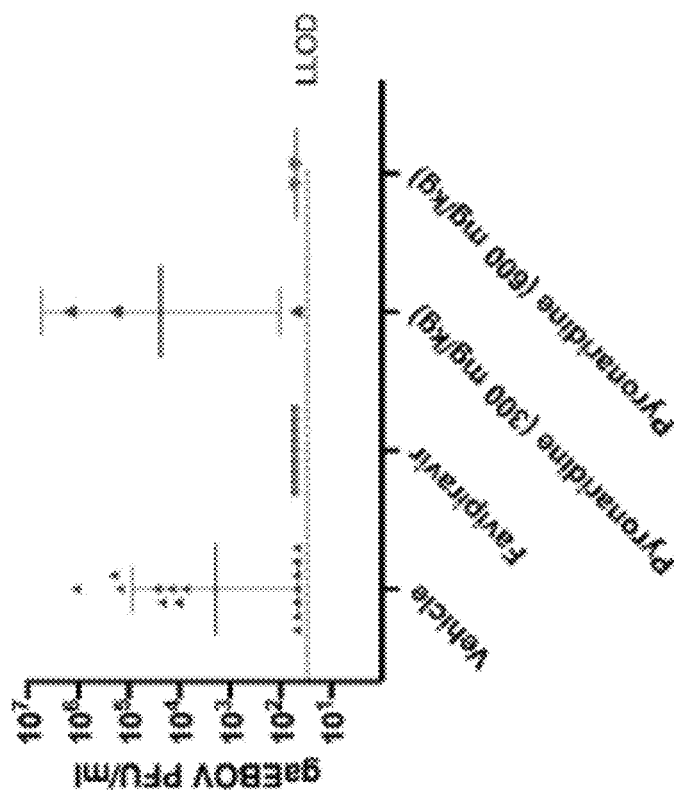
FIG. 11D is a graph showing the results of a plaque assay for viable Ebola virus (EBOV) in sera from guinea pigs sacrificed based on clinical score with Dunnett's T3 multiple comparisons test. Data is provided as plaque forming units per milliliter (PFU/ml) in EBOV infected guinea pigs treated with vehicle, once a day with favipirivir, once with 300 milligrams per kilogram (mg/kg) pyronaridine, or 600 mg/kg pyronaridine. Statistical significance was calculated with log-transformed plaque assay data using a Dunnett's T3 multiple comparisons test (Forsythe and Welch ANOVA) with the vehicle designated as the control. The difference from the vehicle was not found to be significant. For the plaque assay gaEBOV viral load had a lower limit of detection (LLOD) of 100 PFU/ml. Quantified values below these where set to 0.5×LLOD. Bars and error-bars represents the geometric mean and geometric SD.
Figure 11C:
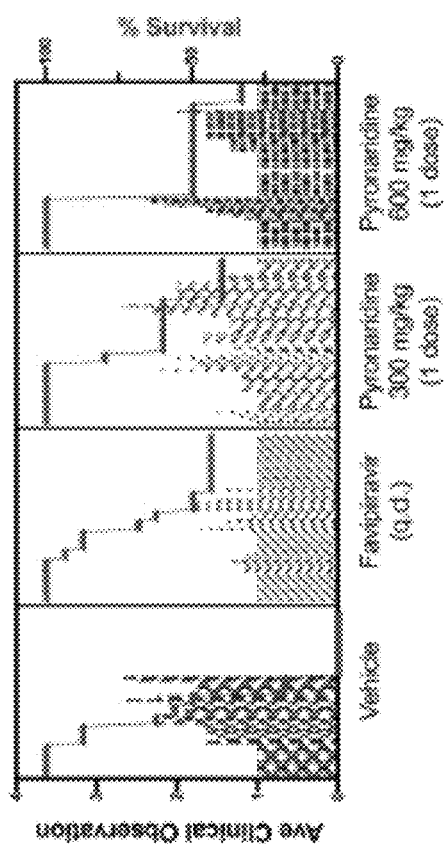
FIG. 11C is a graph showing the mean clinical scoring results (bars, on a scale of 0 to 4) overlaid with percent survival (line) in guinea pigs infected with guinea pig Ebola virus (gaEBOV) and treated with vehicle, once a day with favipiravir, once with 300 milligrams per kilogram (mg/kg) pyronaridine, or once with 600 mg/kg pyronaridine.
Figure 12A:
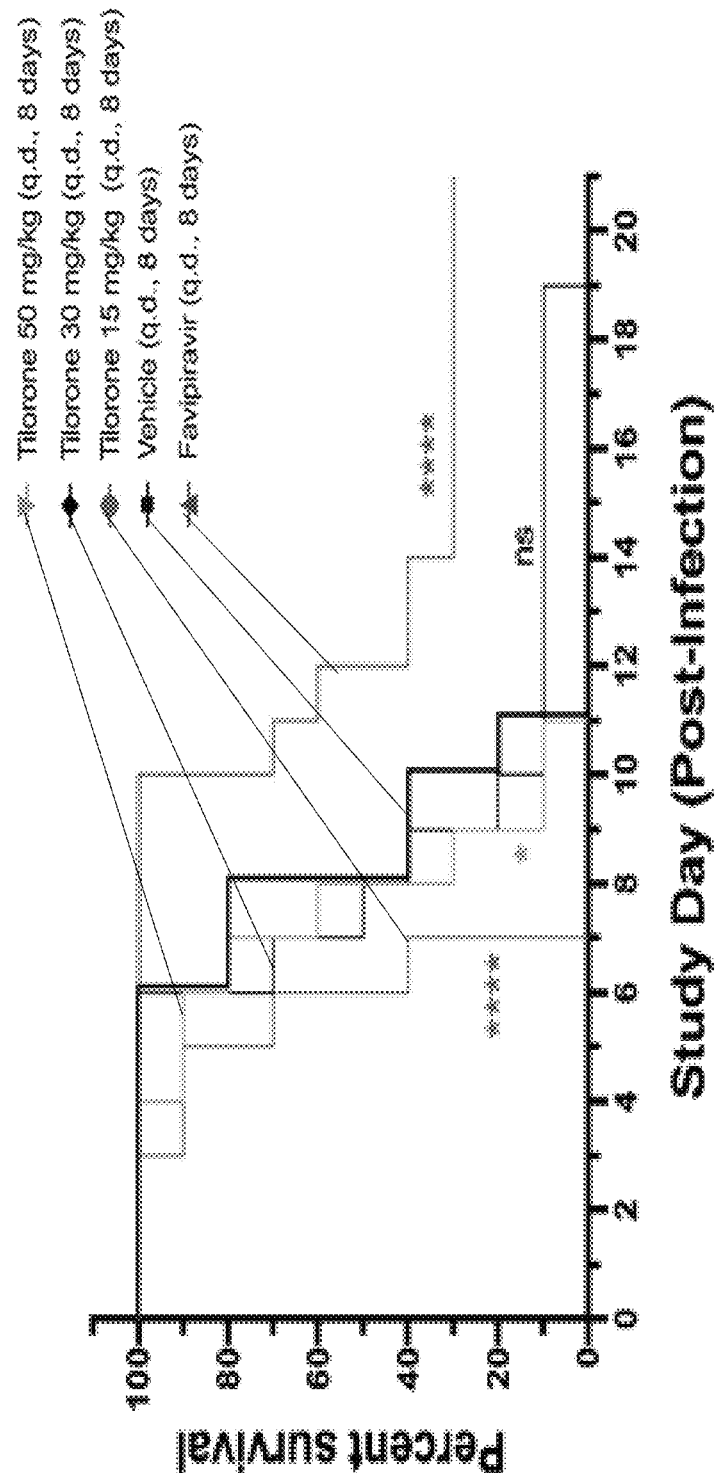
FIG. 12A is a graph showing survival curves of guinea pigs infected with guinea pig Ebola virus (gpEBOV) and dosed once a day for eight days with tilorone (15 milligrams per kilogram (mg/kg), 30 mg/kg or 50 mg/kg), favipiravir, or vehicle. Data from two favipiravir groups (n=16 combined) from independent studies were combined to strengthen predictive power. Asterisks represent significant difference from the vehicle (Log-rank (Mantel-Cox) test).
Figure 12B:
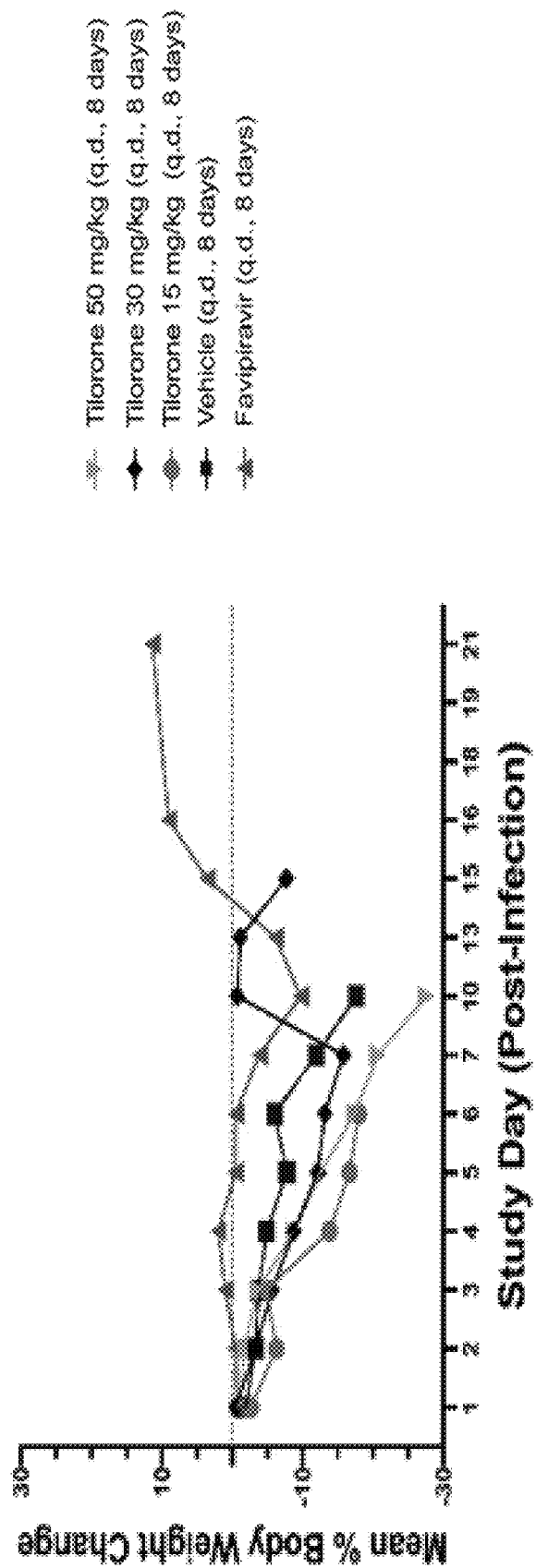
FIG. 12B is a graph of mean percent body weight change from study day 0 in guinea pigs as a function of time (in days) post infection with guinea pig Ebola virus (gaEBOV) in guinea pigs treated once a day for eight days with tilorone (15 milligrams per kilogram (mg/kg), 30 mg/kg or 50 mg/kg), favipiravir, or vehicle. Data from two favipiravir groups (n=16 combined) from independent studies were combined to strengthen predictive power.
Figure 12C:
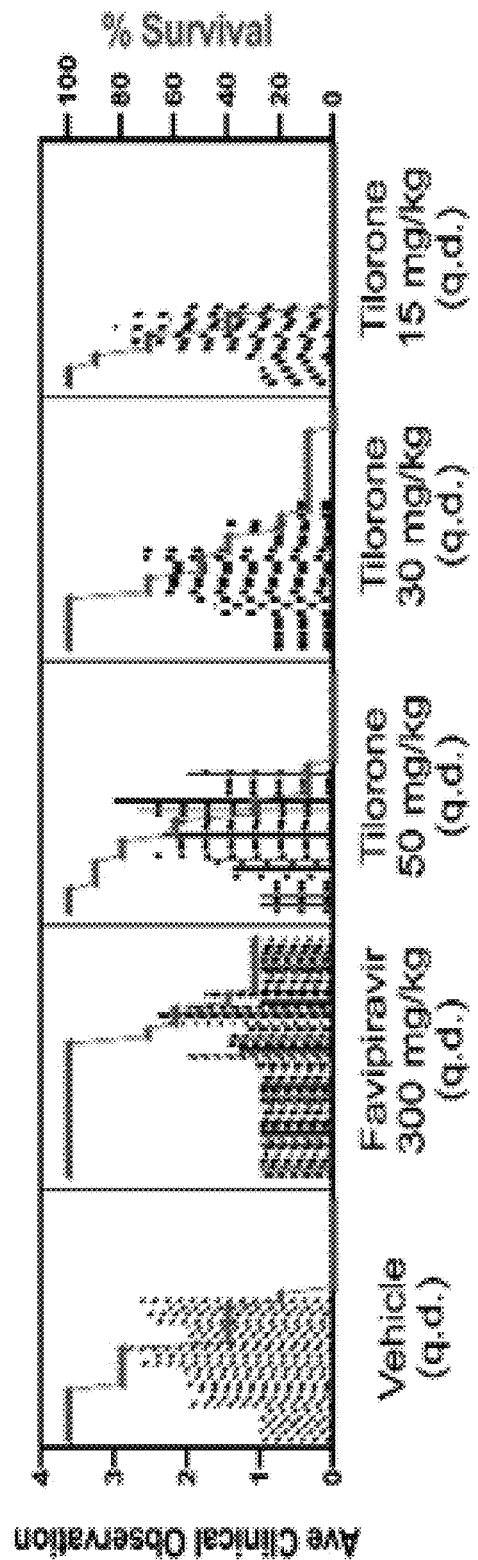
FIG. 12C is a graph showing the mean clinical scoring results (bars, on a scale of 0 to 4) overlaid with percent survival (line) in guinea pigs infected with guinea pig Ebola virus (gaEBOV) and treated once a day with vehicle, favipiravir, or 15 milligrams per kilogram (mg/kg), 30 mg/kg, or 50 mg/kg tilorone.
Figure 12D:
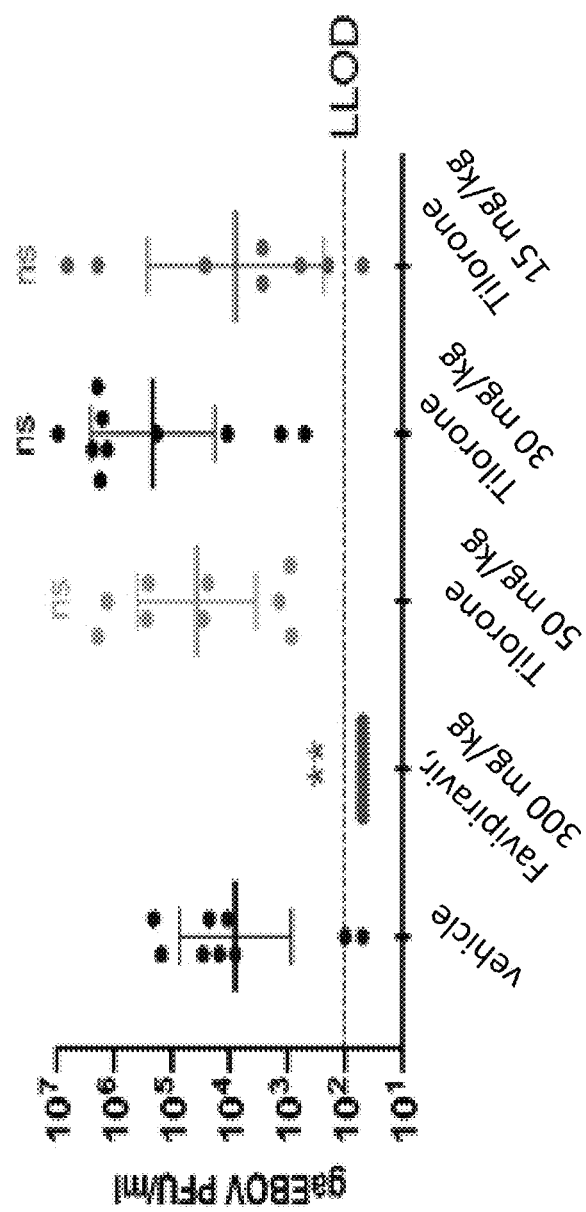
FIG. 12D is a graph showing the results of a plaque assay for viable guinea pig Ebola virus (gaEBOV) in sera from infected guinea pigs treated once a day with vehicle, favipiravir, or with 15 milligrams per kilogram (mg/kg), 30 mg/kg, or 50 mg/kg tilorone (guinea pigs sacrificed based on clinical score and scheduled sacrifice). Statistical significance was calculated with log-transformed plaque assay data using a Dunnett's T3 multiple comparisons test (Forsythe and Welch ANOVA) with the vehicle designated as the control. For the plaque assay, gaEBOV viral load had a lower limit of detection (LLOD) of 100 plaque forming units per milliliter (PFU/ml). Quantified values below these where set to 0.5×LLOD. Bars and error-bars represents the geometric mean and geometric standard deviation (SD).

Favipiravir has been shown to protect guinea pigs from adapted Sudan Virus (18); however it only protected ~44% of the animals against gpa-EBOV, with deaths starting on study day 6 and continuing until study day 14. See FIG. 11A. These were not statistically different from the treatment with pyronaridine 300 and 600 mg/kg with 40% and 33% survival, respectively (Log-rank (Mantel-Cox) test). Tilorone at the doses assessed were either comparable or had significantly reduced survival rates as compared to the vehicle. See FIG. 12A.

As there appeared to be a trend of an increased survival rate of pyronaridine and favipiravir compared to vehicle (see FIG. 11A) it was hypothesized that the lack of statistical significance could be based on the small study sizes (n=6, n=10) and a meta-analysis of published work performed in guinea pigs was performed. The survival rate of the negative controls from multiple EBOV-challenged GP studies (either untreated or oral vehicle treatment, n=55) (19-21) were combined with the data from the current studies to evaluate the possible statistical significance of the efficacy of pyronaridine and/or favipiravir. Evaluation of this "meta-analysis control" shows a significant difference for both pyronaridine 300 mg/kg and favipiravir (Log-rank (Mantel-Cox) test). See FIG. 13.

Interestingly, virus was only detected in serum samples collected at the time of euthanasia from one and two guinea pigs from the vehicle and pyronaridine 300 mg/kg, respectively, in the current pyronaridine study. This differed in the tilorone study (see FIGS. 9A-9C, 10, and 12A-12D) where virus was recovered from all but one serum sample harvested from the guinea pigs in the vehicle and tilorone-treated groups. See FIG. 12D. Virus was not detected in guinea pigs treated with favipiravir (both survivors and non-survivors) and was statistically significantly reduced from vehicle. See FIG. 11D.

Example 9

Guinea Pig Dose Range-Finding Toxicity for Tilorone

Guinea pigs in stratified groups were given vehicle (Group 1) or tilorone via oral gavage (po) with doses of 30 (Group 2), 100 (Group 3), 200/150 (Group 4) and 60 mg/kg (Group 5) q.d. for 7 days with 5 male and 5 female per group and assessed for survival. See FIG. 9A. Clinical observations were recorded once daily and approximately 2-4 hr post-dose on treatment days and on the day of necropsy. Animals were examined for any altered clinical signs, including gross motor and behavioral activity, and observable changes in appearance. Body weights were recorded for all animals on Day 1 (pre-dose), Day 4 (Groups 1, 2, 3 and 5) and prior to sacrifice. Group 4 animals that received 200 mg/kg of test article had multiple deaths immediately post-dose, so the next dose level was reduced to 150 mg/kg. Due to significant deaths and moribund conditions this group was completely discontinued on day 3.

Treatment with tilorone at 30 or 60 mg/kg was relatively well tolerated, with all animals surviving to their scheduled necropsies except one male at 60 mg/kg, which was sacrificed in moribund condition. Animals at dose levels of 100 mg/kg and higher showed significant mortality and morbidity. The main clinical observations were hypoactive, hypothermia and slight to severe tremors in the treated groups. Based on mortality/morbidity at 60 mg/kg and higher, the maximum tolerated dose (MTD) is considered to be 30 mg/kg. See FIGS. 9A-9C.

Example 10

Guinea Pig Pharmacokinetics Evaluation of Tilorone

A pharmacokinetic profile was assessed for tilorone in guinea pigs at 30, 100, 200 mg/kg. See FIG. 9C. A PK profile was also determined for the 30 mg/kg group at a 7-day q.d. dosing schedule. See FIG. 9B. Comparison by respective dose showed there was no statistically significant in-group difference between male and female GPs or between a single and 7-day dosing regimen by sex. See FIG. 10. Tilorone had an initial rapid absorption phase, with the highest plasma concentrations reached soon after dose administration. The mean plasma drug concentrations in males and females of 30 mg/kg (Day 7), 100 mg/kg and 200 mg/kg had a second lower peak concentration at about 4 hr, followed by an elimination phase. The plasma drug levels were analyzed using noncompartmental modeling allowing for the calculation of pharmacokinetic parameters. See Table 11, below.

TABLE 11

Guinea pig pharmacokinetics evaluation of tilorone.

| Sex | Dose (mg/kg) | Day | $T_{1/2}$ (hr) | $T_{max}$ (hr) | $C_{max}$ (ng/ml) Mean | SE | $AUC_{last}$ (hr · ng/ml) Mean | SE |
|---|---|---|---|---|---|---|---|---|
| Male | 30 | 1 | 15.6 | 1 | 148 | 28.5 | 1020 | 145 |
| Male | 30 | 7 | 13.3 | 0.5 | 137 | 34.5 | 1230 | 177 |
| Female | 30 | 1 | 14.3 | 1 | 220 | 66.8 | 1340 | 145 |
| Female | 30 | 7 | NC | 0.5 | 246 | 78.5 | 1140 | 195 |
| Male | 100 | 1 | NC | 1 | 225 | 25.1 | 2690 | 193 |
| Male | 200 | 1 | 29.0 | 1 | 355 | 127 | 5750 | 603 |
| Female | 100 | 1 | 17.4 | 1 | 384 | 92.0 | 3330 | 412 |
| Female | 200 | 1 | NC | 1 | 448 | 122 | 4680 | 276 |

Example 11

Tilorone In Vivo Efficacy, Clinical Observations and Scoring

Tilorone failed to protect guinea pigs from gpaEBOV at the dosages used. See FIG. 12A. Animals in the vehicle alone group succumbed to disease between Days 5 and 10. Guinea pigs receiving 15 mg/kg of tilorone succumbed at a faster rate than the vehicle control and all were dead by study day 7. Animals receiving 50 or 30 mg/kg of tilorone mirrored the vehicle controls with the exception of one guinea pig that was euthanized on Study Day 18 due to body weight loss.

All groups showed a reduction in mean body weight after challenge. See FIG. 12B. In fact, 19 animals were euthanized because they met the weight loss criteria. These were spread across the different groups suggesting that the virus challenge rather than the test and control articles was responsible for the weight loss. The guinea pig that was euthanized at Day 18 in the 30 mg/kg tilorone group started to lose weight on Day 15 and it continued to decrease on Day 18.

Blood was collected at non-scheduled euthanasia. The geometric mean titer of the combined vehicle control group was $8.02 \times 10^3$ PFU/mL. All guinea pigs receiving tilorone had similar geometric mean group titers that ranged from $7.887 \times 10^3$-$13.724 \times 10^4$ PFU/mL. See FIG. 12D.

Animals receiving tilorone mirrored the vehicle control group with clinical scores starting to increase on study day 5. See FIG. 12C. The guinea pig that survived the longest in the 30 mg/kg tilorone group scored a 2 on Days 5-7 then returned to normal (score of 1) until Day 18 when it scored a 3 and was euthanized because of weight loss. Animals receiving favipiravir scored a 1 through the treatment period then the group started showing signs of disease between Day 8 and 9. The three animals that survived to the end of the study returned to normal by Day 12. Guinea pig 15 from this group scored a 1 throughout the study.

Example 12

Ebola Glycoprotein Binding

Additional Materials:

Toremifene and clomiphene were purchased from MedChemExpress (Monmouth Junction, N.J., United States of America), and favipiravir was from TRC Canada (North York, Canada). Zaire ebolavirus disulfide-linked glycoprotein heterodimer (GP1-GP2) was purchased from Novus Biologicals (Centennial, Colo., United States of America). According to the manufacturer, EBOV GP protein is purified from CHO-derived viral expression with previous internal verification of significant glycosylation.

Microscale Thermophoresis:

An amount of 200 µg of lyophilized protein was resuspended in RED-NHS second Generation labeling buffer (Nanotemper Technologies, Munich, Germany). This was followed by the labeling of the primary amines using the RED-NHS dye according to the manufacturer's protocol. Labeled protein was buffer exchanged into 10 mM MES, pH 5.0, 150 mM NaCl, 170 mM sodium malonate at pH 5.2 (MST buffer), and then diluted to a final concentration of 1 µM. For each compound, 16 independent stocks were made in DMSO using 2-fold serial dilution (10 mM initial concentration). The MST buffer used for a final dilution prior to MST was supplemented with 0.05% Tween 20 and 10 mM BME. The protein was diluted to 2.5 nM in the supplemented MST buffer, and 19.5 µL of this was combined with 0.5 µL of the compound stock and then mixed thoroughly. This resulted in 2-fold serial dilution testing series with the highest and lowest concentrations of 250 µM and 7.629 nM, respectively, with a consistent final DMSO concentration of 2.5%. These reactions were incubated for 20-30 min prior to transferring to standard Monolith NT.115 capillaries (Nanotemper Technologies, Munich, Germany). Experiments were run at 20% excitation and high MST power at 23.0° C. on a Monolith NT.115Pico instrument (Nanotemper Technologies, Munich, Germany). Favipiravir and toremifene were also run as the negative and positive controls, respectively.

The data were acquired with MO.Control 1.6.1 (NanoTemper Technologies, Munich, Germany). Recorded data were analyzed with MO.Affinity Analysis 2.3 (NanoTemper Technologies, Munich, Germany). The dissociation constant $K_d$ quantifies the equilibrium of the reaction of the labelled molecule A (concentration $c_A$) with its target T (concentration $C_T$) to form the complex AT (concentration $c_{AT}$): and is defined by the law of mass action as:

$$K_d = \frac{c_A \times c_T}{C_{AT}},$$

where all concentrations are "free" concentrations. During the titration experiments the concentration of the labelled molecule A is kept constant and the concentration of added target T is increased. These concentrations are known and can be used to calculate the dissociation constant. The free concentration of the labelled molecule A is the added concentration minus the concentration of formed complex AT. The $K_d$ is calculated as $$Kd = \frac{(c_A^0 - c_{AT}) \times (c_t^0 - c_{AT})}{c_{AT}}.$$

The traction of bound molecules x can be derived from $F_{norm}$, where $F_{norm}(A)$ is the normalized fluorescence of only unbound labelled molecules A and $F_{norm}(AT)$ is the normalized fluorescence of complexes AT of labeled as shown by the equation:

$$x = \frac{F_{norm}(c_T^0) - F_{norm}(A)}{F_{norm}(AT) - F_{norm}(A)}.$$

The MST traces that showed aggregation or outliers were removed from the datasets prior to Kd determination.

Discussion

Figure 14A:
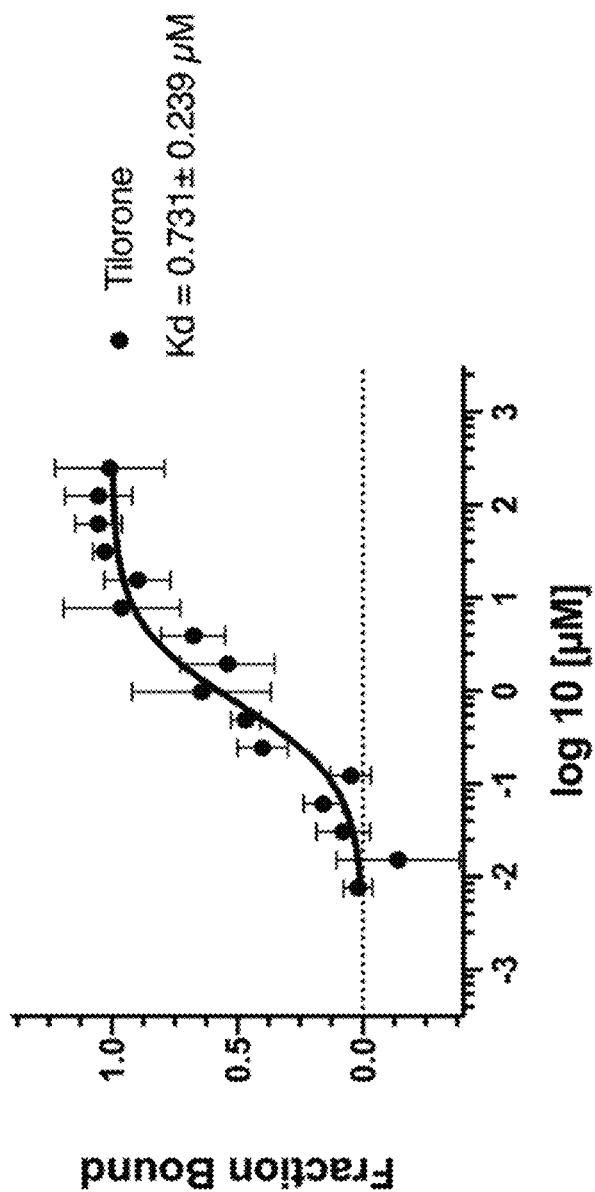
FIG. 14A is a graph showing Ebola glycoprotein dissociation constant (Kd) values generated using microscale thermophoresis data for tilorone.
Figure 14B:
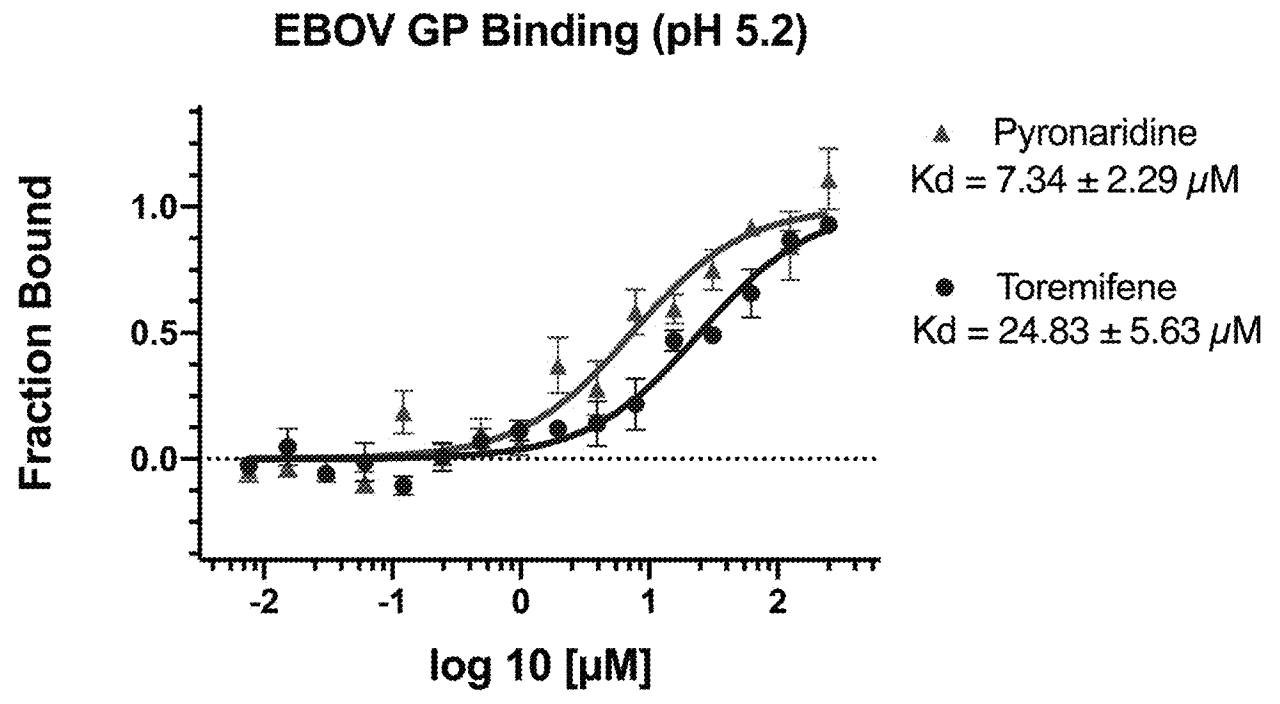
Figure 14C:
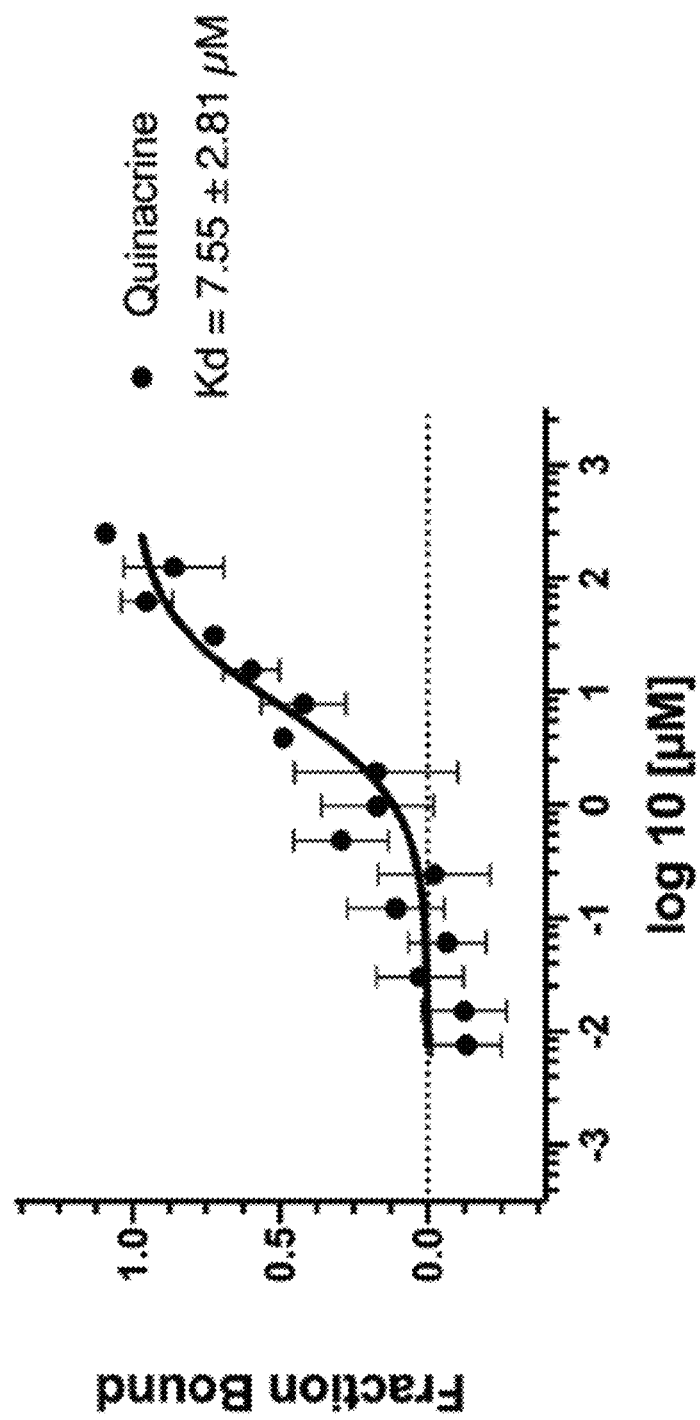
FIG. 14C is a graph showing the Ebola glycoprotein dissociation constant (Kd) value generated using microscale thermophoresis data for quinacrine.

Using microscale thermophoresis, Kd values were generated for tilorone (0.73 µM, see FIG. 14A), pyronaridine (7.34 µM; see FIG. 14B), and quinacrine (7.55 µM, see FIG. 14C). These molecules bind with a higher affinity that the previously reported toremifene (16 µM), which was used as a positive control. See FIG. 14B. Additionally, it was found that clomiphene (an ovulatory stimulator) binds to EBOV glycoprotein (Kd=30.74 µM) while favipiravir and artesunate did not.

The sequence of Ebola and Marburg glycoproteins were compared calculated using the Needleman-Wunsch algorithm. These resulted in an identity 236/763 (30.9%), similarity 323/763 (42.3%) and gaps 169/763 (22.1%). While these comparisons are low, when the binding site of the glycoprotein 2 structures are compared there is a <1 angstrom RMS which would suggest they are quite similar. Accordingly, it is believed to be reasonable to infer from the Ebola glycoprotein Kd data that these compounds can bind similarly to the MARV glycoprotein, destabilizing the glycoprotein and preventing cell entry.

Example 13

Discussion of Examples 1-12

There have been very few small molecule drugs that have reached the clinic for testing against EBOV, including favipiravir (22), GS-5734 (remdesivir) (17) and galidesivir (9). Once daily IV dosed remdesivir has demonstrated 100% survival in non-human primates only (25) and on this basis is being tested in humans during the current outbreak. Recently, a significant portion of data was described (499 individuals) from a clinical trial involving the investigation of multiple therapeutics against EBOV (NCT03719586) with ZMapp (a monoclonal antibody cocktail) (26)), remdesivir, MAb114 (a monoclonal antibody) (27)) and REGN-EB3 (monoclonal antibody combination) (28)). These preliminary results showed that the antibodies REGN-EB3 and mAb114 had overall survival rates of 71% and 66%, respectively, and were much more effective with patients with low viremia levels. Both ZMapp and remdesivir were shown to be less effective with a 51% and 47% survival rates, respectively (10). Ebola generally has a wide variation in its fatality rates of between 25% to 90%, (average ~50%). While these results are promising for the monoclonal antibodies, the delivery and administration of likely temperature sensitive treatments to remote areas in Africa is a potential issue. A highly stable small molecule drug that could be given orally as a single dose would be ideal and alleviate some of these logistical challenges that constitute the critical final stage of delivering a therapeutic to the patient.

From this present study, pyronaridine and other drugs, particularly tilorone and quinacrine, have shown activity in several strains of EBOV and MARV in vitro, indicating they can have a broad-spectrum activity against the virus family Filoviridae. Based on pseudovirus data these compounds appear to be preventing entry of the virus. See FIG. 1. They were also found to bind to Ebola glycoprotein more potently than previously described molecules, suggesting that they can prevent viral cell entry by destabilizing the viral glycoprotein.

Two of these drugs were studied further in the guinea pig model of EBOV infection. Pyronaridine did not show as substantial of a difference in survival rate in guinea pig as was observed for mouse. Without being bound to any one theory, this is attributed to the shorter half-life for pyronaridine in the guinea pig, such that efficacious plasma levels of drug are likely not maintained long enough (90 hrs). The pharmacokinetics varies in other species, where the half-life in mice and humans is approximately 140 hours and 200 hours, respectively. Many small molecules have failed to progress beyond guinea pig for treating Ebola due to a lack of significant efficacy (4, 19, 21, 29, 30). While antibodies have been successfully used in this model (31, 32), these failures appear to represent a limitation of the guinea pig model to extrapolate small-molecule efficacy against EBOV in humans. There are metabolic stability differences between mouse, non-human primate, human and guinea pig (13), with the latter having a lower metabolic stability for pyronaridine. Again, without being bound to any one theory, this could be one explanation of why several drugs perform well in the mouse but fail in the guinea pig. While it is believed that this has not been determined for favipiravir, it has been shown that the pharmacokinetics of this compound exhibit nonlinearity over dose and time in non-human primates (33), making interspecies comparisons potentially much more complex. Based on this in vitro data, it would appear that the metabolic stability of pyronaridine in the non-human primate can be poor, requiring a dose adjustment to retain efficacy in this model. For example, the dose determined from mouse studies can be doubled. Antibodies are not likely to be metabolized by the same drug metabolizing enzymes; therefore, they can show more universal efficacy across species.

Figure 13:
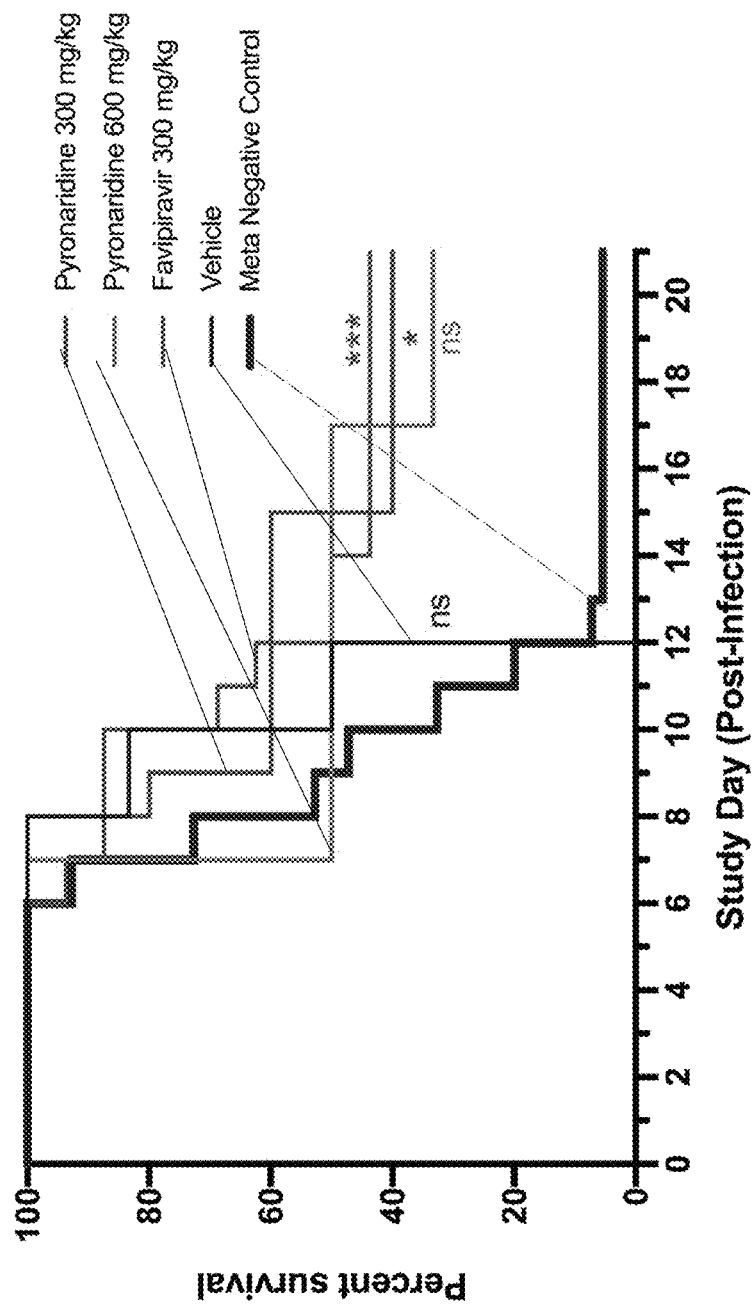
FIG. 13 is a graph showing survival curves for guinea pigs treated with pyronaridine (300 milligrams per kilogram (mg/kg) or 600 mg/kg), favipiravir, vehicle (oral) and meta-vehicle control. Data from favipiravir (combined, n=16) groups were combined from two independent studies in order to strengthen their predictive power. In addition, the meta-negative control is from four additional independent studies, representing the comprehensive comparable literature guinea pig negative control data (guinea pigs were either untreated or treated with a vehicle administered via oral gavage, n=55). Asterisks represent significant difference from the vehicle (Log-rank (Mantel-Cox) test).

Several drugs of interest have been studied in liver microsomes of various species under similar conditions. See Table 2. Tilorone also appears to have limited metabolic stability in guinea pig and is more stable in non-human primate and human liver microsomes. Chloroquine and quinacrine show different patterns across species. A comparison of metabolic stability with the substrate probe dextromethorphan also suggests a role of the CYP2D family in the metabolism of pyronaridine. It has been shown that pyronaridine inhibits known substrates of CYP2D6 both in vitro (8) and in vivo (34), suggesting that it could be a CYP2D6 substrate as well. As described herein, these data have been supplemented with detailed metabolite identification for each of pyronaridine, tilorone, quinacrine, and chloroquine for the first time. See FIGS. 4A-4C, 5A-5D, 6A-6d, and 7A-7D. See also Tables 5-8, above. It is unclear what effect EBOV infection has on the metabolic enzymes such as the P450's in the guinea pig. It is believed that favipiravir has not previously been tested orally against EBOV in guinea pig (though it has demonstrated survival rates of 83-100% in Sudan virus-infected guinea pigs (18)), and it has now been demonstrated to have efficacy on a par with what was observed in non-human primates (23, 24). In comparison, pyronaridine (300 and 600 mg/kg) was not significantly different from survival with oral-administered favipiravir in the guinea pig model ((Log-rank (Mantel-Cox) test), suggesting a similar efficacy. The presently disclosed subject matter takes a novel approach to create a meta-analysis control to increase the number of animals used as a negative control. This revealed a statistically significant difference for both pyronaridine and favipiravir when compared to the control. See FIG. 13. Initial dose ranging work showed toxicity with pyronaridine when dosed i.p. in guinea pig (accumulation in the abdominal cavity) hence the focus on oral administration. It should be noted that only a single dose of pyronaridine was used in the efficacy studies, and it is feasible that more frequent dosing and/or doubling the dose to overcome the lower half life will result in a higher exposure and subsequent increased survival rate.

In conclusion, the guinea pig in vivo data collected in this study points to ~40% survival for pyronaridine and favipiravir against gpa-EBOV, while the accumulated in vitro metabolic data indicates that the guinea pig can be a sub-optimal model to predict the efficacy of these compounds to combat the Ebola disease in humans. This could be due to differences in EBOV mechanism and drug metabolism (e.g. species differences in the metabolic enzymes involved (35, 36)). Overall, the combined in vitro and in vivo studies with pyronaridine demonstrate its potential utility for repurposing as an antiviral against different strains of EBOV and also for MARV.

Example 14

Additional Virus Screening

Pyronaridine tetraphosphate was also tested against representatives of the herpesviridae, bunyaviridae, togaviridae, arenaviridae, flavivirdae, picornaviridae, poxviridae, hepatic viruses, respiratory viruses and other viruses. Results are shown in Table 12. Pyronaridine was also found to be active against Nipah virus ($IC_{50}$=64 nM). Additional antiviral activity of tilorone and quinacrine are shown in Tables 13 and 14, respectively.

TABLE 12

In vitro virus testing of pyronaridine.

| | Cell line | $EC_{50}$ (μM) | $EC_{90}$ (μM) | $CC_{50}$ (μM) | $SI_{50}$ | $SI_{90}$ |
|---|---|---|---|---|---|---|
| Herpes Simplex Virus 1 | HFF | >6 | >6 | 6.52 | <1 | <1 |
| Vaccinia Virus | HFF | >1.20 | >1.20 | 4.02 | <3 | <3 |
| Chikungunya virus | Vero 76 | 3.2 | | 3.2 | 1 | |

TABLE 12-continued

In vitro virus testing of pyronaridine.

| | Cell line | EC$_{50}$ (µM) | EC$_{90}$ (µM) | CC$_{50}$ (µM) | SI$_{50}$ | SI$_{90}$ |
|---|---|---|---|---|---|---|
| Dengue Virus 2 | Vero 76 | 3.2 | | 3.2 | 1 | |
| Ebola virus | Vero 76 | >1.3 | | 1.3 | 0 | |
| Influenza A virus H1N1 | MDCK | 3.2 | | 3.2 | 1 | |
| MERS coronavirus | Vero 76 | 3.2 | | 3.2 | 1 | |
| Poliovirus 3 | Vero 76 | 3.2 | | 3.2 | 1 | |
| Respiratory synactial virus | MA-104 | >7.5 | | 7.5 | 0 | |
| Rift Valley fever virus | Vero 76 | 3.2 | | 3.2 | 1 | |
| Tacaribe virus | Vero | >3.2 | | 3.2 | 0 | |
| Venezuelian equine encephalitis virus | Vero 76 | 1.8 | | 3.2 | 1.8 | |
| West Nile virus | Vero 76 | >24 | | 24 | 0 | |
| Yellow Fever virus | Vero 76 | 3.2 | | 3.2 | 1 | |
| Zika virus | Vero 76 | 3.2 | | 3.2 | 1 | |
| Zika virus | Huh7 | 3.2 | | 3.2 | 1 | |
| Norovirus | HG23 | 3.5 | 9.7 | >100 | 29 | 10 |
| Murine norovirus | RAW267.4 | >40 | >40 | >40 | 1 | 1 |
| Human cytomegalovirus | HFF | >1.2 | >1.2 | 3.17 | <3 | <3 |
| Hepatitis C virus | Huh7 | 0.78 | 1.71 | 0.89 | 1 | <1 |
| Hepatitis B virus | HepG2 2.2.15 | 4.52 | >100 | 3.54 | <1 | <1 |

TABLE 13

Additional in vitro Viral Testing of Tilorone.

| Virus | Strain | Genus | Type | Cell Line | EC$_{50}$ (µM) | CC$_{50}$ (µM) |
|---|---|---|---|---|---|---|
| EBOV[a] | Zaire | Filovirus | −ssRNA | HeLa | 0.23 | 6.5 |
| EBOV | Zaire | Filovirus | −ssRNA | Vero 76 | >11* | 11 |
| Influenza A virus H1N1 | California/07/20/09 | Influenza-virus | −ssRNA | MDCK | >19 | 19 |
| Tacaribe Virus | TRVL 11573 | Arenavirus (new world) | −/+ssRNA | Vero 76 | 29* | 32 |
| CHIKV | S27 (VR-67) | Alphavirus | +ssRNA | Vero 76 | 4.2* | 32 |
| MERS-CoV | EMC | Betacorona-virus | +ssRNA | Vero 76 | 3.7* | 36 |
| Poliovirus 3 | WM-3 | Enterovirus | +ssRNA | Vero 76 | >25* | 25 |
| VEEV | TC-83 | Alphavirus | +ssRNA | Vero 76 | 18* | 32 |
| Yellow Fever | 17D | Arbovirus | +ssRNA | Vero 76 | >12 | 12 |

[a]original anti-EVOV screen.
*In vitro antiviral data in Vero 76 cells can underestimate antiviral activity due to lacking IFN pathways.

TABLE 14

Additional in vitro Viral Testing of Quinacrine.

| Virus | Strain | Genus | Type | Cell Line | EC$_{50}$ (µM) | CC$_{50}$ (µM) |
|---|---|---|---|---|---|---|
| EBOV[a] | Zaire | Filovirus | −ssRNA | HeLa | 0.35 | 6.2 |
| EBOV | Zaire | Filovirus | −ssRNA | Vero 76 | >12.3* | 12.3 |
| CHIKV | S27 (VR-67) | Alphavirus | +ssRNA | Vero 76 | 3.2* | 10 |
| VEEV | TC-83 | Alphavirus | +ssRNA | Vero 76 | 4* | 15 |

[a]original anti-EVOV screen.
*In vitro antiviral data in Vero 76 cells can underestimate antiviral activity due to lacking IFN pathways.

Example 15

Screening Against SARS2

A549-ACE2 Cell Assay

Pyronaridine, tilorone, and quinacrine were tested for activity against SARS-CoV-2 (SARS-2) using the A549-ACE2 cell assay. More particularly, each compound was tested against SARS-2 using an 8-point dose response curve consisting of serial fourfold dilutions, starting at 10 µM. The same range of compound concentrations was also tested for cytotoxicity in uninfected cells.

MHV Assay

Pyronaridine, tilorone, and quinacrine were tested for activity against SARS-CoV-2 (SARS-2) using the murine hepatitis virus (MHV) model in murine delayed brain tumor (DBT) cells. More particularly, each compound was tested against MHV using an 8-point dose response curve consisting of serial fourfold dilutions, starting at 10 µM. The same range of compound concentrations was also tested for cytotoxicity in uninfected cells.

Expression and Purification of Spike RBD of SARS-CoV-2

A codon-optimized gene encoding for SARS-CoV-2 (331 to 528 amino acids, QI560558.1) was expressed in Expi293 cells (Thermo Fisher Scientific, Waltham, Mass.) with human serum albumin secretion signal sequence and fusion tags (6×Histidine tag, Halo tag, and TwinStrep tag). S1 RBD was purified from the culture supernatant by nickel-nitrilotriacetic acid agarose (Qiagen, Hilden, Germany), and purity was confirmed to by >95% as judged by coomassie stained SDS-PAGE. The purified RBD protein was buffer exchanged to 1×PBS prior to analysis by Microscale Thermophoresis.

Microscale Thermophoresis

Experiments were performed using a Monolith Pico microscale thermophoresis instrument (Nanotemper Technologies, Munich, Germany). Briefly, 10 µM protein was labelled using Monolith Protein Labeling Kit RED-NHS 2$^{nd}$ Generation (Amine Reactive) (Nanotemper Technnologies, Munich, Germany), with 3-fold excess NHS dye in PBS (pH 7.4). Free dye was removed according to manufacturer's instruction, and protein was eluted in MST buffer (HEPES 10 mM pH 7.4, NaCl 150 mM), and centrifuged at 15 k rcf for 10 min. Binding affinity measurements were performed using 5 nM protein a serial dilution of compounds, starting at 250 µM. For each experimental compound, 16 independent stocks were made in DMSO using 2-fold serial dilution (10 mM initial concentration). 19.5 µL of Spike RBD (5 nM) of labeled protein in MST buffer containing 0.1% Triton X-100 and 1 mM BME was combined with 0.5 µL of the compound stock and then mixed thoroughly. This resulted in 2-fold serial dilution testing series with the highest and lowest concentration of 250 µM and 7.629 nM, respectively, with a consistent final DMSO concentration of 2.5%. Protein was incubated on ice in presence of compounds for one hour prior to transferring to standard Monolith NT.115 capillaries (NanoTemper Technologies, Munich, Germany). Experiments were run at 20% excitation and high MST power at 23.0° C. on a Monolith NT.115Pico microscale thermophoresis instrument (NanoTemper Technologies, Munich, Germany). Each experimental compound was run in triplicate.

The data were acquired with MO.Control 1.6.1 (NanoTemper Technologies, Munich, Germany). Recorded data were analyzed with MO.Affinity Analysis 2.3 (NanoTemper Technologies, Munich, Germany). The dissociation constant $K_d$ quantifies the equilibrium of the reaction of the labelled molecule A (concentration $c_A$) with its target T (concentration $c_T$) to form the complex AT (concentration $C_{AT}$): and is defined by the law of mass action as:

$$K_d = \frac{c_A \times c_T}{C_{AT}},$$

where all concentrations are "free" concentrations. During the titration experiments the concentration of the labelled molecule A is kept constant and the concentration of added target T is increased. These concentrations are known and can be used to calculate the dissociation constant. The free concentration of the labelled molecule A is the added concentration minus the concentration of formed complex AT. The $K_d$ is calculated as $$Kd = \frac{(c_A^o - c_{AT}) \times (c_t^o - c_{AT})}{c_{AT}}.$$

The traction of bound molecules x can be derived from $F_{norm}$, where $F_{norm}(A)$ is the normalized fluorescence of only unbound labelled molecules A and $F_{norm}(AT)$ is the normalized fluorescence of complexes AT of labeled as shown by the equation:

$$x = \frac{F_{norm}(c_T^o) - F_{norm}(A)}{F_{norm}(AT) - F_{norm}(A)}.$$

The MST traces that showed aggregation or outliers were removed from the datasets prior to Kd determination.

Discussion

Figure 15:
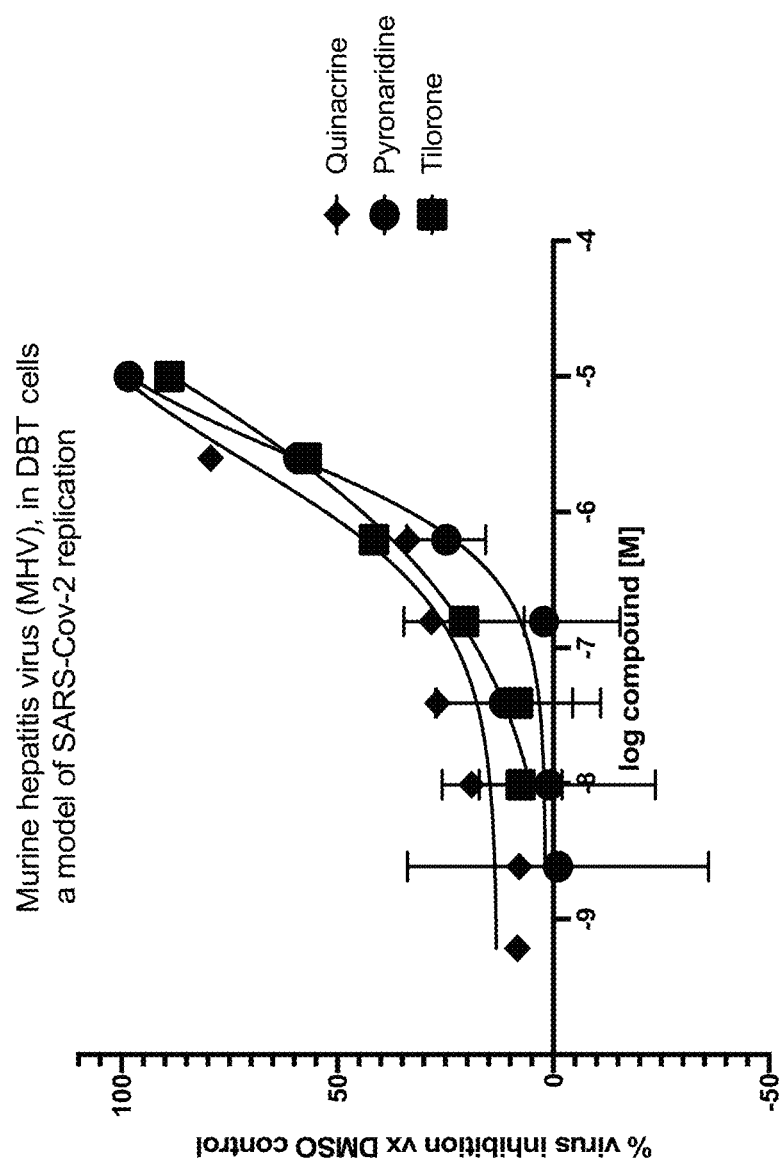
FIG. 15 is a graph showing the dose response curves for quinacrine (diamonds), pyronaridine (circles), and tilorone (squares) versus murine hepatitis virus (MHV) in murine delayed brain tumor (DBT) cells, a model of Severe Acute Respiratory Syndrome coronavirus 2 (SARS-Cov-2) replication. The 50% inhibitory concentrations ($IC_{50}$s) of quinacrine and pyronaridine were 2.3 micromolar (µM) and 2.75 µM, respectively. The tilorone dose response curve did not reach the plateau and the $IC_{50}$ was estimated to be 20 µM.
Figure 16B:
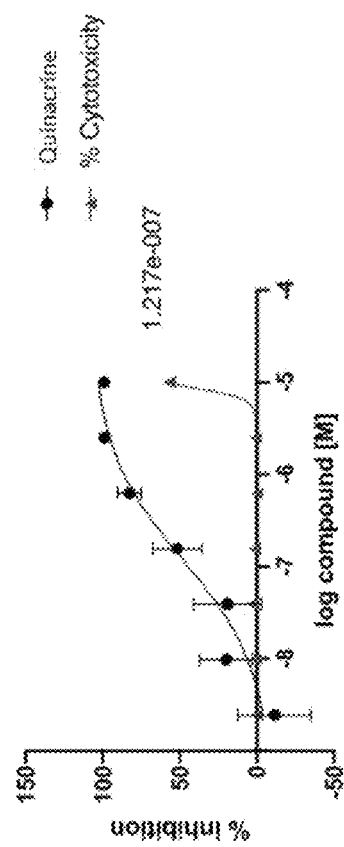
FIG. 16B is a graph showing quinacrine efficacy (circles) and cytotoxicity (triangles) dose response relationships against Severe Acute Respiratory Syndrome coronavirus 2 SARS-Cov-2) in A549-ACE2 cell lines. Quinacrine has a 50% inhibitory concentration ($IC_{50}$) of about 122 nanomolar (nM). Data is provided as percent inhibition versus log of the compound concentration (molar (M)).
Figure 16A:
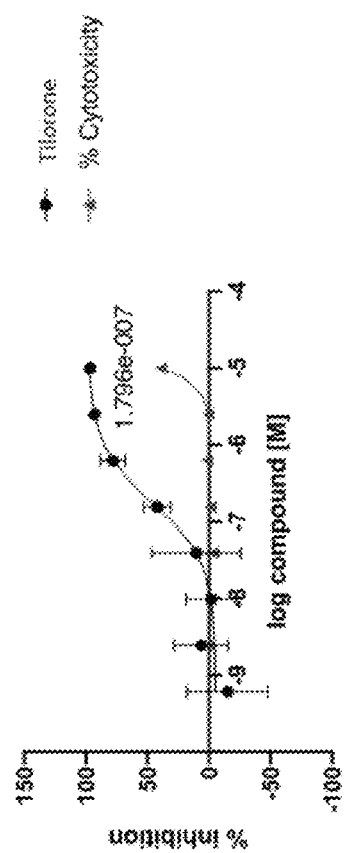
FIG. 16A is a graph showing tilorone efficacy (circles) and cytotoxicity (triangles) dose response relationships against Severe Acute Respiratory Syndrome coronavirus 2 SARS-Cov-2) in A549-ACE2 cell lines. Tilorone has a 50% inhibitory concentration ($IC_{50}$) of about 180 nanomolar (nM). Data is provided as percent inhibition versus log of the compound concentration (molar (M)).
Figure 16D:
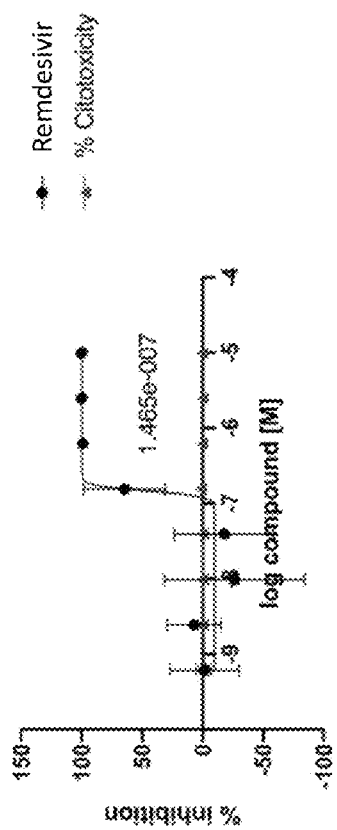
FIG. 16D is a graph showing remdesevir efficacy (circles) and cytotoxicity (triangles) dose response relationships against Severe Acute Respiratory Syndrome coronavirus 2 SARS-Cov-2) in A549-ACE2 cell lines. Remdesivir has a 50% inhibitory concentration ($IC_{50}$) of about 147 nanomolar (nM). Data is provided as percent inhibition versus log of the compound concentration (molar (M)).
Figure 16C:
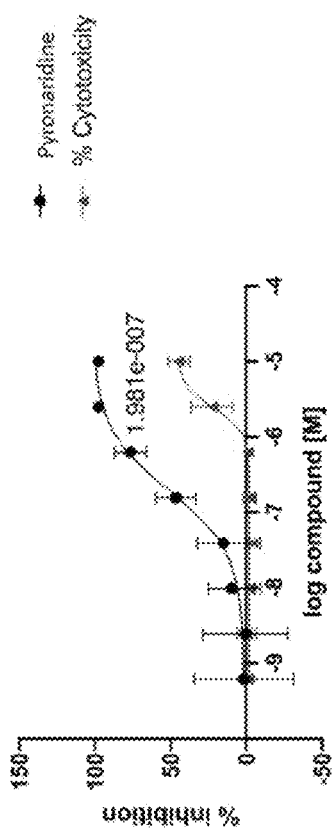
FIG. 16C is a graph showing pyronaridine efficacy (circles) and cytotoxicity (triangles) dose response relationships against Severe Acute Respiratory Syndrome coronavirus 2 SARS-Cov-2) in A549-ACE2 cell lines. Pyronaridine has a 50% inhibitory concentration ($IC_{50}$) of about 198 nanomolar (nM). Data is provided as percent inhibition versus log of the compound concentration (molar (M)).
Figure 17A:
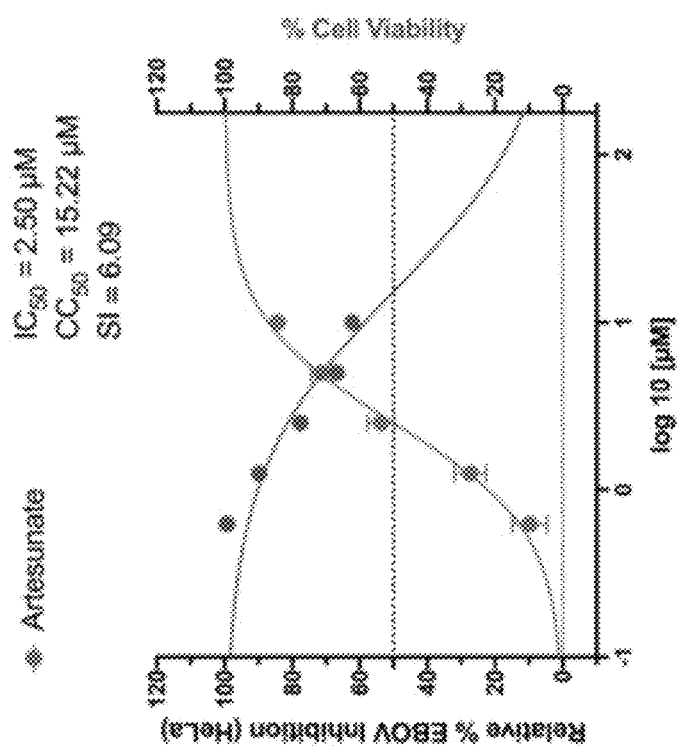
FIG. 17A is pair of graphs showing the inhibition/cytotoxicity plots for pyronaridine (left) and artesunate (right) controls (compound tested in the absence of the other compound). Controls were run in triplicate at 5 concentrations per plate, so the total number from replicates for each compound varied (Pyronaridine, n=27; Artesunate, n=18). Error bars represent the SEM at each concentration tested.
Figure 17A:
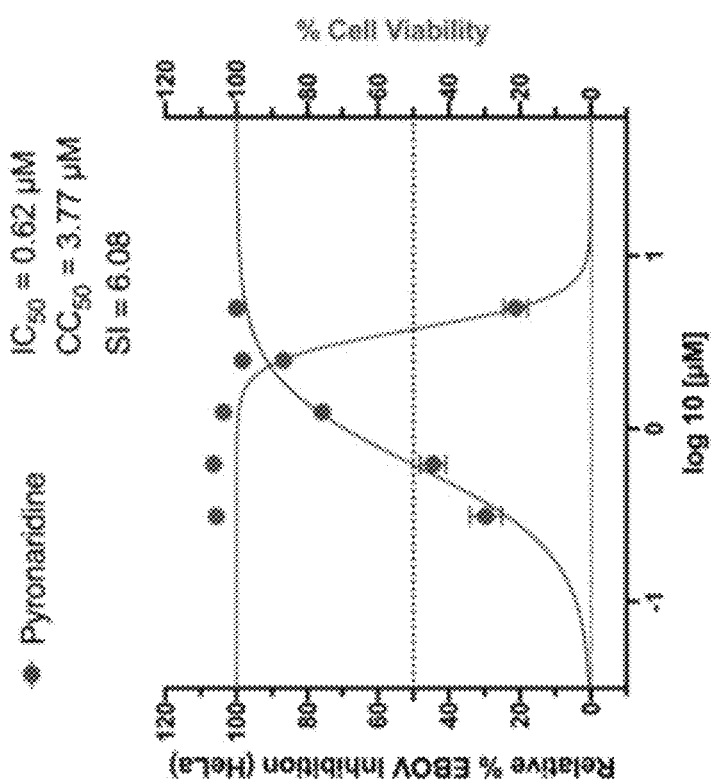
Figure 17B:
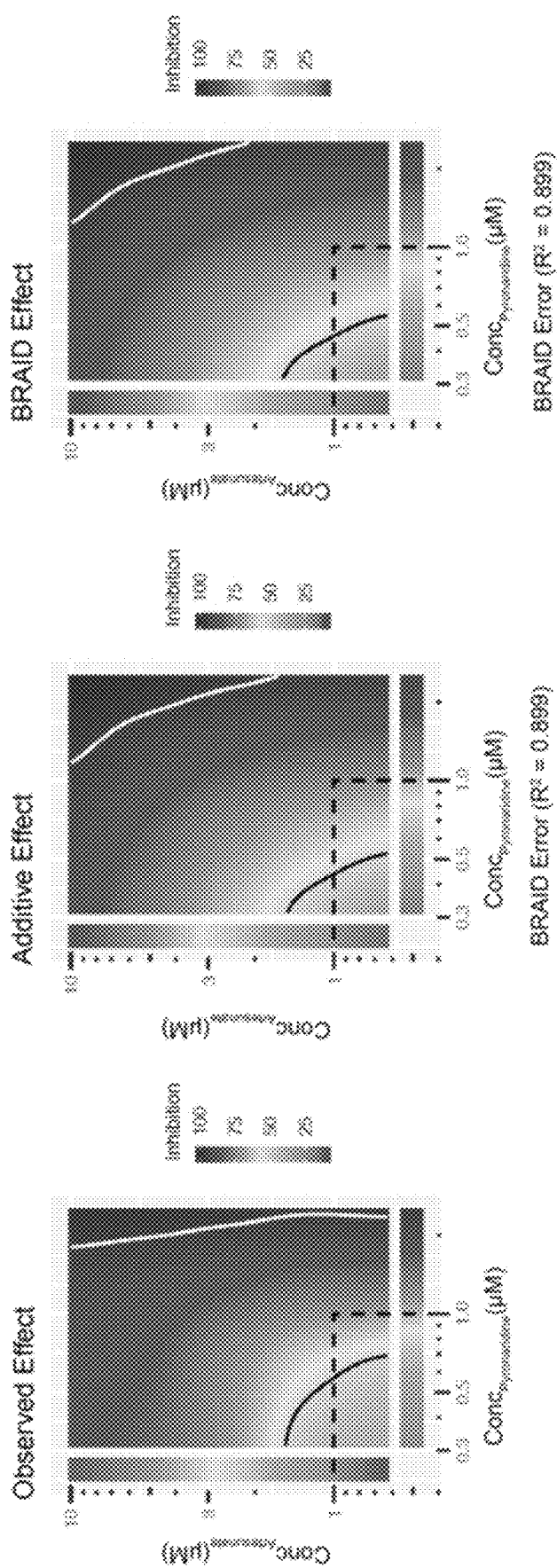
FIG. 17B is a series of graphs (from left to right) of the inhibition plots of the smoothed raw data, predicted additive inhibition and predicted inhibition using the 7-parameter BRAID analysis of pyronaridine and artesunate.
Figure 17C:
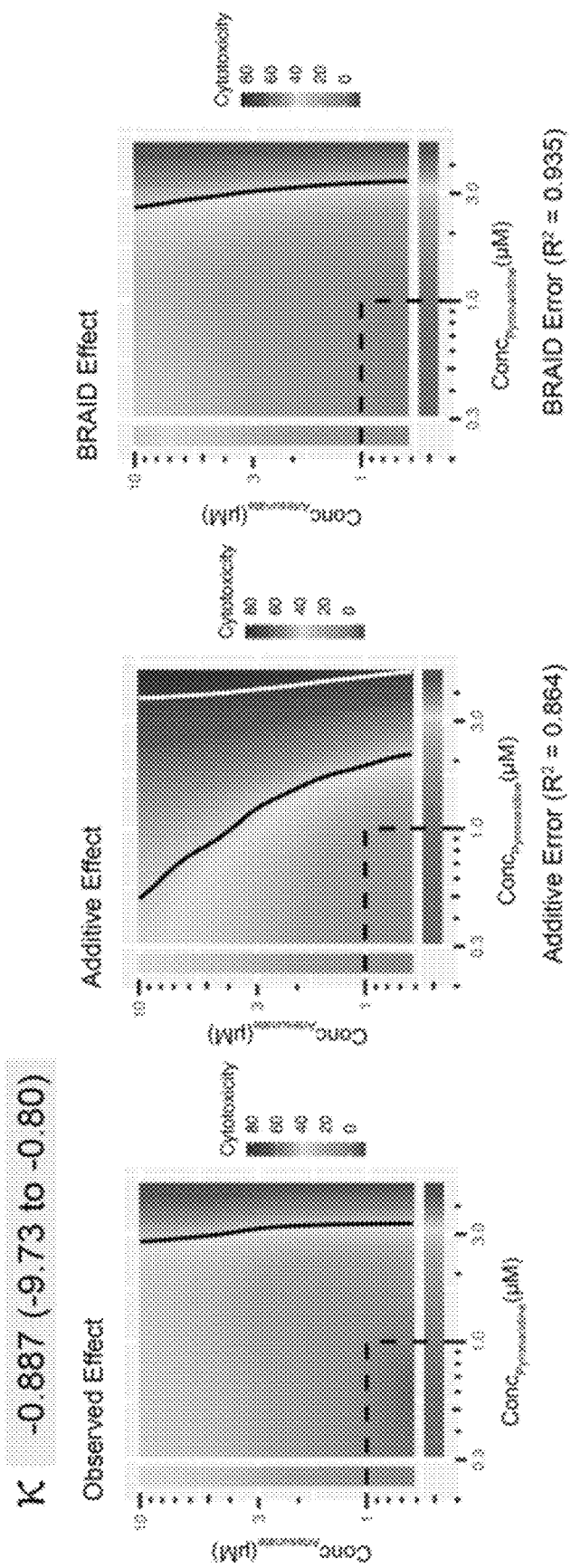
FIG. 17C is a series of graphs of the cytotoxicity plots (toxicity is representative of % cell death from control) from the 7-parameter BRAID analysis of pyronaridine and artesunate arranged in the same manner as inhibition plots described for FIG. 17B.

Tilorone, quinacrine, and pyronaridine were tested in a variety of different cell types. The most promising results were achieved in A549-ACE2 cells, in which quinacrine, tilorone and pyronaridine all showed SARS-CoV-2 inhibition demonstrating $IC_{50}$ values <200 nM (see FIGS. 16A-16D) and good selectivity indices. All the three compounds were tested against a murine hepatitis virus (MHV), in DBT cells, a model of SARS-CoV-2 replication. Quinacrine showed an $IC_{50}$ 2.3 µM, pyronaridine showed an $IC_{50}$ 2.75 µM while for tilorone the dose response curve did not reach the plateau and the $IC_{50}$ was estimated to be 20 µM. See FIG. 15.

Pyronaridine, tilorone and quinacrine were also tested against the SARS-CoV-2 Spike RBD. The $K_d$ values for tilorone and pyronaridine were of 339 nM and 647 nM, respectively at pH 7.4 and Kd 631 nM and 618 nM at pH5.2, respectively. Quinacrine did not demonstrate reproducible binding to this protein.

Example 16

In Vitro Combination Studies The in vitro infection inhibition of EBOV/Mak (Makona, IRF0165, 1.98E7 PFU/mL) was performed in HeLa. HeLa cells were seeded at 3×104 cells/well in 96-well plates. After 24 h the drugs were added to cells in a 6×6 matrix with 2-fold serial dilutions with a starting concentration of 30 μM. The experiment was run on 3-4 replicate plates. The experiment was run on 2 different days. Cells were infected with virus 1 h after the addition of the drugs in BSL4-containment at a multiplicity of infection (MOI) of 0.21 (Huh 7) or 0.5 (HeLa). After 48 h, plates were fixed and virus was detected with a mouse antibody specific for EBOV VP40 protein (#B-MD04-BD07-AE11, US Army Medical Research Institute of Infectious Diseases, Frederick, Md., United States of America) followed by staining with anti-mouse IgG peroxidase labelled antibody (KPL, Gaithersburg, Md., United States of America, #074-1802). Luminescence was read on a Spark 20M plate reader (Tecan US, Morrisville, N.C., United States of America). The signal of treated, infected wells was normalized to uninfected control wells and measured (in percent) relative to untreated infected wells. Non-linear regression analysis was performed, and the 50% inhibitory concentrations ($EC_{50}$s) were calculated from fitted curves (log [agonist] versus response [variable slope] with constraints to remain above 0% and not exceed 100%) (GraphPad Software version 8.0, GraphPad Software, La Jolla, Calif., United States of America). The EBOV drug screen assay was performed with three replicates for each drug concentration. Error bars of dose-response curves represent the SEM of the replicates.

For quantitation of drug toxicity, HeLa cells were mock infected (no virus) and treated with drug dilutions under the same conditions as the infected cells. After 48 h, cell viability was measured using a cell viability kit sold under the tradename CELLTITER-GLO™ Luminescent Cell Viability Assay kit (Promega Corporation, Madison, Wis., United States of America) according to manufacturer's protocol BRAID analysis (41) calculates synergy by fitting data to a seven-variable function. The variable K represents a quantitative synergy value where κ<0 implies antagonism, κ=0 implies additivity, and κ>0 implies synergy. As an additional reference, "strong synergy" corresponds to κ=2.5, "mild synergy" corresponds to κ=1, "mild antagonism" corresponds to κ=−0.66, and "strong antagonism" corresponds to κ=−1. To assess if the combined inhibitory effect of pyronaridine and artesunate on EBOV was synergistic, additive, or antagonistic, a 6×6 checkboard assay with this pair of drugs at various combined concentrations was analyzed in HeLa. It is noted that inhibition data under toxic concentrations (consistently >50% cell death) were removed from the analysis. Inclusively, this consisted of only individual and combined experiments with concentrations of pyronaridine that exceeded its $CC_{50}$ (i.e. 5 μM concentrations in HeLa cells only). All toxicity data was retained for BRAID analysis.

The BRAID analysis of pyronaridine and artesunate in vitro inhibition data from the checkerboard assay indicates additivity of these molecules in HeLa cells. See FIGS.

17A-17C. Artesunate ameliorates the toxicity of pyronaridine in the checkboard assay and therefore indirectly potentiates pyronaridine.

REFERENCES

The references listed below as well as all references cited in the specification are incorporated herein by reference to the extent that they supplement, explain, provide a background for or teach methodology, techniques and/or compositions employed herein. All cited patents and publications referred to in this application are herein expressly incorporated by reference.

1. Hernandez H W, Soeung M, Zorn K M, Ashoura N, Mottin M, Andrade C H, Caffrey C R, de Siqueira-Neto J L, Ekins S. 2018. High Throughput and Computational Repurposing for Neglected Diseases. Pharm Res 36:27.
2. Ekins S, Williams A J, Krasowski M D, Freundlich J S. 2011. In silico repositioning of approved drugs for rare and neglected diseases. Drug Discov Today 16:298-310.
3. Bai J P F, Hsu C W. 2019. Drug repurposing for Ebola virus disease: principles of consideration and the Animal Rule. J Pharm Sci 108:798-806.
4. Madrid P B, Panchal R G, Warren T K, Shurtleff A C, Endsley A N, Green C E, Kolokoltsov A, Davey R, Manger I D, Gilfillan L, Bavari S, Tanga M J. 2015. Evaluation of Ebola Virus Inhibitors for Drug Repurposing. ACS Infect Dis 1:317-26.
5. Kiley M P, Bowen E T, Eddy G A, Isaacson M, Johnson K M, McCormick J B, Murphy F A, Pattyn S R, Peters D, Prozesky O W, Regnery R L, Simpson D I, Slenczka W, Sureau P, van der Groen G, Webb P A, Wulff H. 1982. Filoviridae: a taxonomic home for Marburg and Ebola viruses? Intervirology 18:24-32.
6. Ekins S, Southan C, Coffee M. 2015. Finding small molecules for the 'next Ebola'. F1000Res 4:58.
7. Bornholdt Z A, Herbert A S, Mire C E, He S, Cross R W, Wec A Z, Abelson D M, Geisbert J B, James R M, Rahim M N, Zhu W, Borisevich V, Banadyga L, Gunn B M, Agans K N, Wirchnianski A S, Goodwin E, Tierney K, Shestowsky W S, Bohorov O, Bohorova N, Velasco J, Ailor E, Kim D, Pauly M H, Whaley K J, Alter G, Walker L M, Chandran K, Zeitlin L, Qiu X, Geisbert T W, Dye J M. 2019. A Two-Antibody Pan-Ebolavirus Cocktail Confers Broad Therapeutic Protection in Ferrets and Nonhuman Primates. Cell Host Microbe 25:49-58 e5.
8. Jonas O. 2019. Pandemic bonds: designed to fail in Ebola. Nature 572:285.
9. Taylor R, Kotian P, Warren T, Panchal R, Bavari S, Julander J, Dobo S, Rose A, El-Kaftan Y, Taubenheim B, Babu Y, Sheridan W P. 2016. BCX4430—A broad-spectrum antiviral adenosine nucleoside analog under development for the treatment of Ebola virus disease. J Infect Public Health 9:220-6.
10. Mulangu S, Dodd L E, Davey R T Jr, Tshiani Mbaya O, Proschan M, Mukadi D, Lusakibanza Manzo M, Nzolo D, Tshomba Oloma A, Ibanda A, Ali R, Coulibaly S, Levine A C, Grais R, Diaz J, Lane H C, Muyembe-Tamfum J J, Group P W, Sivahera B, Camara M, Kojan R, Walker R, Dighero-Kemp B, Cao H, Mukumbayi P, Mbala-Kingebeni P, Ahuka S, Albert S, Bonnett T, Crozier I, Duvenhage M, Proffitt C, Teitelbaum M, Moench T, Aboulhab J, Barrett K, Cahill R, Cone K, Eckes R, Hensley L, Herpin B, Higgs E, Ledgerwood J, Pierson J, Smolskis M, Sow Y, Tierney J, Sivapalasingam S, Holman W, Gettinger N, Vallee D, Nordwall J, Team P C S, 2019. A Randomized, Controlled Trial of Ebola Virus Disease Therapeutics. N Engl J Med 381, 2293-2303.
11. Ekins S, Freundlich J, Clark A, Anantpadma M, Davey R, Madrid P. 2015. Machine learning models identify molecules active against Ebola virus in vitro. F1000Res 4:1091.
12. Lane T R, corner J E, Freiberg A N, Madrid P B, Ekins S. 2019. Repurposing Quinacrine Against Ebola Virus Infection In vivo. Antimicrob Agents Chemother doi: 10.1128/AAC.01142-19.
13. Lane T R, Massey C, corner J E, Anantpadma M, Freundlich J S, Davey R A, Madrid P B, Ekins S. 2019. Repurposing The Antimalarial Pyronaridine Tetraphosphate To Protect Against Ebola Virus Infection PLoS Negl Trop Dis In Press.
14. Croft S L, Duparc S, Arbe-Barnes S J, Craft J C, Shin C S, Fleckenstein L, Borghini-Fuhrer I, Rim H J. 2012. Review of pyronaridine anti-malarial properties and product characteristics. Malar J 11:270.
15. Anantpadma M, Kouznetsova J, Wang H, Huang R, Kolokoltsov A, Guha R, Lindstrom A R, Shtanko O, Simeonov A, Maloney D J, Maury W, LaCount D J, Jadhav A, Davey R A. 2016. Large-Scale Screening and Identification of Novel Ebola Virus and Marburg Virus Entry Inhibitors. Antimicrob Agents Chemother 60:4471-81.
16. Jayaraman S D, Ismail S, Nair N K, Navaratnam V. 1997. Determination of pyronaridine in blood plasma by high-performance liquid chromatography for application in clinical pharmacological studies. J Chromatogr B Biomed Sci Appl 690:253-7.
17. Ramanathan S, Karupiah S, Nair N K, Olliaro P L, Navaratnam V, Wernsdorfer W H, Mansor S M. 2005. A new and simple solid-phase extraction method for L C determination of pyronaridine in human plasma. J Chromatogr B Analyt Technol Biomed Life Sci 824:45-50.
18. Rahim M N, Zhang Z, He S, Zhu W, Banadyga L, Safronetz D, Qiu X. 2018. Postexposure Protective Efficacy of T-705 (Favipiravir) Against Sudan Virus Infection in Guinea Pigs. J Infect Dis 218:S649-S657.
19. Dowall S D, Bosworth A, Watson R, Bewley K, Taylor I, Rayner E, Hunter L, Pearson G, Easterbrook L, Pitman J, Hewson R, Carroll M W. 2015. Chloroquine inhibited Ebola virus replication in vitro but failed to protect against infection and disease in the in vivo guinea pig model. J Gen Virol 96:3484-3492.
20. Chan M, Holtsberg F W, Vu H, Howell K A, Leung A, Van der Hart E, Walz P H, Aman M J, Kodihalli S, Kobasa D. 2018. Efficacy of Ebola Glycoprotein-Specific Equine Polyclonal Antibody Product Against Lethal Ebola Virus Infection in Guinea Pigs. J Infect Dis 218:S603-S611.
21. Dowall S D, Bewley K, Watson R J, Vasan S S, Ghosh C, Konai M M, Gausdal G, Lorens J B, Long J, Barclay W, Garcia-Dorival I, Hiscox J, Bosworth A, Taylor I, Easterbrook L, Pitman J, Summers S, Chan-Pensley J, Funnell S, Vipond J, Charlton S, Haldar J, Hewson R, Carroll M W. 2016. Antiviral Screening of Multiple Compounds against Ebola Virus. Viruses 8.
22. Sissoko D, Laouenan C, Folkesson E, M'Lebing A-B, Beavogui A-H, Baize S, Camara A-M, Maes P, Shepherd S, Danel C, Carazo S, Conde M N, Gala J-L, Colin G, Savini H, Bore J A, Le Marcis F, Koundouno F R, Petitjean F, Lamah M-C, Diederich S, Tounkara A, Poelart G, Berbain E, Dindart J-M, Duraffour S, Lefevre A, Leno T, Peyrouset O, Irenge L, Bangoura N F, Palich R, Hinzmann J, Kraus A, Barry T S, Berette S, Bongono A, Camara M S, Chanfreau Munoz V, Doumbouya L, Souley H, Kighoma P M, Koundouno F R, Rene L, Loua C M, Massala V, Moumouni K, Provost C, Samake N, Sekou C, Soumah A, Arnould I, Komano M S, Gustin L, Berutto C, Camara D, Camara F S, Colpaert J, Delamou L, Jansson L, Kourouma E, Loua M, Malme K, Manfrin E, Maomou A, Milinouno A, Ombelet S, Sidiboun A Y, Verreckt I, Yombouno P, Bocquin A, Carbonnelle C, Carmoi T, Frange P, Mely S, Nguyen V-K, Pannetier D, Taburet A-M, Treluyer J-M, Kolie J, Moh R, Gonzalez M C, Kuisma E, Liedigk B, Ngabo D, Rudolf M, Thom R, Kerber R, Gabriel M, Di Caro A, Wölfel R, Badir J, Bentahir M, Deccache Y, Dumont C, Durant J-F, El Bakkouri K, Gasasira Uwamahoro M, Smits B, Toufik N, Van Cauwenberghe S, Ezzedine K, Dortenzio E, Pizarro L, Etienne A, Guedj J, Fizet A, Barte de Sainte Fare E, Murgue B, Tran-Minh T, Rapp C, Piguet P, Poncin M, Draguez B, Allaford Duverger T, Barbe S, Baret G, Defourny I, Carroll M, Raoul H, Augier A, Eholie S P, Yazdanpanah Y, Levy-Marchal C, Antierrens A, Van Herp M, Günther S, de Lamballerie X, Keïta S, Mentre F, Anglaret X, Malvy D, Group J S. 2016. Experimental treatment with Favipiravir for Ebola Virus Disease (the JIKI Trial): A historically controlled, single-arm proof-of-concept trial in Guinea. PLOS Medicine 13:e1001967.
23. Bixler S L, Bocan T M, Wells J, Wetzel K S, Van Tongeren S A, Dong L, Garza N L, Donnelly G, Cazares L H, Nuss J, Soloveva V, Koistinen K A, Welch L, Epstein C, Liang L F, Giesing D, Lenk R, Bavari S, Warren T K. 2018. Efficacy of favipiravir (T-705) in nonhuman primates infected with Ebola virus or Marburg virus. Antiviral Res 151:97-104.
24. Guedj J, Piorkowski G, Jacquot F, Madelain V, Nguyen T H T, Rodallec A, Gunther S, Carbonnelle C, Mentre F, Raoul H, de Lamballerie X. 2018. Antiviral efficacy of favipiravir against Ebola virus: A translational study in cynomolgus macaques. PLoS Med 15:e1002535.
25. Siegel D, Hui H C, Doerffler E, Clarke M O, Chun K, Zhang L, Neville S, Carra E, Lew W, Ross B, Wang Q, Wolfe L, Jordan R, Soloveva V, Knox J, Perry J, Perron M, Stray K M, Barauskas O, Feng J Y, Xu Y, Lee G, Rheingold A L, Ray A S, Bannister R, Strickley R, Swaminathan S, Lee W A, Bavari S, Cihlar T, Lo M K, Warren T K, Mackman R L. 2017. Discovery and Synthesis of a Phosphoramidate Prodrug of a Pyrrolo[2,1-f][triazin-4-amino] Adenine C-Nucleoside (GS-5734) for the Treatment of Ebola and Emerging Viruses. J Med Chem 60:1648-1661.
26. Qiu X, Wong G, Audet J, Bello A, Fernando L, Alimonti J B, Fausther-Bovendo H, Wei H, Aviles J, Hiatt E, Johnson A, Morton J, Swope K, Bohorov O, Bohorova N, Goodman C, Kim D, Pauly M H, Velasco J, Pettitt J, Olinger G G, Whaley K, Xu B, Strong J E, Zeitlin L, Kobinger G P. 2014. Reversion of advanced Ebola virus disease in nonhuman primates with ZMapp. Nature 514:47-53.
27. Corti D, Misasi J, Mulangu S, Stanley D A, Kanekiyo M, Wollen S, Ploquin A, Doria-Rose N A, Staupe R P, Bailey M, Shi W, Choe M, Marcus H, Thompson E A, Cagigi A, Silacci C, Fernandez-Rodriguez B, Perez L, Sallusto F, Vanzetta F, Agatic G, Cameroni E, Kisalu N, Gordon I, Ledgerwood J E, Mascola J R, Graham B S, Muyembe-Tamfun J J, Trefry J C, Lanzavecchia A, Sullivan N J. 2016. Protective monotherapy against lethal Ebola virus infection by a potently neutralizing antibody. Science 351:1339-42.
28. Sivapalasingam S, Kamal M, Slim R, Hosain R, Shao W, Stoltz R, Yen J, Pologe L G, Cao Y, Partridge M, Sumner G, Lipsich L. 2018. Safety, pharmacokinetics, and immunogenicity of a co-formulated cocktail of three human monoclonal antibodies targeting Ebola virus glycoprotein in healthy adults: a randomised, first-in-human phase 1 study. Lancet Infect Dis 18:884-893.
29. Dyall J, Johnson J C, Hart B J, Postnikova E, Cong Y, Zhou H, Gerhardt D M, Michelotti J, Honko A N, Kern S, DeWald L E, O'Loughlin K G, Green C E, Mirsalis J C, Bennett R S, Olinger G G, Jr., Jahrling P B, Hensley L E. 2018. In Vitro and In Vivo Activity of Amiodarone Against Ebola Virus. J Infect Dis 218:S592-S596.
30. Miller J L, Spiro S G, Dowall S D, Taylor I, Rule A, Alonzi D S, Sayce A C, Wright E, Bentley E M, Thom R, Hall G, Dwek R A, Hewson R, Zitzmann N. 2016. Minimal In Vivo Efficacy of Iminosugars in a Lethal Ebola Virus Guinea Pig Model. PLoS One 11:e0167018.
31. Wec A Z, Bornholdt Z A, He S, Herbert A S, Goodwin E, Wirchnianski A S, Gunn B M, Zhang Z, Zhu W, Liu G, Abelson D M, Moyer C L, Jangra R K, James R M, Bakken R R, Bohorova N, Bohorov O, Kim D H, Pauly M H, Velasco J, Bortz R H, 3rd, Whaley K J, Goldstein T, Anthony S J, Alter G, Walker L M, Dye J M, Zeitlin L, Qiu X, Chandran K. 2019. Development of a Human Antibody Cocktail that Deploys Multiple Functions to Confer Pan-Ebolavirus Protection. Cell Host Microbe 25:39-48 e5.
32. Rijal P, Elias S C, Machado S R, Xiao J, Schimanski L, O'Dowd V, Baker T, Barry E, Mendelsohn S C, Cherry C J, Jin J, Labbe G M, Donnellan F R, Rampling T, Dowall S, Rayner E, Findlay-Wilson S, Carroll M, Guo J, Xu X N, Huang K A, Takada A, Burgess G, McMillan D, Popplewell A, Lightwood D J, Draper S J, Townsend A R. 2019. Therapeutic Monoclonal Antibodies for Ebola Virus Infection Derived from Vaccinated Humans. Cell Rep 27:172-186 e7.
33. Madelain V, Guedj J, Mentre F, Nguyen T H, Jacquot F, Oestereich L, Kadota T, Yamada K, Taburet A M, de Lamballerie X, Raoul H. 2017. Favipiravir Pharmacokinetics in Nonhuman Primates and Insights for Future Efficacy Studies of Hemorrhagic Fever Viruses. Antimicrob Agents Chemother 61.
34. Morris C A, Pokorny R, Lopez-Lazaro L, Miller R M, Arbe-Barnes S, Duparc S, Borghini-Fuhrer I, Shin J S, Fleckenstein L. 2014. Pharmacokinetic interaction between pyronaridine-artesunate and metoprolol. Antimicrob Agents Chemother 58:5900-8.
35. Mankowski D C, Laddison K J, Christopherson P A, Ekins S, Tweedie D J, Lawton M P. 1999. Molecular cloning, expression, and characterization of CYP2D17 from cynomolgus monkey liver. Arch Biochem Biophys 372:189-96.
36. Shimada T, Mimura M, Inoue K, Nakamura S, Oda H, Ohmori S, Yamazaki H. 1997. Cytochrome P450-dependent drug oxidation activities in liver microsomes of various animal species including rats, guinea pigs, dogs, monkeys, and humans. Arch Toxicol 71:401-8.
37. Watanabe S, Takada A, Watanabe T, Ito H, Kida H, Kawaoka Y. 2000. Functional importance of the coiled-coil of the Ebola virus glycoprotein. J Virol 74:10194-201.
38. Cong Y, Dyall J, Hart B J, DeWald L E, Johnson J C, Postnikova E, Zhou H, Gross R, Rojas O, Alexander I, Josleyn N, Zhang T, Michelotti J, Janosko K, Glass P J, Flint M, McMullan L K, Spiropoulou C F, Mierzwa T, Guha R, Shinn P, Michael S, Klumpp-Thomas C, McKnight C, Thomas C, Eakin A E, O'Loughlin K G, Green C E, Catz P, Mirsalis J C, Honko A N, Olinger G G, Jr., Bennett R S, Holbrook M R, Hensley L E, Jahrling P B. 2016. Evaluation of the Activity of Lamivudine and Zidovudine against Ebola Virus. PLoS One 11:e0166318.
39. Quinn K, Brindley M A, Weller M L, Kaludov N, Kondratowicz A, Hunt C L, Sinn P L, McCray P B, Jr., Stein C S, Davidson B L, Flick R, Mandell R, Staplin W, Maury W, Chiorini J A. 2009. Rho GTPases modulate entry of Ebola virus and vesicular stomatitis virus pseudotyped vectors. J Virol
40. Brouillette R B, Maury W. 2017. Production of Filovirus Glycoprotein-Pseudotyped Vesicular Stomatitis Virus for Study of Filovirus Entry Mechanisms. Methods Mol Biol 1628:53-63.
41. Twarog N R, Stewart E, Hammill C V, A AS. 2016. BRAID: A Unifying Paradigm for the Analysis of Combined Drug Action. Sci Rep 6:25523.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method of treating a disease caused by a Nipah virus infection in a subject in need of treatment thereof, wherein the method comprises administering to the subject an effective amount of pyronaridine or a pharmaceutically acceptable salt thereof.

2. The method of claim 1 wherein the administering further comprises administering artesunate.

3. The method of claim 1, wherein the subject is a mammal.

4. The method of claim 3, wherein the subject is a human.

5. The method of claim 1, wherein the administering is performed via oral administration, intranasal administration, or intravenous administration.

* * * * *